United States Patent [19]
Fukuda

[11] Patent Number: 5,910,451
[45] Date of Patent: Jun. 8, 1999

[54] TROPHININ AND TROPHININ-ASSISTING PROTEINS

[75] Inventor: Michiko N. Fukuda, San Diego, Calif.

[73] Assignee: La Jolla Cancer Research Foundation, La Jolla, Calif.

[21] Appl. No.: 08/728,626

[22] Filed: Oct. 10, 1996

Related U.S. Application Data

[63] Continuation of application No. 08/439,818, May 12, 1995, Pat. No. 5,654,145, which is a continuation-in-part of application No. 08/317,522, Oct. 4, 1994, Pat. No. 5,599,918.

[51] Int. Cl.$^6$ .............................. G01N 33/53; C12Q 1/68; C07K 13/00; C07K 15/26
[52] U.S. Cl. .................................. 436/501; 435/4; 435/6; 435/7.1; 530/350; 530/387.1; 530/388.1
[58] Field of Search ...................... 435/7.1, 6.4; 530/350, 530/387.1, 388.1; 436/501

[56] References Cited

U.S. PATENT DOCUMENTS

| | | |
|---|---|---|
| 3,678,076 | 7/1972 | Crenshaw . |
| 4,732,763 | 3/1988 | Beck et al. . |
| 5,227,292 | 7/1993 | White et al. ............................ 435/69.1 |
| 5,240,922 | 8/1993 | O'Neil . |
| 5,242,826 | 9/1993 | Tsilibary et al. . |
| 5,279,941 | 1/1994 | Lessey . |
| 5,279,966 | 1/1994 | Jessell et al. ......................... 435/320.1 |
| 5,344,919 | 9/1994 | Quaranta et al. ...................... 530/395 |
| 5,395,825 | 3/1995 | Feinberg et al. .......................... 514/21 |
| 5,478,725 | 12/1995 | Lessey et al. .......................... 435/7.21 |
| 5,521,067 | 5/1996 | Seshi ..................................... 435/7.24 |
| 5,578,306 | 11/1996 | Lessey ................................ 424/143.1 |
| 5,599,918 | 2/1997 | Fukuda et al. ......................... 536/23.1 |

OTHER PUBLICATIONS

Denker, H.W., "Implantation: A cell biological paradox." *J. of Experimental Zoology*, 266:541–558 (1993).

Flamigni et al., "Factors regulating interaction between trophoblast and human endometrium." *Annals New York Academy of Sciences* 622:177–187 (1991).

Carson et al., "Glycoconjugate synthesis during early pregnancy: Hyaluronate synthesis and function." *Dev. Biol.* 120:228–235 (1987).

Armant et al., "Fibronectin and laminin promote in vitro attachment and outgrowth of mouse blastocysts." *Dev. Biol.* 116:519–523 (1986).

Anderson et al., "Membrane composition of the endometrial epithelium: molecular marker of uterine receptivity to implantation." In: Human Reproduction (Int's Congress Ser., No. 768. R. Iizuka nd K. Semm. eds. *Excerpta Medica Amsterdam* 513–516 (1988).

Carson et al., "Uterine stromal cell chondroitin sulfate proteoglycans bind to collagen type I and inhibit embryo outgrowth in vitro." *Dev. Biol.* 149:307–316 (1992).

Carson et al., Glycoconjugate expression and interactions at the cell surface of mouse uterine epithelial cells and peri-implantation–stage embryos. In: Trophoblast Invasion and Endometrial Receptivity. Novel Aspects of the Cell Biology of Embryo Implantation. (Trophoblast Research. vol. 4.) H.W. Denker and J.D. Aplin eds. Plenum Medical Book Comp. New York, 211–241 (1990).

Hoffman et al., "Uterine receptivity to implantation in the Rabbit: Evidence for a 42kDa glycoprotein as a marker of receptivity." In: Trophoblast Invasion and Endometrial Receptivity. Novel Aspects of the Cell Biology of Embryo Implantation. (Trophoblast Research, vol. 4.) H.W. Denker and J.D. Aplin, eds. Plenum Medical Book Comp., New York, 243–258 (1990).

Lampelo et al., "Purification of rabbit endometrial plasma membranes from receptive and non–receptive uteri." *J. Reprod. Fertil.* 75:475–484 (1985).

Schlafke and Enders, "Cellular basis of interaction between trophoblast and uterus at implantation." *Biol. of Reproduction* 12:41–65 (1975).

Aplin, John D., "Implantation, trophoblast differentiation and haemochorial placentation: mechanistic evidence in vivo and in vitro." *J. of Cell Science* 99:681–692 (1991).

Pullman and Bodmer, "Cloning and characterization of a gene that regulates cell adhesion." *Nature* 356:529–532 (1992).

Harlow and Lane, "Antibodies, a laboratory manual." Cold Spring Harbor Laboratory pp. 53–77 and 139–155 (1988).

Maniatis et al., "Molecular cloning, a laboratory manual." Cold Spring Harbor Laboratory pp. 404–433 (1982).

Carson et al., "Cell surface glycoconjugates as modulators of embryo attachment to uterine epithelial cells." *Int. J. Biochem.*, 26:1269–1277 (1994).

(List continued on next page.)

*Primary Examiner*—Jeffrey Fredman
*Attorney, Agent, or Firm*—Campbell & Flores LLP

[57] ABSTRACT

The present invention provides substantially purified mammalian trophinin which can mediate cell adhesion. The invention also provides substantially purified trophinin-assisting proteins, which interact with trophinin to mediate cell adhesion. The invention further provides antibodies that are specifically reactive with trophinin or a trophinin-assisting protein. In addition, the invention provides active fragments of trophinin or trophinin-assisting proteins. The invention further provides a nucleic acid molecule encoding trophinin or a trophinin-assisting protein, vectors containing the nucleic acid molecules and host cells containing the vectors. The invention also provides a nucleotide sequence that can hybridize to a nucleic acid molecule encoding trophinin or a trophinin-assisting protein. The invention further provides methods to detect trophinin or a trophinin-assisting protein or a nucleic acid molecule encoding trophinin or a trophinin-assisting protein in a sample. The invention also provides methods of effecting cell adhesion by modifying cells to express trophinin or a trophinin-assisting protein. The invention further provides trophinin antagonists and methods to reduce or inhibit cell adhesion. The invention also provides methods to treat cells with trophinin agonists resulting in increased cell adhesion.

9 Claims, 15 Drawing Sheets

OTHER PUBLICATIONS

Svalander et al., Expression of cellCAM–105 in the apical surface of rat uterine epithelium is controlled by ovarian steroid hormones. *J. Reprod. Fert.*, 88:213–221 (1990).

Lindenberg, "Experimental studies on the initial trophoblast endometrial interaction." *Danish medical Bulletin*, 38(5):371–380 (1991).

Diamandis, "Analytical methodology for immunoassays and DNA hybridization assays — current status and selected systems — critical review." *Clinica Chimica ACTA*, 194:19–50 (1990).

Matthews and Kricka, "Analytical strategies for the use of DNA probes." *Analytical Biochem.*, 169:1–25 (1988).

Lichter et al., "Clustering of C2–H2 zinc finger motif sequences within telomeric and fragile site regions of human chromosomes." *Genomics* 13:999–1007 (1992).

Peterson et al., "Functional domains and upstream activation properties of cloned human TATA binding protein." *Science*, 248:1625–1630 (1990).

Vanderslice et al., "Human mast cell tryptase: Multiple cDNAs and genes reveal a multigene serine protease family." *Proc. Natl. Acad. Sci.*, 87:3811–3815 (1990).

Corness et al., "A human somatostatin receptor (SSRT3), located on chromosome 22, displays preferential affinity for somatostatin–14 like peptides." *Febs Letters*, 321:279–284 (1993).

Levesque et al., "DNA transfection in cos cells: A low cost serum–free method compared to lipofection." *Biotechniques*, 11(3):313–315, 317, 318 (1991).

Miki et al., "Simple colorimetric cell—cell adhesion assay using MTT stained leukemia cells." *J. Immunological Methods*, 164:255–261 (1993).

Shapiro et al., "Cloning and characterization of a unique elastolytic metalloproteinase produced by human alveolar macrophages." *J. Biol. Chem.*, 268:23824–23829 (1993).

Mulligan, "The basic science of gene therapy." *Science*, 260:926–930 (1993).

Morgan and Anderson, "Human gene therapy." *Ann. Rev. Biochem.*, 62:191–217 (1993).

Brown et al., "Gene therapy oversold by researchers, journalists." *The Washington Post*, ppA1 and A22 (Dec. 8, 1995).

Marshall, "Gene therapy's growing pains." *Science* 269:1050–1055 (1995).

Sato et al., "Trophoblast cell adhesion molecule: Trophonectin." Genbank accession #U04811, ID #HSP48110. (Submitted Dec. 30, 1993); available to public on Jun. 1, 1995.

Fukuda et al., "Trophinin and tastin, a novel cell adhesion molecule complex with potential involvement in embryo implantation." *Genes & Dev.*, 9:1199–1210. (1995).

Tabibzadah and Babaknia, "The signals and molecular pathways involved in implantation, a symbiotic interaction between blastocyst and endometrium involving adhesion and tissue invasion." *Human Reprod.*, 10(6):1579–1602 (1995).

Aplin et al., "The endometrial cell surface and implantation: expression of the polymorphic mucin MUC–1 and adhesion molecules during the endometrial cycle." *Ann. New York Acad. Sci.* 734:103–121 (1994).

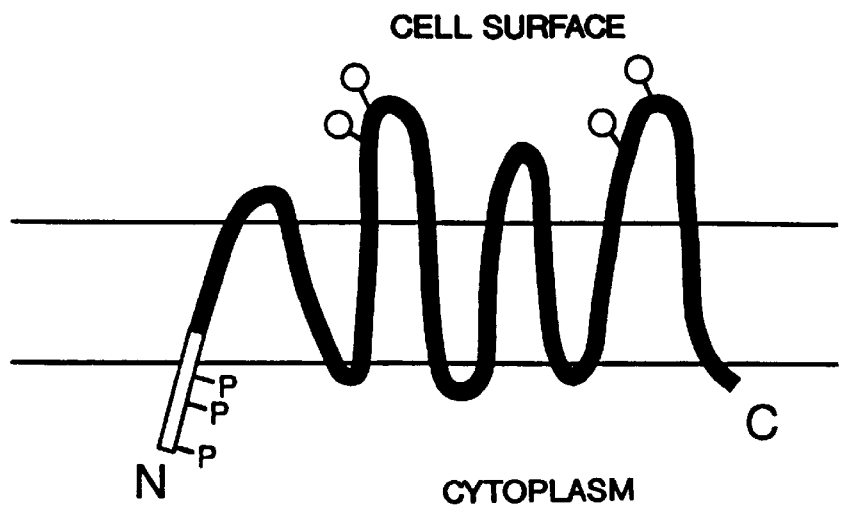

FIG. 5A

69
| | |
|---|---|
| FSGGPGIT | FSGAPITNPG |
| FGVAPSTSAS | FGGAFSTSAG |
| FSNTASIS | FGGALSTAAD |
| FGGTLSTSSS | FGGTPSNSIG |
| FSSAASIS | FGAAPSTSVS |
| FGCAHSTSTS | FGGAHGTSLC |
| FSSEASIS | FGGAPSTSLC |
| FGGMPCTSAS | FGSASNTNLC |
| FSGGVSSS | FGGPPSTSAC |
| FSGPLSTSAT | FSGATSPS |
| FSGGASSG | FCDGPSTSTG |
| FGGTLSTTAG | FSFGNGLSTG |
| FSGVLSTSTS | FGGGLNTSAG |
| FGSAPTTSTV | FGGGLGTSAG |
| FSSALSTSTG | FSGGLSTSSG |
| FGGILSTSVC | FDGGLGTSAG |
| FGGSPSSSGS | FGGGPGTSTG |
| FGGTLSTSIC | FGGGLGTSAG |
| FGGSPCTSTG | FSGGLGTSAG |
| FGGTLSTSVS | FGGGLVTSDG |
| FGGSSSTSAN | FGGGLGTNAS |
| FGGTLSTSIC | FGSTLGTSAG |
| FDGSPSTGAG | FSGGLSTSDG |
| FGGALNTSAS | FGSRPNAS |
| FGSVLNTSTG | FDRGLSTIIG |
| FGGAMSTSAD | FGSGSNTSTG |
| FGGTLSTSVC | FTGEPSTSTG |
| FGGSPGTSVS | FSSGPSSIVG |
| FGSALNTNAG | FSGGPSTGG |
| YGGAVSTNTD | FCSGPSTSG |
| FGGTLSTSVC | FSGGPSTGAG |
| FGGSPSTSAG | FGGGPNTGAG |
| FGGALNTNAS | FGGGPSTSAG |
| FGCAVSTSAS | FGSGAASLGACG |
| FSGAVSTSAC | 745 |

```
         CACCTCTGTCTGTTCCCA                                                                        -181
GTGTTCCAAGAAGAGAAACCTTACGTCAGGCCCCTGCTGACTCCCCCGAGAACTCTGTTCCAATCCCGGTTCTTCCTCCCAAAGAAA        -91
TTCCTTCTTTGTCTCCACCATTCCCCGTCCCGCAAGGCTCCCTGCCCAAACTTCCAGTGCTCCAAGAGACTTCTGGCTGATGCCAC          -1
ATGTGCTCCAGAAGGGACCCTCACTCCTGTGTTCTGCCGCTTCTGAGCAAGAGACTTCTCAGGGCCCCTGGCTTCCCAGGAAGGGA          90
 M  C  S  R  R  D  P  H  S  C  V  L  P  L  L  S  K  R  L  L  S  R  A  P  W  L  P  R  K  G       30
CCCAGTATCCACCCCAGCTGGTGGTGAACAAGAAGCCTCCCTTCTCTCCCACTCCCCCAACAACAGGAAGCCCCCGCTCACTCCCTG        180
 P  S  I  H  P  Q  L  V  V  N  K  K  P  P  F  S  P  T  P  P  T  T  R  K  P  P  L  T  P  L       60
AAGCTCCTGAGAAAGACCCCTGACCCTTCCCCAACAGTTCCCGAGACTGACATGGACCCGCTGCTCCAGAGCCCGGTTTCCAAAGGAC        270
 K  L  L  R  K  T  P  D  P  S  P  T  V  P  E  T  D  M  D  P  L  L  Q  S  P  V  S  Q  K  D       90
ACCCCTTTCCAGATCTCTTCTGGAGTCCAGAAGGAACAGCCGCTCCCACGGGAGAATCACCCGGTTGGTGTGTGGGCTGCCGTCCAA        360
 T  P  F  Q  I  S  S  G  V  Q  K  E  Q  P  L  P  T  G  E  I  T  R  L  G  V  W  A  A  V  Q      120
GCAGTGGAGAGGAAGCTGGAGGCCCAGGCCATGAGGCTACTGACCCTGGAAGGCAGGACAGGGACAAATGAAAAGAAGATAGCCGACTGC     450
 A  V  E  R  K  L  E  A  Q  A  M  R  L  L  T  L  E  G  R  T  G  T  N  E  K  K  I  A  D  C      150
GAGAAGACAGCCGTGGAGTTCGCGAACCATCTGGAGAGCAAGTGGGTCGTGTTGGGACCCTGCTGCCCCAAGAGTATGGGCTGCAGCAGAGG  540
 E  K  T  A  V  E  F  A  N  H  L  E  S  K  W  V  V  L  G  T  L  L  Q  E  Y  G  L  Q  Q  R      180
CGGCTGGAGAACATGGAGAACCTGCTGAAAAACAGAAATTTCTGGATCCTGCGGCTGCCCCCGGGCAGCAATGGAGAAGTTCCAAGTC       630
 R  L  E  N  M  E  N  L  L  K  N  R  N  F  W  I  L  R  L  P  P  G  S  N  G  E  V  P  K  V      210
CCTGTCACATTTGATGATGTTGCTGTGCACTTCTCGGAGCAGGAGTGGGGAAACCTGTCTGAGTGGCAGAAGGAGCTCTACAAGAACGTG    720
 P  V  T  F  D  D  V  A  V  H  F  S  E  Q  E  W  G  N  L  S  E  W  Q  K  E  L  Y  K  N  V      240
ATGAGGGGCAACTACGAGTCCCTGGTTTCCATGGACTATGCAATTTCCAAACCAGACCTCATGTCACAGATGGAGCGGGGAGAGCGGCCC    810
 M  R  G  N  Y  E  S  L  V  S  M  D  Y  A  I  S  K  P  D  L  M  S  Q  M  E  R  G  E  R  P      270
```

```
811        ACCATGCAGGAGCAGGAAGACTCTGAGGAGGGCGAAACGCCGACAGATCCCAGTGCTGCCGCACGATGGGATCGTGATTAAGATCGAGGTA        900
271        T  M  Q  E  Q  E  D  S  E  E  G  E  T  P  T  D  P  S  A  A  H  D  G  I  V  I  K  I  E  V         300

901        CAGACCAACGACGAGGGCTCAGAAAGTTTGGAGACACTTGGAGAGTGAAGACAGGCTTCCAGGACTCAGAGCTG                      990
301        Q  T  N  D  E  G  S  E  S  L  E  T  P  P  E  P  L  M  G  Q  V  E  E  H  G  F  Q  D  S  E  L    330

991        GGTGANCCCTGTGGGAACAGCCAGAACCTGGACATGCAGGAGCCAGAGCAACACGCTGGAGGAGTCCACGGAAGGCTCCAGCGAGTTCAGC    1080
331        G  X  P  C  G  E  Q  P  D  L  D  M  Q  E  P  E  N  T  L  E  E  S  T  E  G  S  S  E  F  S      360

1081       GAACTGAAGCAGATGCTGGTGCAGCAGAGGAACTGCACGGAGGGGATCGTCGTGATCAAGACAGAGGAACAAGACGAGGAGGAAGAGGAG    1170
361        E  L  K  Q  M  L  V  Q  Q  R  N  C  T  E  G  I  V  I  K  T  E  E  Q  D  E  E  E  E  E       390

1171       GAGGAGGATGAGCTGCCGCAGCACTTGCAATCCCTTGGGCAGCTGTCCGGAGATATGAGGCCAGTATGTACCAGACCCCGCTGCCCGGG   1260
391        E  E  D  E  L  P  Q  H  L  Q  S  L  G  Q  L  S  G  R  Y  E  A  S  M  Y  Q  T  P  L  P  G     420

1261       GAGATGTCCCCCGAGGGCGAGGAGTCCCCGCCCCCACTGCAGGTTGGAAACCCCGCAGTGAAAAGGCTGGCCCTTCGTCATGGAGTGGGCAAG  1350
421        E  M  S  P  E  G  E  E  S  P  P  P  L  Q  V  G  N  P  A  V  K  R  L  A  P  S  V  H  G  E     450

1351       CGGGACCTGAGCGAGAACCGCGGGGGCTCGAGCCAGCAGAGTGGGAACAGGCGGGGAGAGCGGCCCTTCACATGCATGGAGTGCGGCAAG    1440
451        R  D  L  S  E  N  R  G  G  S  S  Q  Q  S  G  N  R  R  G  E  R  P  F  T  C  M  E  C  G  K     480

1441       AGCTTCCGCCTGAAGATCAACCTCATCATCCACCAGCGCAACCAACATCAAGGAGGGGCCCTACGAGTGCGCCGAATGTGAGATCA      1530
481        S  F  R  L  K  I  N  L  I  I  H  H  Q  R  N  Q  H  Q  G  G  P  T  S  A  P  N  V  R  S        510

1531       GCTTTCCGGCACAAGCAACAGCTCACGCTGCACCAGCGCATCCACCGCGTTCGTGGTGGCTGCGTCTCACCCGAACGGGGCCCACGTTC     1620
511        A  F  R  H  K  Q  Q  L  T  L  H  Q  R  I  H  R  V  R  G  G  C  V  S  P  E  R  G  P  T  F     540

1621       AACCCCAAGNACGCGCTCAAGCCTCAAGCCGCTCCAAGTCACCGGTCCCCAAGCCTACAAGTGCCCCGAGTGC                  1710
541        N  P  K  X  A  L  K  P  R  P  K  S  P  S  S  G  G  G  G  P  K  P  Y  K  C  P  E  C          570

1711       GACAGCAGCTTCAGCCACAAGTCCAGCCTGACTAAACACCAGATCACGCACACGGGTGAGCGGCCCTACACGGGTGAGCGGCCCTACACGCACAGGGAGCCTGAGTGCAAGAAG   1800
571        D  S  S  F  S  H  K  S  S  L  T  K  H  Q  I  T  H  T  G  E  R  P  Y  T  C  P  E  C  K  K     600
```

FIG. 8B

```
1801  AGCTTCCGCCTGCACATCAGCTTGGTGATCCATCAGCCGGGCAAGCATGAGGTCTCCTTCATCTGCAGCCTGTGCGGCAAG  1890
 601  S   F   R   L   H   I   S   L   V   I   H   Q   R   V   H   A   G   K   H   E   V   S   F   I   C   S   L   C   G   K    630

1891  AGCTTCAGCCGGCCCCTCGCACTCGGCCACCAGGGACTCACACAGGGGAGCGGCCCTTCAAGTGCCCGAGTGCGAAGAGCTTC  1980
 631  S   F   S   R   P   S   H   L   L   R   H   Q   R   T   H   T   G   E   R   P   F   K   C   P   E   C   E   K   S   F    660

1981  AGCGAGAAGTCCAAGCTCACCAACCACTGCCGCGTGCACTCGCGC
 661  S   E   K   S   K   L   T   N   H   C   R   V   H   S   R
```

FIG.8C

TROPHININ AND TROPHININ-ASSISTING PROTEINS

This application is a continuation of application Ser. No. 08/439,818, filed May 12, 1995, now U.S. Pat. No. 5,654,145, which is a Continuation-In-Part of application Ser. No. 08/317,522, filed Oct. 4, 1994, now U.S. Pat. No. 5,599,918.

This work was supported by grant number DK37016 awarded by the National Institutes of Health. The United States government has certain rights in this invention.

BACKGROUND OF THE INVENTION

1. Field of the Invention

This invention relates generally to the fields of biochemistry and molecular biology and more specifically to cell adhesion molecules.

2. Background Information

The early stages of pregnancy involve fertilization of an egg by a sperm, followed by cell division and implantation of the embryo into the uterine cell wall. The inability of the embryo to properly implant in the uterus is a significant cause of pregnancy failure following in vivo or in vitro fertilization. The early events of implantation are characterized by an initial attachment of the embryo's external cell lining (trophoblast layer) to the cells lining the uterus (endometrial epithelium) followed by or in parallel with adhesion of these two cell types. The molecular events involved in the early steps in implantation are not well understood.

Embryo attachment and adhesion to the uterine endometrium is unusual in that cells from these two sources adhere at their apical surfaces. In contrast, most other epithelial cell interactions adhere at their basal and lateral cell surfaces. The unique ability of trophoblast and endometrial cells to adhere may result from apical display of adhesion molecules normally located at basal and lateral surfaces. Alternatively, adhesion of these cell types in implantation may be mediated by unique cell surface molecules.

Recent experiments suggest that certain endometrial tumor cell lines express characteristics associated with implantation-receptive endometrial tissue. In these experiments, trophoblast cells derived from germ cell tumors adhered to monolayers of endometrial adenocarcinoma cells via their apical cell surfaces. Morphological analysis of the adhering cell surfaces showed characteristics in common with early stage implantation. However, the molecules involved in the critical early adhesion step of embryo implantation were not identified. Thus, a need exists to identify the molecules responsible for adhesion of the embryo to the uterine lining. The present invention satisfies this need and provides related advantages as well.

SUMMARY OF THE INVENTION

The present invention provides substantially purified mammalian trophinin, which mediates adhesion of cells at their apical surfaces. In addition, the invention provides a family of substantially purified mammalian trophinin-assisting proteins, including tastin, bystin and lastin, which can be involved in trophinin-mediated cell adhesion. The invention also provides antibodies that specifically bind trophinin or a trophinin-assisting protein. Such antibodies can be useful, for example, to detect trophinin or a trophinin-assisting protein in a sample. In addition, the invention provides active fragments of trophinin and trophinin-assisting proteins.

The invention also provides nucleic acid molecules encoding trophinin or a trophinin-assisting protein, vectors containing the nucleic acid molecules and host cells containing the vectors. These nucleic acid molecules can be used to express trophinin or a trophinin-assisting protein in a cell that otherwise does not express trophinin or a trophinin-assisting protein or expresses an aberrant trophinin or trophinin-assisting protein. The invention further provides methods for adhering cells together. In addition, the invention provides methods to inhibit trophinin-mediated adhesion of cells by contacting cells with a trophinin antagonist. The invention also provides a method to increase or decrease the likelihood of embryo implantation in a subject.

BRIEF DESCRIPTION OF FIGURES

FIGS. 1A and 1B show binding of embryonic trophoblastic cells HT-H (1), endometrial adenocarcinoma cells SNG-M (2) and monkey kidney cells COS-1 (3) to a monolayer of SNG-M cells (FIG. 1A) or HT-H cells (FIG. 1B). After 20 minutes (min) at room temperature (RT), nonadherent cells were removed by washing with (+) or without (−) 1 mM EDTA. The x axis indicates the percentage of cells that bound to the monolayer.

FIG. 1C shows the binding of COS-1 cells transfected with vector alone (1), vector containing tastin cDNA (2), vector containing trophinin cDNA (3) and a mixture of vectors containing tastin cDNA and trophinin cDNA (4) to a monolayer of SNG-M cells. Non adherent cells were removed by washing with 1 mM EDTA.

FIG. 1D presents the effects of anti-trophinin antibodies on cell adhesion. HT-H cells (1) or SNG-M cells (2) were added to a monolayer of SNG-M cells previously treated with pre-immune serum (−) or with anti-trophinin antiserum anti-GST-553 (+). Non adherent cells were removed by washing with 1 mM EDTA.

FIG. 2A, 10 min post co-culture revealing microvilli at the lower side of an HT-H cell (H) facing the upper surface of the SNG-M cell (S). The basal surface of the HT-H cell is indicated by short arrows. Scale bar=5 μm.

FIG. 2B is a 4.4× higher magnification of the area indicated by the parentheses in FIG. 2A. Contact of the two cell types via microvilli is evident.

FIG. 2C, 6 hr post-culture shows a HT-H cell (H) adhered to an SNG-M cell (S). Contact between the two cell types is closer than observed at 10 min culture. The microvilli are flattened in both cells and extend directly from each cell to the plasma membrane of the other cell. The SNG-M cells at this stage of contact often show invagination activity (arrow). Scale bar=1 μM.

FIG. 2D, 4 days post co-culture shows a HT-H cell (H) adhered to a SNG-M cell (S). Microvilli are absent from the surfaces of both cells and contact primarily is focal, with occasional development of an adherent junction (arrow). Scale bar=0.5 μM.

FIG. 3 presents the complete nucleotide sequence (SEQ ID NO: 1) and deduced amino acid sequence (SEQ ID NO: 2) of trophinin. Single letter amino acid symbols are used.

Areas of the protein are indicated as follows: transmembrane domains (underlined), cytoplasmic domains (italics) and cell surface domains (bolded). Potential sites for N-linked and O-linked glycosylation are underlined; potential sites for protein kinase phosphorylation are indicated by shadowed letters.

Figure 4:
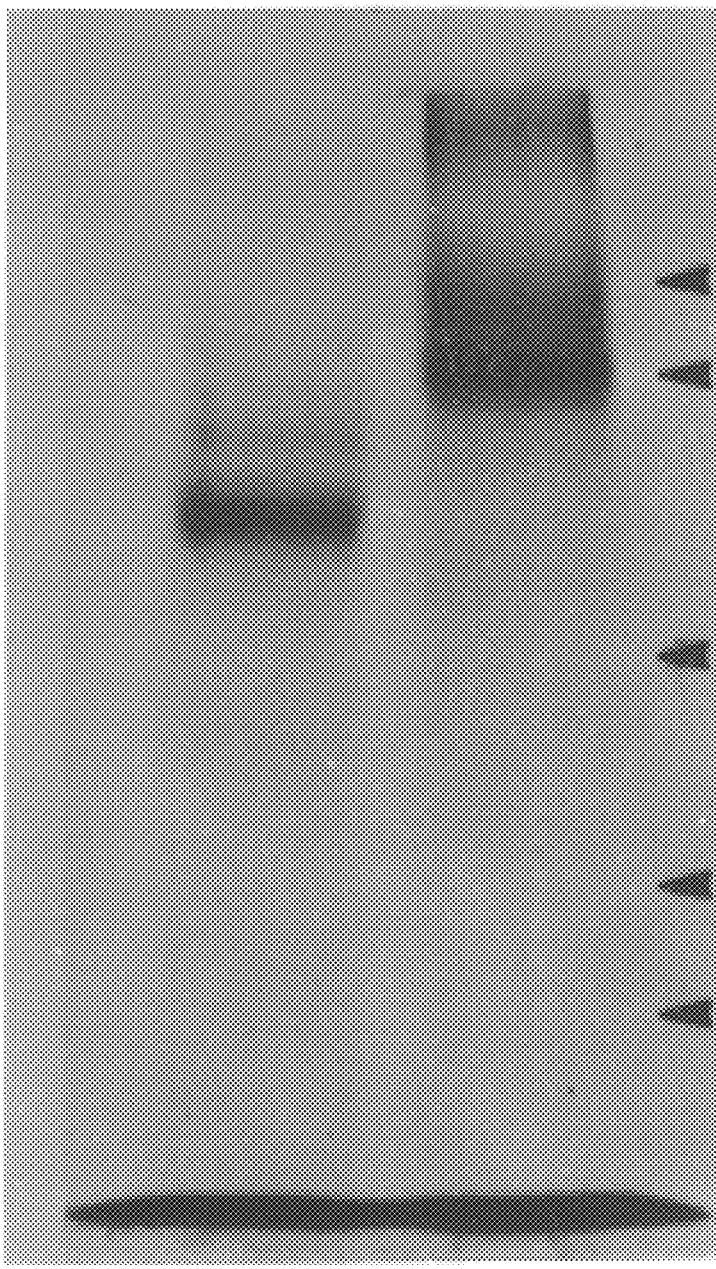

FIG. 4 is an autoradiograph of an SDS-polyacrylamide gel following electrophoresis of $^{35}$S-labeled proteins obtained by in vitro translation of trophinin (lane 1) and tastin (lane 2) cDNA. Numbers on the right indicate the migration of molecular weight markers.

FIGS. 5A and 5B show a schematic representation of the trophinin molecule in the cell membrane and identify a repeating decapeptide sequence in the molecule.

FIG. 5A shows the topology of a trophinin molecule within the cell membrane. Eight potential transmembrane domains are represented and the portion of trophinin containing the tandem decapeptide repeating sequence is filled-in. The amino terminus (N), the carboxy terminus (C), potential sites for protein kinase phosphorylation (P) and potential sites for N-linked glycosylation (circles) are indicated.

FIG. 5B shows the amino acid sequence of trophinin from position 69 to 745 (SEQ ID NO: 3) in a form that identifies the individual tandem decapeptide units.

Figure 6A:
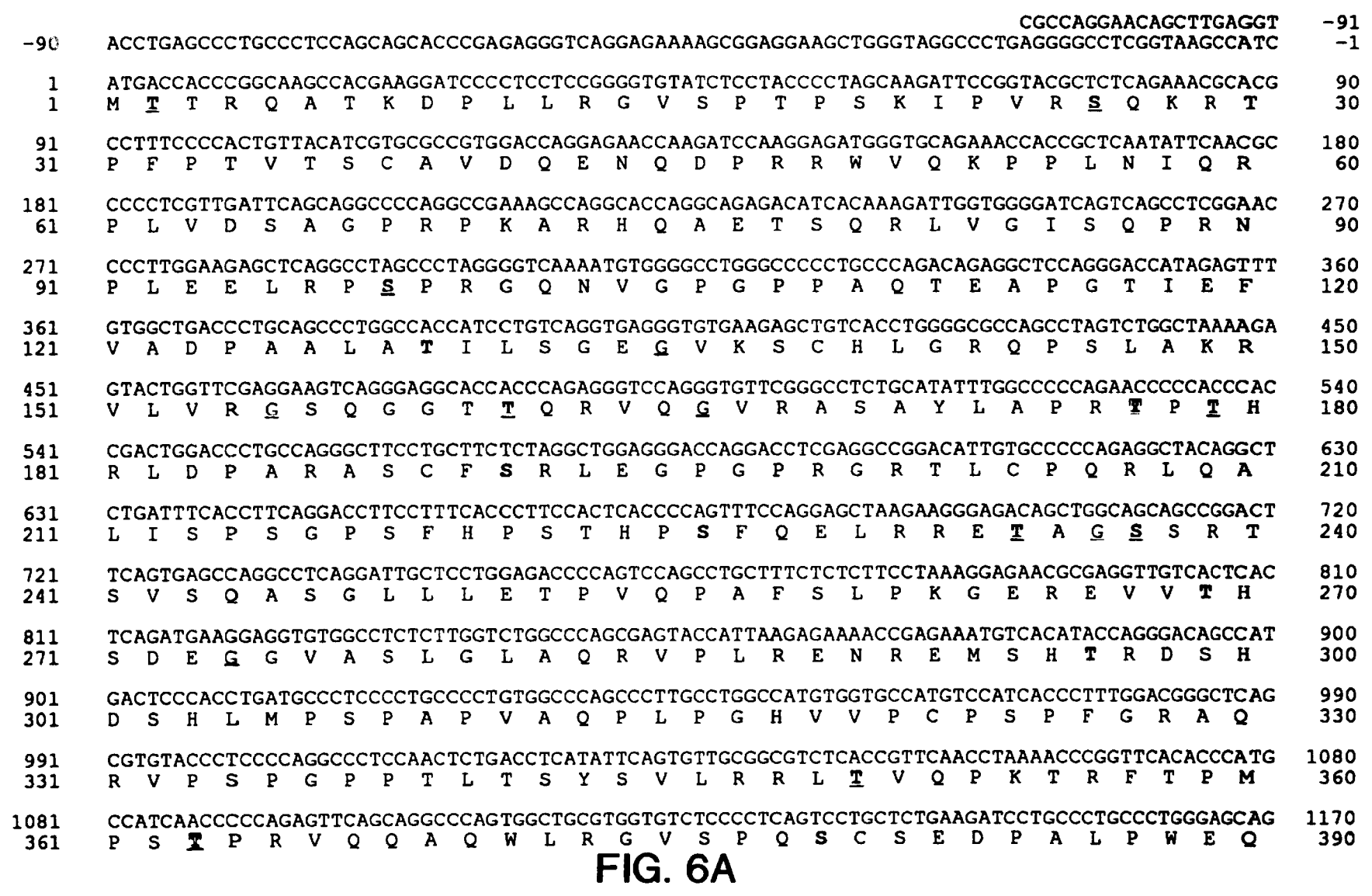
Figure 6B:
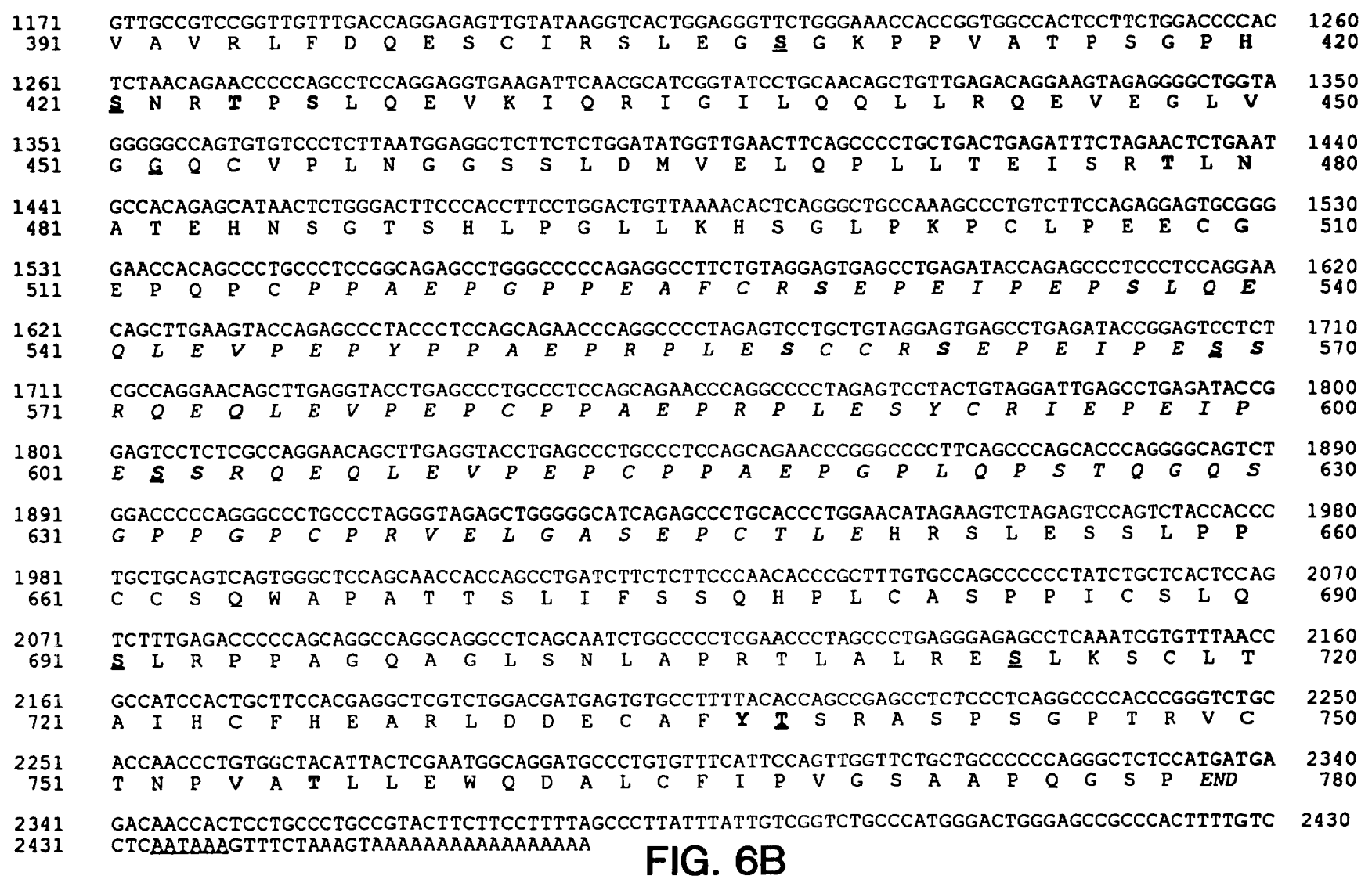

FIG. 6 presents the complete nucleotide sequence (SEQ ID NO: 4) and deduced amino acid sequence (SEQ ID NO: 5) of the tastin cDNA clone. Single letter amino acid symbols are used. Potential sites for phosphorylation by protein kinase C (underlined bold), cAMP/cGMP dependent protein kinase (underlined), casein kinase II (bold) and MAP kinase (shadowed letters) are indicated. The location of 4 tandem repeat sequences that contain the majority of cysteines in the molecule are indicated by italics between residues 516 and 650.

Figure 7:
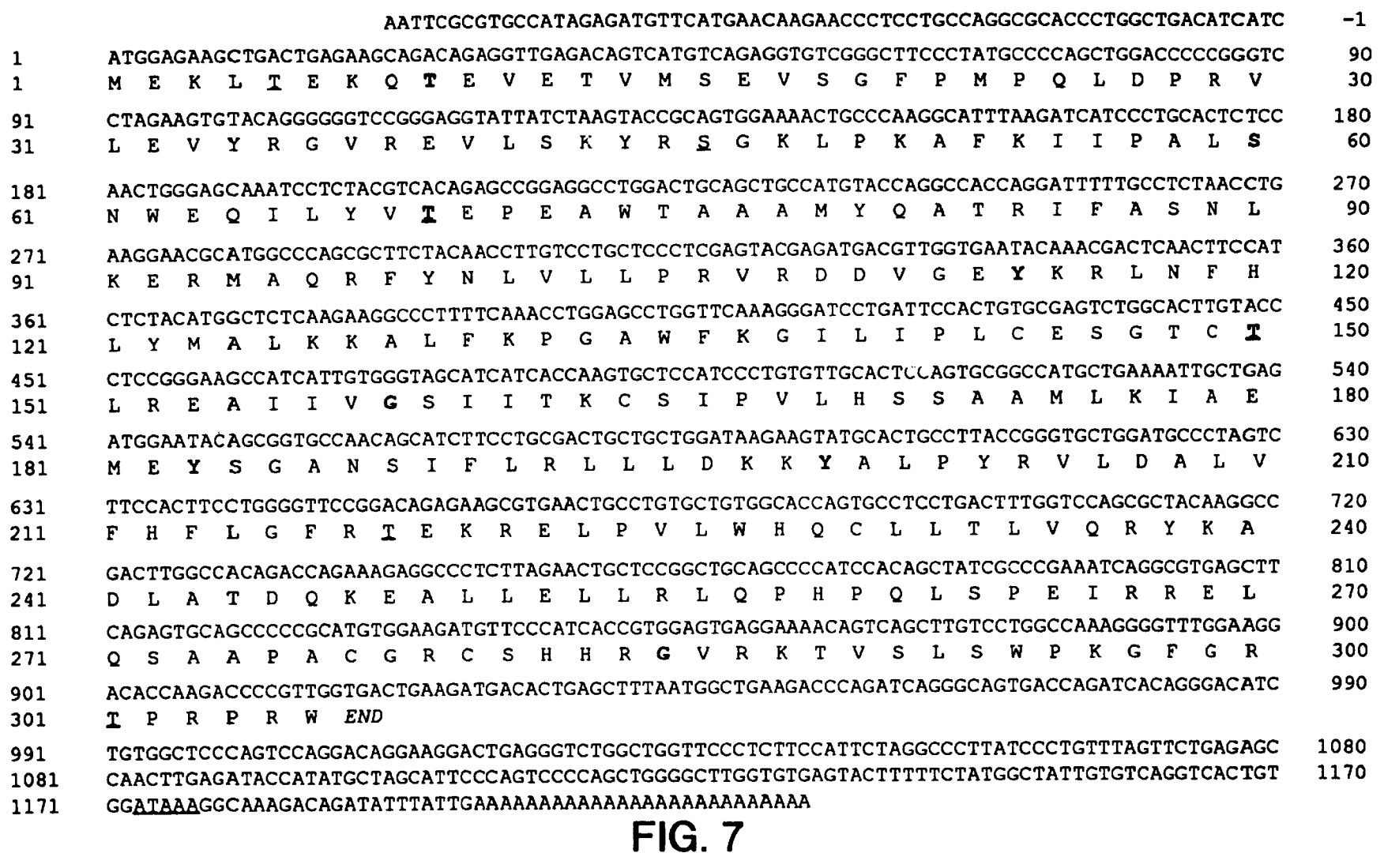

FIG. 7 presents the complete nucleotide sequence (SEQ ID NO: 6) and deduced amino acid sequence (SEQ ID NO: 7) of bystin. Single letter amino acid symbols are used. Threonine and serine residues within potential sites for phosphorylation by protein kinase C (underlined) and casein kinase II (bolded) are indicated. Potential sites for phosphorylation of tyrosine residues by tyrosine kinase and potential sites for myristoylation of glycine residues are indicated in bold.

FIG. 8 presents a partial nucleotide sequence (SEQ ID NO: 8) and deduced amino acid sequence (SEQ ID NO: 9) of a portion of the lastin gene. The cDNA obtained for the lastin gene was missing the 3' end of the coding sequence and the poly-A tail. Single letter amino acid symbols are used. Potential threonine and serine within sites for phosphorylation by protein kinase C (underlined) and casein kinase II (bolded) are indicated. Potential sites for myristoylation of glycine residues are indicated in bold. Amino acid residues indicated by an X and nucleotides indicated by an N are unknown.

Figure 9A:
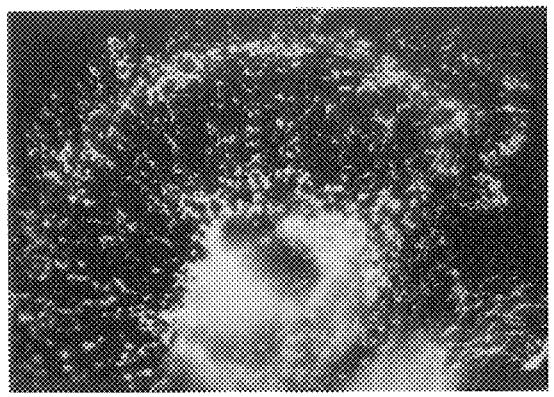

FIGS. 9A, 9B, 9C and 9D are immunofluorescence micrographs detailing expression of trophinin or tastin in HT-H cells and SNG-M cells as detected by antibodies to the N-terminal region of trophinin (residue 23–31 SEQ ID NO. 10) and the N-terminal region of tastin (residue 41–49 SEQ ID NO. 11). FIG. 9A (HT-H) and FIG. 9B (SNG-M) show staining for trophinin while FIG. 9C (HT-H) and FIG. 9D (SNG-M) show staining for tastin. Scale bars=10 μM.

FIGS. 10A, 10B, 10C and 10D are immunofluorescence micrographs showing staining of trophinin and tastin in various human tissues as detected by antibodies to the N-terminal region of trophinin (residue 23–31) and the N-terminal region of tastin (residue 41–49).

Figure 10A:
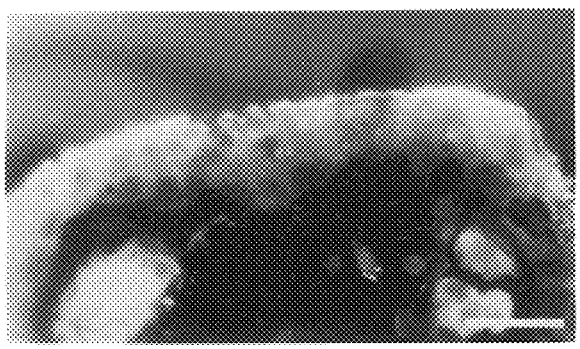
Figure 10B:
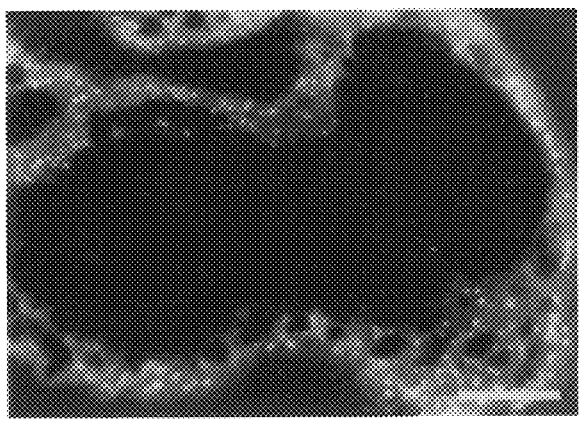

FIGS. 10A and 10B present immunofluorescence micrographs of placental tissues from early pregnancy stained via anti-trophinin antibodies. FIG. 10A shows a region of trophinin staining of the chorionic villus of a placenta obtained at seven weeks pregnancy. Fewer than half the villi in this tissue were stained for trophinin. Staining of trophinin in the villus in FIG. 10A. is observed at the apical plasma membranes of the syncytiotrophoblasts. FIG. 10B is a chorionic villus of placenta obtained at nine weeks pregnancy. Lysosomal vesicles of the syncytiotrophoblasts in some villi show staining for trophinin. Scale bars=10 μM.

Figure 10C:
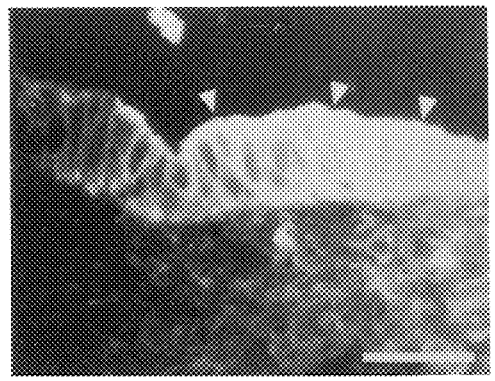
Figure 10D:
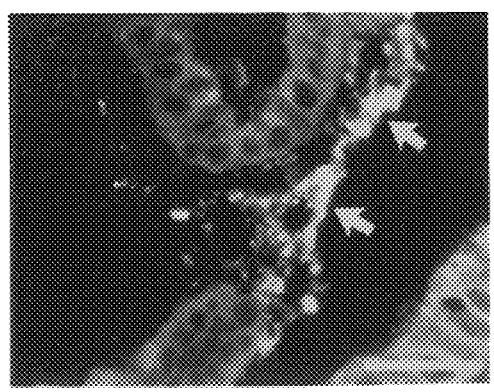

FIGS. 10C and 10D display immunofluorescence micrographs of endometrial epithelium stained via anti-trophinin antibodies. FIG. 10C shows staining for trophinin at the apical membrane (arrowheads) of the surface epithelium from early secretory phase (approximately day 16/17 of the menstrual cycle). FIG. 10D shows staining for trophinin in mucinous materials (arrow; in glandular lumen) associated with endometrial tubular epithelium from middle secretory phase (approximately day 22 of the menstrual cycle). Scale bars=10 μM.

FIGS. 11A, 11B, 11C and 11D display immunofluorescence micrographs of a monkey embryo and the implantation site from a monkey stained via antibodies to the N-terminal region of trophinin (residue 23–31).

Figure 11A:
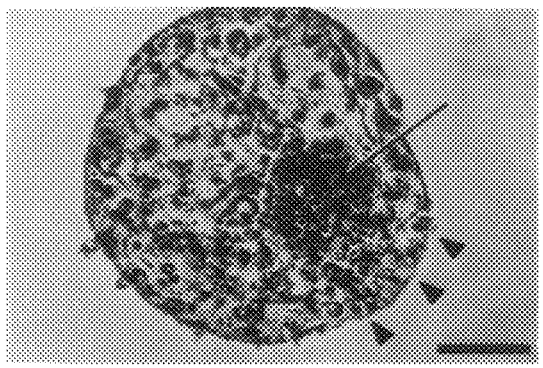
Figure 11C:
Figure 11B:
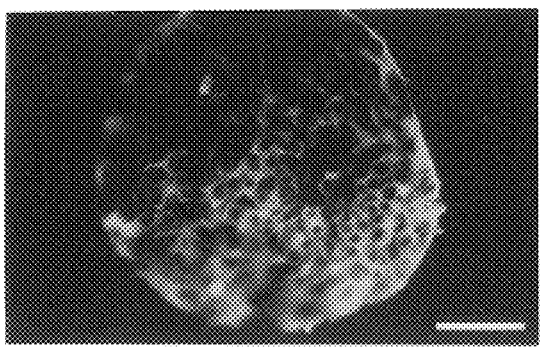

FIGS. 11A and 11B shows an expanded blastocyst (zona pellucida removed) from a rhesus monkey under phase microscopy (11A) and after immunofluorescence staining with an anti-trophinin antibody (11B). The long arrows indicate cell mass in FIG. 11A while arrowheads indicate the embryonic pole in FIG. 11B Strong staining for trophinin is associated with cells of the trophectoderm (11B). Staining of cells located at the embryonic pole (arrowheads) is stronger than staining of cells versus cells located at the mural pole (small arrows). Scale bars=25 μM.

FIG. 11C shows a tissue section taken from the site of implantation of a 15 day macaque monkey blastocyst. A light micrograph shows endometrium (E), trophoblast (T), cytotrophoblasts of blastocyst (short arrow), anchoring villi of trophoblasts penetrating the endothelial epithelium (long arrows) and plaque cells in hypertrophic endometrial epithelium (asterisks). The border between the embryo and the uterine epithelium is indicated by a line. Scale bar=200 μM.

Figure 11D:
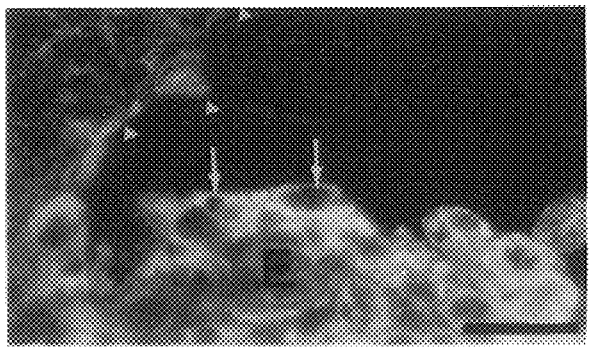

FIG. 11D is an immunofluorescence micrograph of a higher magnification of the same tissue section described in FIG. 11C (site located in brackets) stained with anti-trophinin antibodies to the N-terminal region of trophinin (residue 23–31). Trophoblast layer (T) and endometrial epithelium (E) show strong staining of trophoblast cells (triangles) and endometrial cells (arrows) located at the interface between the two tissues. Scale bar=10 μM.

DETAILED DESCRIPTION OF THE INVENTION

The present invention provides novel proteins involved in embryo adhesion to the uterus during implantation. The invention provides trophinin, which is present in the cell membrane of trophoblast cells and uterine epithelial cells. The invention also provides a family of cytoplasmic trophinin-assisting proteins, including tastin, bystin and lastin, which can interact with trophinin to effect cell adhesion.

Although the precise morphological events of implantation vary from species to species, an essential feature is the formation of allogenic and heterotypic cell-to-cell contact between embryonic and maternal cells. The early events of implantation include an initial apposition of the trophoblast to the uterus and subsequent adhesion of the trophoblast to the endometrial epithelium (Enders, et al. In *Cellular and Molecular Aspects of Implantation* (Plenum Press, New York, 1981); Kaufman, In *Biology of the Trophoblast* (Elsevier Scientific 1985); Aplin, *J. Reprod. Fert.* 91:525–541 (1991); Ringler and Strauss, *Current. Opin. Cell Biol.* 2:703–708 (1990)). The initial attachment of the trophoblast to the endometrial epithelium is unusual in that this cell-to-cell contact occurs via their respective apical cell membranes.

In general, the basal and lateral surfaces of epithelial cells rather than their apical surfaces provide sites for adhesion between cells. The unique ability of trophoblast and endometrial cells to adhere at their apical surfaces can be due to apical display of adhesion molecules normally located at the basal and lateral surfaces of the cells. For example, atypical expression of heparan sulfate and integrins on the surface of the mouse blastocyst at peri-implantation stage has been observed (Farach et al., *Devel. Biol.* 123:401–410 (1987); Sutherland et al., *J. Cell Biol.* 106:1331–1348 (1988) ; Leivo et al., *Devel. Biol.* 76:100–114 (1980); Armant et al., *Devel. Biol.* 116:519–523 (1986)). Alternatively, unique apical adhesion of trophoblast with endometrial epithelium can be mediated by unique cell surface molecules (Kliman et al., In *Blastocyst Implantation*, (Adams Publishing 1989)). Attempts to identify molecules involved in embryo implantation have been conducted both in vivo and in vitro (Lindenberg et al., *Hum. Reprod.* 1:533–538 (1988); Armant et al., supra, 1986; Leivo et al., supra, 1980; Sutherland et al., supra, 1988; Farach et al., supra, 1987; Yamagata and Yamazaki, *Biochem. Biophys. Res. Commun.* 181:1004–1009 (1991); Romagnano and Babiarz, *In vitro. Devel. Biol.* 141:254–261 (1990)), however, none of these studies have identified adhesion molecules that are unique to embryo implantation.

Figure 1A:
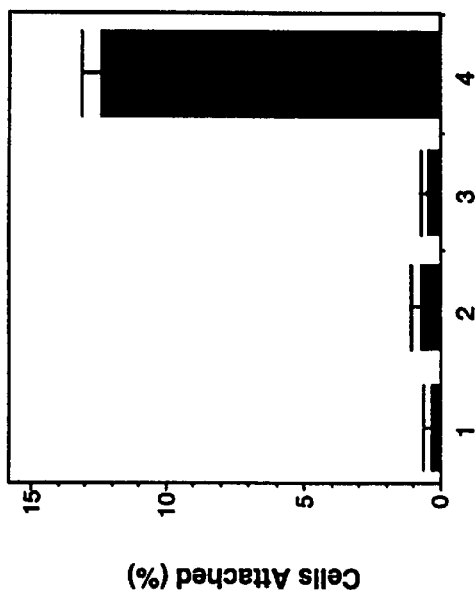
FIGS. 1A, 1B, 1C and 1D collectively show the results of in vitro adhesion cell assays evaluating the ability of cell lines to undergo trophinin-mediated cell adhesion.
Figure 1B:
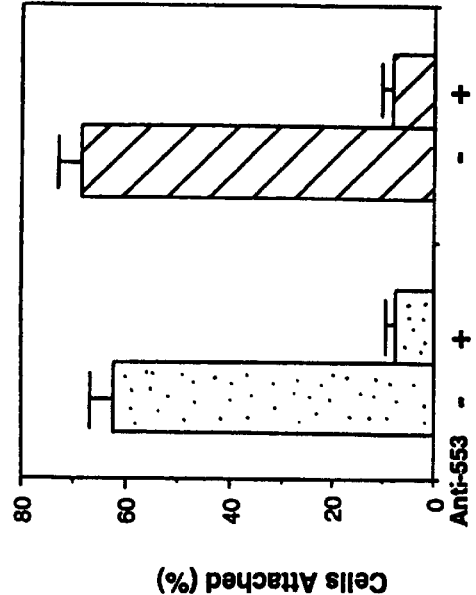

As disclosed herein, trophinin is involved in apical cell adhesion between cultured trophoblast HT-H cells and endometrial adenocarcinoma SNG-M cells (see FIGS. 1A and 1B). Trophinin also mediates adhesion between HT-H and HT-H cells and between SNG-M and SNG-M cells (See Example I). In contrast, these two cell types do not adhere to other types of epithelial cells such as HeLa, A431, SW480 and HepG-2 cells (Table 1). Thus, adhesion between HT-H and SNG-M cells is cell-type specific.

Figure 3A:
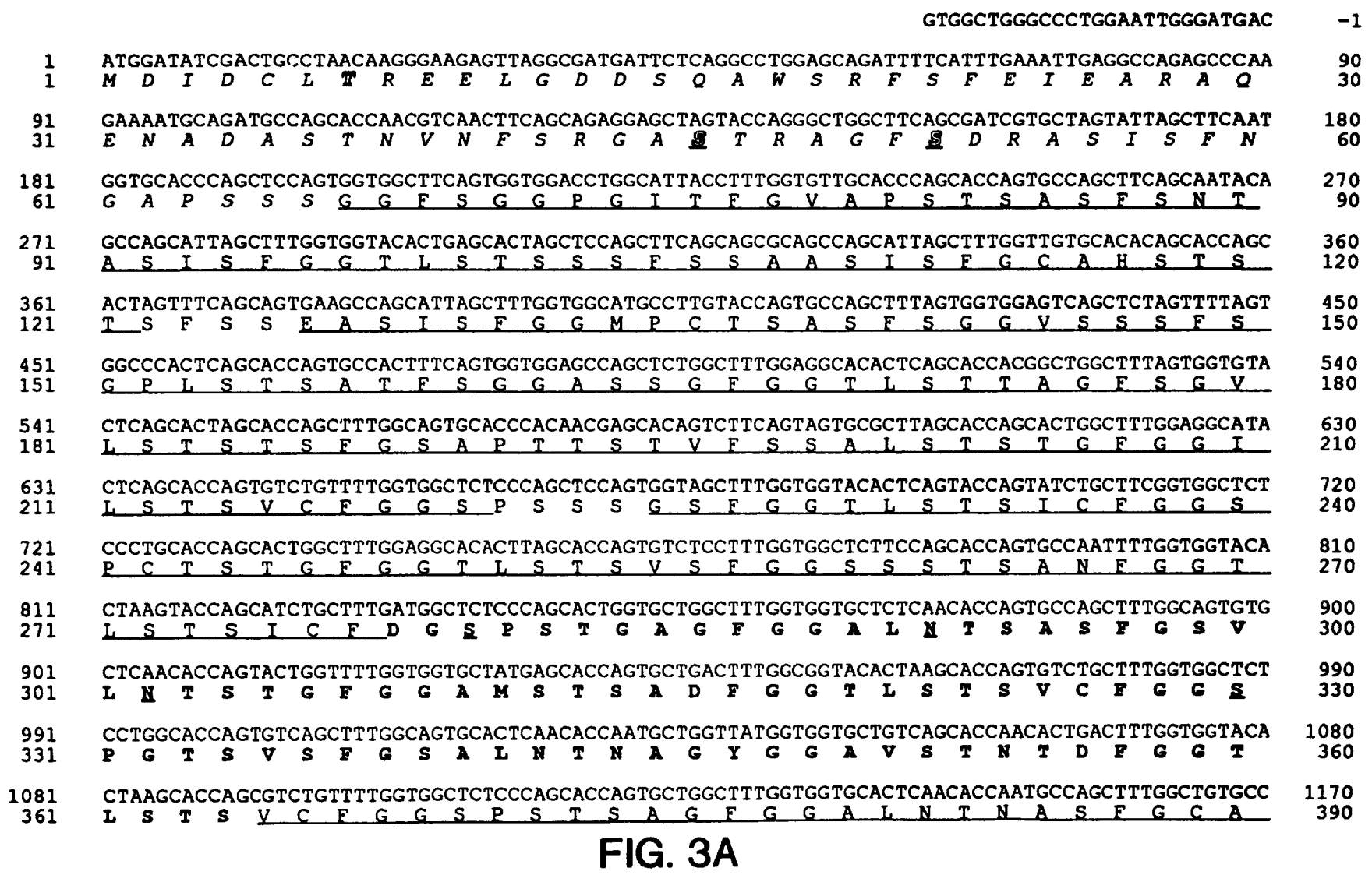
Figure 3B:
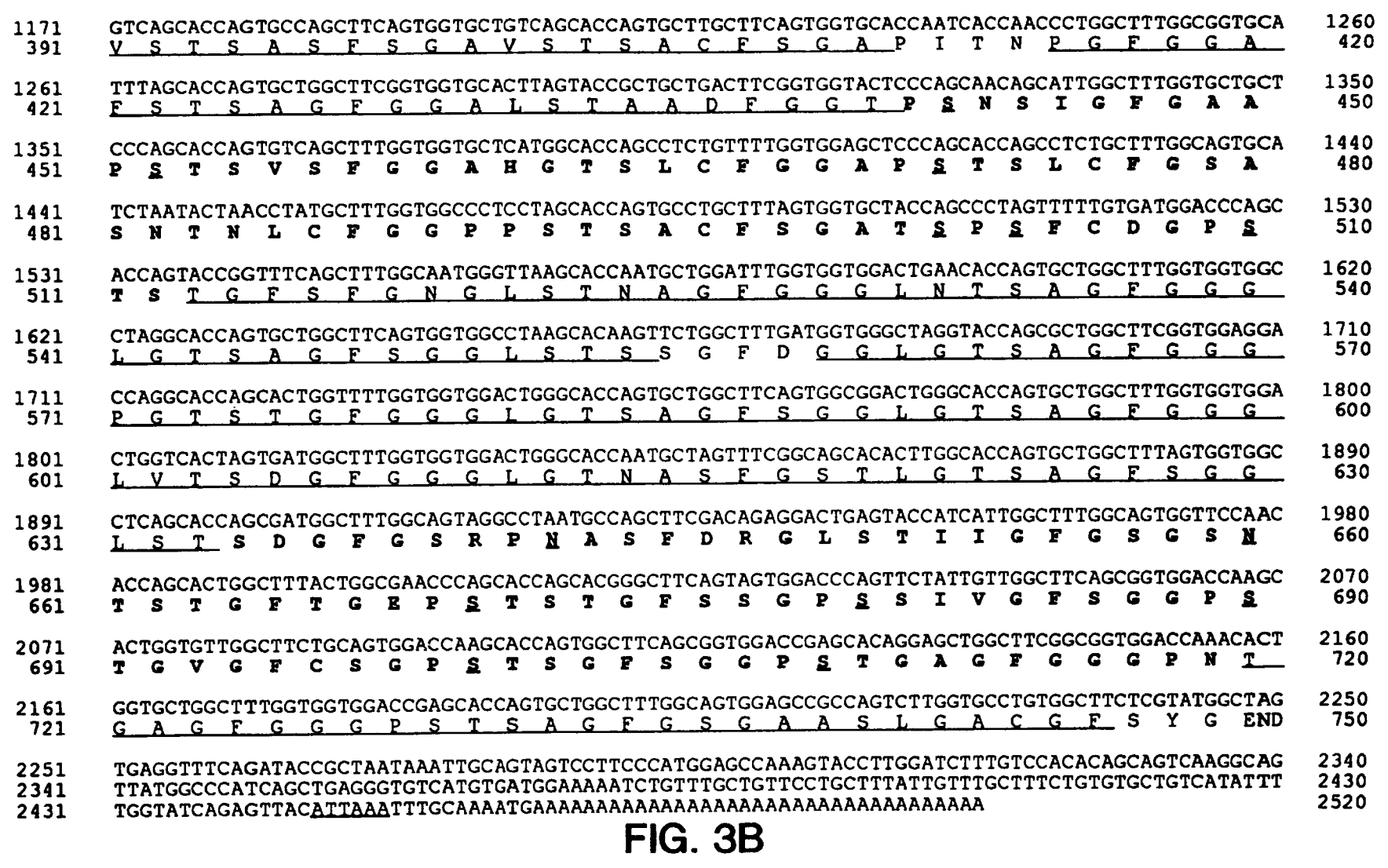

The invention provides a substantially purified mammalian trophinin having substantially the amino acid sequence of human trophinin shown in FIG. 3 (SEQ ID NO: 2). The amino acid sequence of trophinin was derived from the nucleotide sequence shown in FIG. 3 (SEQ ID NO: 1). As used herein, the term "substantially the amino acid sequence" means the amino acid sequence of human trophinin as shown in FIG. 3 (SEQ ID NO: 2), as well as amino acid sequences that are similar to SEQ ID NO: 2, but have one or more amino acid additions, deletions or substitutions that do not substantially alter the ability of the encoded protein to function like a trophinin and, for example, mediate cell adhesion or elicit trophinin specific antibodies. In general, an amino acid sequence having at least 65% sequence homology with the amino sequence of FIG. 3 (SEQ ID NO: 2) is considered substantially the same sequence. Thus, a mammalian trophinin is characterized, in part, by having a greater homology with other mammalian trophinins such as human trophinin as compared with other cell adhesion type molecules.

It is well recognized that various amino acids in a polypeptide can be replaced by other naturally- or non-naturally-occurring L- or D-amino acids having equivalent reactive side chains or by other chemical compounds without substantially changing the biological activity of the polypeptide. For example, a hydrophobic amino acid such as leucine can be replaced by another hydrophobic amino acid such as alanine without substantially changing the amino acid sequence or activity of a trophinin polypeptide. In addition, the N-terminus or C-terminus or a reactive side chain of an amino acid can be modified, for example, by acetylation or amidation, without substantially changing the activity of a trophinin polypeptide. Such modified proteins can have advantageous properties including, for example, increased stability in vivo or in vitro, and are considered to be within the meaning of the term "substantially the amino acid sequence."

As used herein, the term "substantially purified" means a protein that is in a form that is relatively free from contaminating lipids, proteins, nucleic acids or other material normally associated with a protein in a cell. Substantially purified trophinin can be obtained, for example, using well known biochemical methods of purification or by expressing a recombinant nucleic acid molecule encoding a trophinin such as the nucleic acid molecule shown in SEQ ID NO: 1. In addition, an amino acid sequence consisting of at least a portion of the amino acid sequence of SEQ ID NO: 2, can be chemically synthesized or can be produced by expressing a portion of the nucleotide sequence shown in SEQ ID NO: 1 (see Example V and VI).

As used herein, the terms "protein" or "polypeptide" are used in their broadest sense to mean a sequence of amino acids that can be encoded by a cellular gene or by a recombinant nucleic acid sequence or can be chemically synthesized. In some cases, the term "polypeptide" is used in referring to a portion of an amino acid sequence encoding a full length protein. An active fragment of trophinin as defined below can be an example of such a polypeptide. A protein can be a complete, full length gene product, which can be a core protein having no amino acid modifications or can be a post-translationally modified form of a protein such as a phosphoprotein, glycoprotein, proteoglycan, lipoprotein or nucleoprotein.

Trophinin is a cell membrane protein that is characterized primarily by its ability to effect cell adhesion. It is recognized that the ability of trophinin to effect cell adhesion can be due to a portion of the full length protein. For example, as discussed below, greater than 90% of trophinin is composed of a repeating decapeptide sequence that can be involved in binding to another trophinin molecule. Thus, a polypeptide that contains only a portion of the full length trophinin protein can be useful for mediating cell adhesion. As used herein, the term "trophinin" means the full length trophinin protein or an active fragment thereof. As used herein, the term "active fragment" means a portion of a full length protein, provided the portion retains at least one activity that is characteristic of the full length protein. For example, an active fragment of trophinin can be a portion of the full length trophinin protein that can effect cell adhesion or can elicit specific antibodies to trophinin. An active fragment of trophinin can be identified, for example, by expressing a portion of the trophinin protein in a cell and determining that the cell can adhere to a trophinin expressing cell (see Example I).

The complete amino acid sequence of human trophinin was deduced from the nucleotide sequence of a cDNA clone encoding human trophinin. The trophinin cDNA (SEQ ID NO: 1) contains an open reading frame coding for 749 amino acids (FIG. 3). Trophinin has no significant homology to sequences contained in protein and nucleic acid databases. In vitro translation of trophinin cDNA and analysis using sodium dodecyl sulfate polyacrylamide gel electrophoresis (SDS-PAGE) showed that trophinin is synthesized as a major product of 61 kiloDaltons (kDa) (FIG. 4). This experimentally determined molecular mass is in agreement with the predicted molecular mass of 69.29 kDa based on the cDNA open reading frame.

Hydropathy analysis (Kyte and Doolittle, *J. Mol. Biol.* 157:105–132 (1982)) of trophinin indicates trophinin is an intrinsic membrane protein having 8 separate transmembrane domains (FIG. 5A). The relative proportion of trophinin localized in the cytoplasm, in the membrane bilayer and on the cell surface is 10%, 56% and 34%, respectively. The amino terminal portion of trophinin is likely located in the cytoplasm because the first putative membrane spanning domain (amino acids 66 to 120) follows an arginine residue at position 54, which can function as a stop transfer signal during translocation into the endoplasmic reticulum, and because antibodies raised to an amino terminal peptide of trophinin (residues 23–31) react only with cells that have had their membranes permeabilized by detergent treatment (see Example VI).

The amino terminal region of trophinin contains many serine and threonine residues that can function as potential phosphorylation sites for enzymes such as casein kinase II (Kemp and Pearson, *Trends Biochem. Sci.* 15:342–346 (1990)), protein kinase C, and cAMP/cGMP dependent kinases (see Example III). Four potential N-glycosylation sites and thirteen potential O-glycosylation sites are present within the predicted cell surface domains of trophinin (FIG. 3).

Greater than 90% of trophinin is composed of a tandemly repeated decapeptide motif. There are 69 such repeat sequences, which exhibit some variation in sequence and length (FIG. 5B). Portions of the decapeptide motifs are contained within three regions of trophinin that are hydrophilic in character and are exposed on the external side of the cell plasma membrane. The external trophinin domains are located from amino acid positions 278 to 364 (SEQ ID NO: 20), 441 to 512 (SEQ ID NO: 21) and 634 to 719 (SEQ ID NO: 22) (see bold lettering in FIG. 3). Protein secondary structure algorithms (Garnier et al., *J. Mol. Biol.* 120:97–120 (1978); Gascuel and Golmard, *Comput. Appl. Biosci.* 4:357–365 (1988)) predict that the decapeptide repeats conform to a repeated β-turn structure, which can be involved in homophilic adhesion (not shown).

In addition to trophinin, a cell can require the expression of a trophinin-assisting protein in order to effect cell adhesion. The present invention provides a family of substantially purified mammalian trophinin-assisting proteins having substantially the amino acid sequences of human tastin (SEQ ID NO: 5), human bystin (SEQ ID NO: 7) and human lastin (SEQ ID NO: 9) as shown in FIGS. 6, 7 and 8, respectively. A trophinin-assisting protein can enable adhesion of cells that express trophinin. As used herein, the term "substantially the amino acid sequence" means the disclosed amino acid sequence of human tastin (SEQ ID NO: 5), human bystin (SEQ ID NO: 7) or human lastin (SEQ ID NO: 9) as well as amino acid sequences that are similar to SEQ ID NO: 5, SEQ ID NO: 7 or SEQ ID NO: 9, respectively, but have one or more amino acid additions, deletions or substitutions that do not substantially alter the ability of the encoded protein to function like a trophinin-assisting protein and, for example, mediate cell adhesion or elicit a trophinin-assisting protein specific antibody.

As used herein, the term "trophinin-assisting protein" is used generally to mean a member of the trophinin-assisting protein family of proteins as defined by their ability to assist trophinin in mediating adhesion of cells. Trophinin-assisting proteins include such family members as tastin, bystin or lastin and can be a full length trophinin-assisting protein or an active fragment of a trophinin-assisting protein. For example, amino acids 1 to 675 of lastin are a portion of the full length protein and can assist trophinin in mediating cell adhesion (see Example II). While not necessarily structurally related, trophinin-assisting protein family members are characterized, in part, by having the property of assisting trophinin mediated cell adhesion.

Trophinin and a trophinin-assisting protein can interact directly or indirectly to effect cell adhesion. For example, cell adhesion can be mediated by the direct binding of a trophinin-assisting protein to trophinin. Cell adhesion also can be due to a trophinin-assisting protein binding to another cellular molecule which then directly or indirectly binds to trophinin. Alternatively, a trophinin-assisting protein can interact indirectly with trophinin by binding to and eliminating the function of a negative regulator of trophinin activity in the cell.

A substantially purified trophinin-assisting protein can be obtained, for example, using well known biochemical methods of purification or by expressing a recombinant nucleic acid molecule encoding a trophinin-assisting protein such as the nucleic acid molecules shown in SEQ ID NO: 4, SEQ ID NO: 6 or SEQ ID NO: 8. In addition, an amino acid sequence consisting of at least a portion of the amino acid sequences of SEQ ID NO: 5, SEQ ID NO: 7 or SEQ ID NO: 9 can be chemically synthesized or can be produced by expressing a portion of the nucleotide sequence shown in SEQ ID NO: 4, SEQ ID NO: 6 or SEQ ID NO: 8, respectively.

The complete amino acid sequence of tastin (SEQ ID NO: 5) was deduced from the nucleotide sequence of the tastin cDNA clone and is shown in FIG. 6. The open reading frame of the tastin cDNA encodes a protein having 778 amino acids. Tastin exhibits an apparent molecular mass of about 80 kDa based on SDS-PAGE analysis of in vitro translated tastin cDNA (FIG. 4). This mass is consistent with a molecular weight of 83.75 kDa calculated from the tastin cDNA open reading frame. Tastin lacks a consensus signal sequence characteristic of a secreted protein and contains no transmembrane helices as assessed by hydropathy analysis (Kyte and Doolittle, supra, 1982). Thus, tastin has the characteristics of a cytoplasmic protein.

Tastin is rich in proline residues, which account for 15.3% of the total amino acids of the protein, and in cysteine residues. The majority of the cysteines are located between position 516 to 650 and occur primarily within four tandemly repeated sequences of 33 amino acids each (region denoted by italics in FIG. 6). Tastin contains many serine and threonine residues that are potential sites for phosphorylation, including two potential sites for cAMP/cGMP dependent kinase, sixteen sites for protein kinase C (Kemp and Pearson, supra, 1990), eleven sites for casein kinase II and two sites for MAP kinase (Gonzalez et al., *J. Biol. Chem.* 266:22159–22163 (1991)) (see Example IV).

Tastin has no overall significant homology to previously reported protein sequences. Nucleotide sequence homology analysis of tastin identified the sequence HFBCL29 (Genbank accession number M85643), which was derived from a human fetal brain cDNA library. HFBCL29 shows DNA base complementarity to a portion of tastin cDNA (positions 2057 to 2340). Thus, the HFBCL29 sequence can be homologous to a portion of the tastin sequence if HFBCL29 was recorded in the data base in the antisense direction. The protein sequence deduced from HFBCL29 is related to Y box binding protein-1 (Adams et al., *Nature* 355:632–634 (1992)). However, the entire nucleotide sequence and deduced amino acid sequence of tastin are not homologous overall to the Y-box binding protein-1.

The complete amino acid sequence of bystin was deduced from the nucleotide sequence of the bystin cDNA clone and is shown in FIG. 7 (SEQ ID NO: 7). The open reading frame of the bystin cDNA codes for a protein of 306 residues. Bystin contains threonine and serine residues within potential sites for phosphorylation by protein kinase C (underlined) and casein kinase II (bolded). In addition, bystin contains tyrosine residues (bolded) that are potential sites of phosphorylation by tyrosine kinase and glycine residues within potential sites for myristoylation (bolded). Amino acid residues 1 to 88 of bystin show a significant degree of sequence homology to the bys gene previously identified in Drosophila (Stuart et al., *Mol. Cell. Biol.* 13:2524 (1993)).

A partial amino acid sequence of lastin was deduced from a partial nucleotide sequence of the lastin cDNA clone and is shown in FIG. 8 (SEQ ID NO: 9). The lastin cDNA clone does not contain the 3' end of the gene, including the stop codon and the poly-A tail. The open reading frame of the partial cDNA encodes for 675 amino acids. Lastin contains threonine and serine within potential sites for phosphorylation by protein kinase C (underlined) and casein kinase II (bolded). Lastin also contains potential sites for myristoylation of glycine residues.

The present invention also provides antibodies that are specifically reactive with trophinin or with a trophinin-assisting protein. As used herein, the term "antibody" is used in its broadest sense to include polyclonal and monoclonal antibodies, as well as polypeptide fragments of antibodies that retain a specific binding affinity for trophinin or a trophinin-assisting protein of at least about $1 \times 10^5$ M$^{-1}$. One skilled in the art would know that antibody fragments such as Fab, F(ab')$_2$ and Fv fragments can retain specific binding activity for their target antigen and, thus, are included within the definition of an antibody to trophinin or to a trophinin-assisting protein. In addition, the term "antibody" as used herein includes naturally occurring antibodies as well as non-naturally occurring antibodies such as domain-deleted antibodies (Morrison and Oi, WO 89/07142, Aug. 10, 1989, which is incorporated herein by reference) or single chain Fv (Ladner and Bird, U.S. Pat. No. 5,250,203, Nov. 9, 1993, which is incorporated herein by reference). Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference.

Particularly useful non-naturally occurring antibodies include chimeric antibodies and humanized antibodies. Methods to produce chimeric antibodies and humanized antibodies by the method of CDR grafting are known in the art (see, for example, Winter, U.S. Pat. No. 5,225,539, Jul. 6, 1993, which is incorporated herein by reference).

As used herein, the term "chimeric antibody" means an antibody having a human constant region and a variable region from an organism other than a human. For example, a chimeric antibody useful in the invention can consist of a human IgG constant region and a variable region obtained from a mouse anti-human trophinin antibody. As used herein, the term "humanized antibody" means an antibody having constant and framework regions derived from human and hypervariable regions derived from an organism other than a human. For example, a humanized antibody useful in the invention can consist of the amino acids that form the hypervariable region of a mouse anti-human trophinin antibody and the amino acids that form the framework region and constant regions of a human IgG class antibody.

Chimeric antibodies and humanized antibodies are particularly useful for administration to a human subject, since the likelihood of an immune response by the subject against the antibody is minimized. Other non-naturally occurring antibodies within the present invention include bispecific antibodies, in which the antibody contains at least two different binding specificities that can be univalent or multivalent for each particular binding specificity. Methods for producing bispecific antibodies by chemical crosslinking or by heterohybridoma formation are well known in the art (for trivalent antibodies, see, for example, Ahlem and Huang, U.S. Pat. No. 5,273,743, Dec. 28, 1993), which is incorporated herein by reference).

An anti-trophinin antibody or an anti-trophinin-assisting protein antibody can be prepared using substantially purified trophinin or a trophinin-assisting protein, respectively, either of which can be obtained from natural sources or produced by recombinant DNA methods or chemical synthesis. For example, recombinant DNA methods can be used to express trophinin alone or as a fusion protein, which can facilitate purification of the antigen and enhance its immunogenicity (see Example II). Similarly, an active fragment of trophinin or of a trophinin-assisting protein also can be obtained as described above and can be used as an immunogen (see Example V). If not sufficiently immunogenic, such fragments or peptides can be made immunogenic by expressing the hapten as a fusion protein or by coupling the hapten to a immunogenic carrier molecule such as bovine serum albumin or keyhole limpet hemocyanin (KLH). Various other carrier molecules and methods for coupling a non-immunogenic peptide to a carrier molecule are well known in the art (see, for example, Harlow and Lane, *Antibodies: A laboratory Manual* Cold Spring Harbor Laboratory Press, (1988), which is incorporated herein by reference). Methods for raising an antibody are routine and described, for example, by Harlow and Lane (supra, 1988).

An antiserum containing polyclonal antibodies to trophinin or to a trophinin-assisting protein can be raised in rabbits, goats or other animals. The resulting antiserum can be processed by purification of an IgG antibody fraction using protein A Sepharose chromatography and, if desired, can be further purified by affinity chromatography using, for example, Sepharose conjugated with a peptide antigen (see Example V). The ability of polyclonal antibodies to specifically bind to a given molecule can be manipulated, for example, by dilution or by adsorption to remove crossreacting antibodies to a non-target molecule. Methods to manipulate the specificity of polyclonal antibodies are well known to those in the art (See Harlow and Lane, supra, 1988).

A monoclonal anti-trophinin or anti-trophinin-assisting protein antibody can be produced using known methods (Harlow and Lane, supra, 1988). Essentially, spleen cells from a trophinin- or a trophinin-assisting protein-immunized animal can be fused to an appropriate myeloma cell line such as SP2/0 myeloma cells to produce hybridoma cells. Cloned hybridoma cell lines can be screened using a labeled trophinin or trophinin-assisting protein polypeptide to identify clones that secrete an appropriate monoclonal antibody. A trophinin or a trophinin-assisting protein polypeptide can be labeled as described below. A hybridoma that expresses an antibody having a desirable specificity and affinity can be isolated and utilized as a continuous source of monoclonal antibodies. Methods for identifying an anti-trophinin or anti-trophinin-assisting protein antibody having an appropriate specificity and affinity and, therefore, useful in the invention are known in the art and include, for example, enzyme-linked immunoadsorbance assays, radioimmunoassays, precipitin assays and immunohistochemical analyses (see for example, Harlow and Lane, supra, 1988; chap. 14).

Figure 1C:
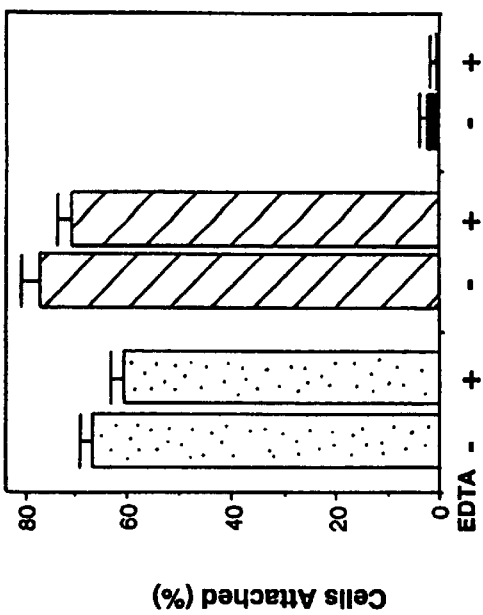
Figure 1D:
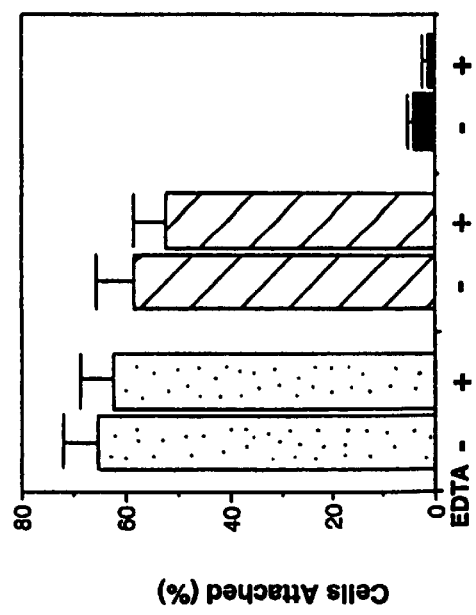

An anti-trophinin antibody can be characterized by its ability to bind a portion of a mammalian trophinin protein, such as the portion of trophinin that is exposed on the external side of the plasma membrane of a cell (see, for example, FIG. 1D). An anti-trophinin-assisting protein antibody can be characterized by its ability to bind to an epitope that is unique to one or more members of the trophinin-assisting protein family of proteins.

An anti-trophinin antibody or an anti-trophinin-assisting protein antibody of the invention can be useful to purify trophinin or a trophinin-assisting protein, respectively, from a sample. For example, an anti-trophinin antibody can be attached to a solid substrate such as a resin and can be used to affinity purify trophinin. In addition, an anti-trophinin antibody can be used to identify the presence of trophinin in a sample. In this case, the antibody can be labeled with a detectable moiety such as a radioisotope, an enzyme, a fluorochrome or biotin. An anti-trophinin or anti-trophinin-assisting protein antibody can be detectably labeled using methods well known in the art (see, for example, Harlow and Lane, supra, (1988); chap. 9). Following contact of a labeled antibody with a sample such as a tissue homogenate or a histological section of a tissue, specifically bound labeled antibody can be identified by detecting the labeled moiety.

A labeled second antibody also can be used to identify specific binding of an unlabeled anti-trophinin or anti-trophinin-assisting protein antibody. A second antibody generally will be specific for the particular class of the first antibody. For example, if an anti-trophinin antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, then the sample is contacted with the labeled second antibody, which specifically binds to the first antibody and results in a labeled sample. Alternatively, a labeled second antibody can be one that reacts with a chemical moiety, for example biotin or a hapten that has been conjugated to the first antibody (see for example, Harlow and Lane, supra (1988); chapter 9).

The present invention also provides nucleic acid molecules encoding trophinin or a trophinin-assisting protein. Nucleic acid molecules encoding the disclosed proteins, which are involved in mediating apical cell adhesion, were obtained by functional selection from an expression cDNA library (see Example II). Essentially, a cDNA library was prepared from HT-H cells and transfected into non-adhering COS-1 cells, which then were selected for adherence to SNG-M cells. Both trophinin and trophinin-assisting protein clones were simultaneously discovered since COS-1 cells only became adherent following co-transfection with a trophinin and a trophinin-assisting protein cDNA sequence (see FIG. 1C).

The present invention provides a substantially purified nucleic acid molecule encoding a mammalian trophinin. For example, the invention provides a substantially purified nucleic acid molecule encoding human trophinin having substantially the nucleotide sequence shown in FIG. 3 (SEQ ID NO: 1). As used herein, the term "substantially purified" means that the nucleic acid is relatively free from contaminating materials such as lipids, proteins, carbohydrates or cellular material normally associated with a nucleic acid in a cell. For example, a nucleic acid molecule that is chemically synthesized is considered substantially purified. Recombinant DNA methods for producing a substantially purified nucleic acid are well known in the art and include cloning a sequence or polymerase chain reaction (PCR) amplification of a sequence (see Sambrook et al., *Molecular Cloning: A laboratory manual* (Cold Spring Harbor Laboratory Press 1989), which is incorporated herein by reference; see, also, Erlich, *PCR Technology: Principles and applications for DNA amplification* (Stockton Press 1989), which is incorporated herein by reference). As used herein, the term "substantially the nucleotide sequence" means a sequence that contains, for example, different nucleotides than shown in FIG. 3 (SEQ ID NO: 1) but that, as a result of the degeneracy of the genetic code, encodes substantially the same amino acid sequence as shown in FIG. 3 (SEQ ID NO: 2). Such nucleotide sequences can be either DNA or RNA and can encode either the coding or non-coding nucleotide strand.

The cloned nucleic acid molecule encoding trophinin (SEQ ID NO: 1) contains 2524 nucleotides with an open reading frame encoding 749 amino acids (see FIG. 3). The 3' untranslated region of trophinin consists of 250 nucleotides and contains a polyadenylation signal located twelve nucleotides upstream of the poly-A tail. Among the ATG codons in the 5' region, the sequence around the ATG at position 1 (see FIG. 3) closely matches a Kozak sequence optimal for translation initiation (Kozak, *Nucleic Acid Res.* 12, 857–872, (1984)). No other ATG codon near the 5' end conforms to the consensus sequence for translation initiation. In vitro translation of the trophinin cDNA confirms that the ATG beginning at position 1 in FIG. 3 encodes the initiation methionine in trophinin.

The invention also provides a nucleotide sequence that can hybridize to a portion of the nucleic acid molecule encoding trophinin under relatively stringent hybridization conditions. Relatively stringent hybridization conditions can be determined empirically or can be estimated based, for example, on the relative GC:AT content of the hybridizing nucleotide sequence and the target sequence, the length of the hybridizing nucleotide sequence and the number, if any, of mismatches between the hybridizing nucleotide sequence and the target sequence. The extent of hybridization can be controlled, for example, by the temperature, pH or ionic strength of the hybridization reaction mixture or the subsequent wash solutions (Sambrook et al., supra, 1989).

A nucleotide sequence useful for hybridizing to a nucleic acid molecule encoding trophinin should be at least ten nucleotides in length and can be prepared, for example, by restriction endonuclease digestion of a cloned nucleic acid molecule, such as the nucleic acid molecule shown in FIG. 3 (SEQ ID NO: 1), by PCR amplification of a portion of a nucleic acid encoding trophinin or by chemical synthesis using well known methods. A nucleotide sequence can be labeled with a detectable moiety and can be used as a probe to detect a nucleic acid molecule or as a primer for PCR. Methods for detectably labeling a nucleic acid are well known in the art (see, for example, Sambrook et al., supra, 1989; see, also, Ausubel et al., *Current Protocols in Molecular Biology* (John Wiley & Sons 1987), which is incorporated herein by reference).

The invention also provides a substantially purified nucleic acid molecule encoding a trophinin-assisting protein. For example, the invention provides a substantially purified nucleic acid molecule encoding human tastin, bystin or lastin having substantially the nucleotide sequence shown in FIG. 6 (SEQ ID NO: 4), FIG. 7 (SEQ ID NO: 6) and FIG. 8 (SEQ ID NO: 8), respectively.

The nucleic acid molecule encoding tastin (SEQ ID NO: 4) contains 2,577 nucleotides having an open reading frame encoding 778 amino acids (see FIG. 6). The 3' untranslated region contains 133 nucleotides and has a polyadenylation signal located eleven nucleotides upstream of the poly-A tail. The nucleotide sequence around the ATG at position 1 conforms to the consensus sequence for the translation initiation site (Kozak, supra, 1984). In vitro translation of the tastin cDNA confirms that the ATG beginning at position 1 in FIG. 6 encodes the initiation methionine in tastin.

The nucleic acid molecule encoding bystin (SEQ ID NO: 6) contains 1,293 nucleotides having an open reading frame encoding 306 amino acids (see FIG. 7). The 3' untranslated region consists of 306 nucleotides.

The nucleic acid molecule encoding lastin is based on the sequence of a partial cDNA clone (SEQ ID NO: 8) that contains 2,223 nucleotides having an open reading frame encoding 675 amino acids beginning at the ATG start site (see FIG. 8). The 5' untranslated region consists of 198 nucleotides. The nucleotide sequence around the ATG at position 1 conforms to the consensus sequence for the translation initiation site (Kozak, supra, 1984).

The invention also provides a nucleotide sequence encoding a trophinin-assisting protein that can hybridize to a nucleic acid molecule under relatively stringent hybridization conditions. A nucleotide sequence encoding a trophinin-assisting protein should be at least ten nucleotides in length and can be prepared as described above.

The invention provides vectors containing a nucleic acid molecule encoding a mammalian trophinin or a mammalian trophinin-assisting protein and host cells containing the vectors. Vectors are well known in the art and include, for example, cloning vectors and expression vectors, as well as plasmids or viral vectors (see, for example, Goedell, *Methods in Enzymology*, vol. 185 (Academic Press 1990), which is incorporated herein by reference). For example, an expression vector that contains a nucleic acid molecule encoding trophinin can be particularly useful for expressing large amounts of trophinin protein, which can be purified and used as an immunogen to raise anti-trophinin antibodies. A baculovirus vector is an example of a vector that can be used to express large amounts of trophinin or a trophinin-assisting protein. A vector containing a nucleic acid molecule encoding a trophinin or a trophinin-assisting protein can also contain a promoter or enhancer element, which can be constitutive or inducible and, if desired, can be tissue specific. Host cells also are known in the art and can be selected based on the particular vector. An appropriate host cell can be selected based, on the particular vector used, for example, baculovirus transfer vectors can be used with baculovirus DNA to infect insect cell lines such as SF21 cells.

An expression vector can also be used to effect the ability of cells to undergo trophinin-mediated cell adhesion. A variety of nucleic acid molecules can be used to effect cell adhesion under various situations. For example, an expression vector that contains a nucleic acid molecule encoding trophinin can be introduced into a cell that previously expressed an insufficient level of trophinin to mediate cell adhesion. Under the appropriate conditions, cells containing such expression vectors can increase their expression of trophinin, thus enhancing their ability to undergo trophinin mediated cell adhesion. In addition, an expression vector containing a nucleic acid molecule encoding a trophinin-assisting protein can be used to increase trophinin-mediated cell adhesion by introducing the expression vector into cells that fail to exhibit trophinin-mediated cell adhesion due to a deficiency in the expression of a trophinin-assisting protein.

An expression vector also can contain an exogenous nucleic acid molecule encoding an antisense nucleotide sequence that is complementary to a nucleotide sequence encoding a portion of trophinin. When introduced into a cell under the appropriate conditions, such an expression vector can produce the antisense nucleic acid molecule, which can selectively hybridize to the trophinin gene or to an RNA molecule encoding trophinin in a cell and, thereby, affect trophinin expression in the cell. For example, the antisense nucleic acid molecule can hybridize to a trophinin gene in the cell and can reduce or inhibit transcription of the trophinin gene. Also, the antisense molecule can hybridize to the an RNA molecule encoding trophinin in the cell and can reduce or inhibit translation, processing and cell stability or half-life of the RNA.

Expression vectors also can be used to effect trophinin-mediated cell adhesion by introducing into a cell an exogenous nucleic acid molecule encoding a ribozyme that can specifically cleave RNA encoding trophinin. Introducing an expression vector into a cell and expressing a ribozyme specific for an RNA encoding trophinin can reduce or inhibit trophinin expression. An antisense nucleic acid molecule or a ribozyme can be chemically synthesized and incorporated into an expression vector using recombinant DNA techniques. An antisense nucleic acid molecule or a ribozyme also can be added directly to a cell without having been incorporated into the expression vector.

The above described methods for effecting trophinin-mediated cell adhesion by using an expression vector to obtain expression of an exogenous nucleic acid molecule in a cell also can be accomplished if the exogenous nucleic acid molecule encodes a trophinin-assisting protein or an antisense or ribozyme sequence specific for a trophinin-assisting protein. For example, an increase in trophinin-mediated cell adhesion can be achieved by introducing an expression vector encoding a trophinin-assisting protein into cells that are deficient in trophinin-assisting protein expression or produce a non-functional trophinin-assisting protein. In addition, a decrease in trophinin-mediated cell adhesion can be accomplished by introducing into a cell an expression vector that encodes for an antisense or ribozyme specific for a trophinin-assisting protein. In such cases the expressed antisense or ribozyme can reduce or inhibit trophinin-mediated cell adhesion by decreasing the effective level of trophinin-assisting protein in a cell below that required to effect trophinin-mediated cell adhesion.

The ability of cells to undergo trophinin-mediated cell adhesion also can-be effected by introducing two or more expression vectors into a cell, each encoding a different exogenous nucleic acid molecule or introducing an expression vector capable of expressing more than one exogenous nucleic acid molecule. To reduce or inhibit the level of expression of trophinin, for example, expression vectors coding for both an antisense and a ribozyme specific for trophinin can be introduced into a cell. The expression of both such exogenous nucleic acid sequences simultaneously in a cell can be more effective at reducing trophinin expression than when either sequence is expressed alone.

Methods for introducing expression vectors into cells are well known in the art. Such methods are described in Sambrook et al supra (1989) and in Kriegler M. *Gene Transfer and Expression: A Laboratory Manual* (W. H. Freeman and Co. New York N.Y. (1990), which is incorporated herein by reference) and, include, for example, transfection methods such as calcium phosphate, electroporation or lipofection, or viral infection.

Recombinant viral vectors are available for introducing exogenous nucleic acid molecules into mammalian cells and include, for example, adenovirus, herpesvirus and retrovirus-derived vectors. For example, a viral vector encoding trophinin or a trophinin-assisting protein can be packaged into a virus to enable delivery of the genetic information and expression of these proteins in endometrial cells following infection by the virus. Also, a recombinant virus which contains an antisense sequence or a ribozyme specific for a nucleotide sequence encoding trophinin or a trophinin-assisting protein can be used to reduce or inhibit the ability of trophinin to mediate cell adhesion in cells infected by the virus.

Recombinant viral infection can be more selective than direct DNA delivery due to the natural ability of viruses to infect specific cell types. This natural ability for selective viral infection can be exploited to limit infection to specific cell types within a mixed cell population. For example, adenoviruses can be used to restrict viral infection principally to cells of epithelial origin. In addition, a retrovirus can be modified by recombinant DNA techniques to enable expression of a unique receptor or ligand that provides further specificity to viral gene delivery. Retroviral delivery systems can also provide high infection rates, stable genetic integration, and high levels of exogenous gene expression.

As described above, recombinant viral delivery systems exist that provide the means to deliver genetic information into a selected type of cell. The choice of viral system will depend on the desired cell type to be targeted, while the choice of vector will depend on the intended application. Recombinant viral vectors are readily available to those in the art and can be easily modified by one skilled in the art using standard recombinant DNA methods.

The invention also provides methods to detect trophinin or a nucleic acid molecule encoding trophinin in a sample using an agent that specifically binds to trophinin or to a nucleic acid molecule encoding trophinin. As used herein the term "agent" means a chemical or biological molecule that can specifically bind to trophinin or to a trophinin-assisting protein or to a nucleic acid molecule encoding trophinin or a trophinin-assisting protein. For example, an agent specific for trophinin can be another trophinin molecule or can be an anti-trophinin antibody. In addition, an agent can be a nucleotide sequence that binds to a nucleic acid molecule encoding trophinin or a trophinin-assisting protein.

As used herein, "sample" means a specimen such as a cell, tissue or an organ, which can be obtained, for example, by biopsy from a subject or can be a serum, urine or mucin specimen obtained from a subject. A sample containing trophinin can be used directly or can be processed prior to testing. For example, a biopsy tissue sample can be cut into tissue sections for histologic examination or can be further processed to release trophinin from cells within the tissue. Methods to process a sample such as a tissue, cells or a biological fluid for detecting a protein are known in the art (see, for example, Harlow and Lane, supra, (1988)).

The presence of trophinin in a sample can be determined by contacting the sample with an agent that can bind to trophinin under suitable conditions, which allow the agent to specifically bind to trophinin. Suitable conditions can be achieved using well known methods and can be optimized, for example, by varying the concentration of reactants or the temperature of the reaction. After the agent specifically binds to trophinin in a sample, the presence of trophinin can be determined by detecting specific binding of the agent.

An agent that can be detectably labelled can be used as a probe. For example, a probe for detecting the presence of trophinin in a sample can be an anti-trophinin antibody that is detectably labelled or that can be bound by a second antibody that is detectably labelled. In addition, a probe for detecting a nucleic acid molecule encoding trophinin or a trophinin-assisting protein can be an agent such as a nucleotide sequence that can hybridize to the nucleic acid molecule and that can be detected directly, for example, by a radioactive moiety incorporated into the nucleotide sequence, or indirectly, for example, by PCR analysis.

As used herein, "detectable label" means a molecule whose presence can be detected due to a physical, chemical or biological characteristic of the molecule. Detectable labels include, for example, radioisotopes, fluorescent molecules, enzyme/substrate systems, or visually detectable molecules. Methods to produce a probe for detecting a protein are well known in the art (see, for example, Harlow and Lane, supra, (1988)) and include, for example labelling the agent with a radioisotope, fluorescence molecule or histochemically useful enzyme or visible particle or colloid. Methods to produce a probe for detecting a nucleic acid molecule are also well known in the art (see, for example, Sambrook et al, supra, 1989; Hames and Higgins, *Nucleic acid Hybridization: a Practical approach,* IRL press, New York, (1985), which are incorporated herein by reference).

An agent often can bind to a limited but detectable level of non-target substances such as the assay container and can result in background binding. Thus, to properly conclude that the presence of an agent binding in a sample represents the presence of trophinin, it is necessary to determine that the specific binding observed in a sample is greater than the background binding of the agent. The level of background binding of an agent can be determined using a control sample, which is similar in composition to the sample being tested but which contains a defined amount of trophinin or no trophinin.

The invention also provides methods to detect a trophinin-assisting protein in a sample using an agent that specifically binds to a trophinin-assisting protein. Such an agent can be an anti-trophinin-assisting protein antibody that specifically binds to a particular trophinin-assisting protein such as tastin, bystin and lastin. The presence of a trophinin-assisting protein in a sample can be determined using the methods described above.

A nucleic acid molecule encoding trophinin can be detected in a sample using an agent such an antisense nucleotide sequence that is specific for trophinin as described above. The target nucleic acid molecule can be extracted from a sample by methods well known in the art (See Sambrook et al., supra, 1989). Methods to detect the presence of a particular nucleic acid molecule within a population of nucleic acid molecules are well known to those in the art and include, for example, Southern blotting, northern blotting, slot blotting and PCR amplification (see, for example, Sambrook et al., supra, 1989). In situ hybridization also can be particularly useful for identifying nucleic acids in a sample (see for example, Pardue, in *Nucleic Acid Hybridisation: a practical approach* (IRL Press, 1991), which is incorporated herein by reference).

To detect a nucleic acid molecule encoding trophinin in a sample, the sample is contacted with a nucleotide sequence probe that can hybridize to a nucleic acid molecule encoding trophinin under relatively stringent conditions. The presence of a nucleic acid molecule encoding trophinin in the sample can be determined, for example, by detecting the presence of a specifically bound nucleotide sequence probe. The degree of background binding of the probe also can be determined in a control sample to confirm that binding seen in the sample is due to the presence of the target nucleic acid molecule.

A nucleic acid molecule encoding a trophinin-assisting protein also can be detected in a sample using methods as described above. For this purpose, the agent can be a nucleotide sequence specific for a nucleic acid molecule encoding a single trophinin-assisting protein such as tastin. The target nucleic acid molecule can be extracted from the sample or can- be directly detected by in situ hybridization.

A combination of both protein detecting and nucleic acid detecting methods, when used together, can provide more information than either method used alone. For example, when the expression of RNA encoding trophinin and tastin was evaluated in samples of human tissues by northern blotting, low levels of trophinin mRNA and tastin mRNA were observed in placenta, lung and liver. However, immunofluorescence analysis of these tissues using anti-trophinin antibodies and anti-tastin antibodies was negative for these tissues except for macrophages present in the tissues (not shown). Thus, the combination of nucleic acid hybridization and immunofluorescence techniques together demonstrated that trophinin and tastin are not expressed by the majority of cell types within the body but are expressed by macrophages which are resident in certain tissues.

The expression of trophinin in vivo indicates that trophinin has a role in human embryo implantation. For example, immunofluorescence studies using anti-trophinin antibodies demonstrated that trophinin was absent in term placental tissues. Although trophinin was absent from the majority of placental tissues from early (7–10 week) pregnancy (except for macrophages), trophinin was readily detected in focal regions in the apical plasma membranes of syncytiotrophoblasts of chorionic villi at 7 weeks pregnancy (FIG. 10A). Trophinins also were found in cytoplasmic vesicles of syncytiotrophoblasts in the chorionic villi from 7–10 week pregnancy (FIG. 10B). Double immunostaining with the lamp-1 lysosome marker (Fukuda, *J. Biol. Chem.* 266:21327–21330 (1991), which is incorporated herein by reference) showed co-localization of trophinin and lamp-1 in these vesicles, indicating that trophinins are present in lysosomes or endosomes. These results indicate that trophinin expression is strictly regulated in vivo and is present on the surface of syncytiotrophoblasts at early stages of pregnancy but not at later stages of pregnancy. Trophinins that are present in lysosomes of syncytiotrophoblasts at later stages of pregnancy can be undergoing degradation following removal from the cell surface. Tastin was not detected in most of the chorionic villi from 7–10 week pregnancy, except that a weak signal was observed in the lysosomes of the syncytiotrophoblasts.

In addition to expression by the embryo, trophinin also is expressed in the uterus at the apical plasma membrane of the surface epithelium on day 16/17 endometrium (FIG. 10C), but not in endometrium during the proliferation stage (day 6–13) or ovulation stage (day 14). Endometrial biopsy samples taken from the late secretory phase (day 20–28) showed staining for trophinin in the mucin. Tastin could not be detected in any of the above endometrial samples except for mucin. These results, like those for the embryo, demonstrate that trophinin expression is strictly regulated in endometrial tissue and is present for only a short time on the cell surface. The expression of trophinin is consistent with the concept of an implantation window for embryo implantation (Yoshinaga, *Biochem. Biophys. Res. Comm.* 181:1004–1009 (1988); Harper, *Ballieres Clin. Obstet. Gynaecol.* 6:351–371 (1992)).

The level of trophinin or of a trophinin-assisting protein in a sample of endometrial tissue can be diagnostic of infertility due to failure of implantation. For example, insufficient expression of trophinin in endometrial epithelial cells or in trophoblast cells of the embryo can result in a failure of implantation. As described above, agents to detect trophinin or a trophinin-assisting protein can be used to detect the level of these proteins or can be used to detect the level of nucleic acid molecules encoding these proteins at various times during the menstrual cycle. For example, immunofluorescence staining with anti-trophinin antibodies showed that trophinin was present in mucin shed from endometrial epithelium of late secretory phases (day 20–28; see FIG. 10D). With implantation of the embryo, mucin shedding from the endometrial epithelium does not occur. Thus, the disclosed methods to detect trophinin are useful for testing for the absence of pregnancy since detection of trophinin shed into body fluids, for example, in cervical mucus or in serum, can provide an early indication that implantation had not occurred and therefore, that the individual was not pregnant.

Figure 2A:
FIGS. 2A, 2B, 2C and 2D are electron micrographs showing the interface between adherent HT-H and SNG-M cells. HT-H cells were added to a monolayer of SNG-M cells and electron micrographs were taken after 10 min, 6 hr or 4 days of culture.
Figure 2B:
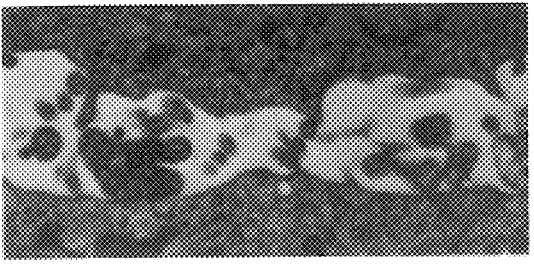
Figure 2C:
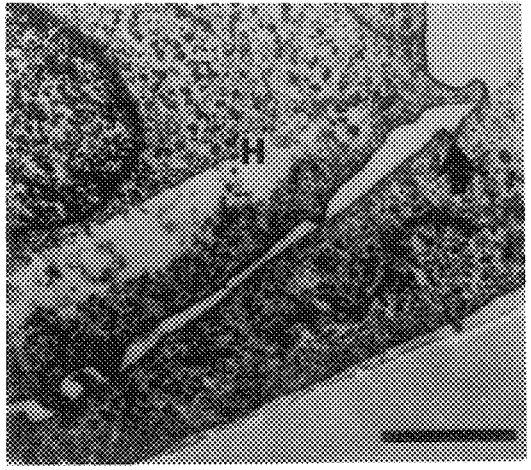
Figure 2D:
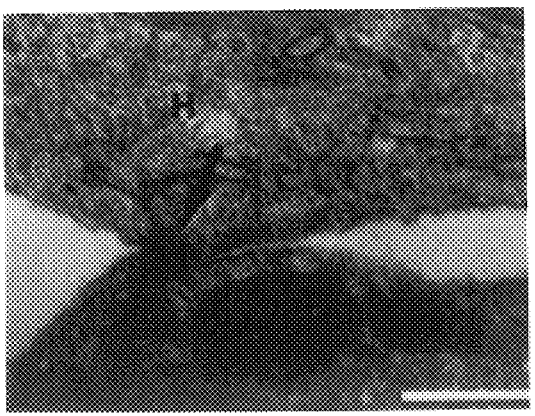

The ability to adhere cells at their apical surfaces using the methods described in the present invention can have a significant effect on cell morphology and function as exemplified by adhesion of HT-H cells to SNG-M cells. Initial cell attachment of HT-H to SNG-M cells is associated with the extension of the microvilli from one cell to another (FIGS. 2A and 2B). Within 6 hr after co-culture, each microvillus becomes flattened into the plasma membrane (FIG. 2C) and adherent junctions appear after 20 hr of co-culture (not shown). Desmosomes are formed between HT-H and SNG-M cells at sites in the plasma membrane that were originally the upper (apical) surface of these cells (FIG. 2D). This finding contrasts to the situation in typical epithelial cells where desmosomes normally form in plasma membranes located at the lateral or basal sides of the cell. The ability to form desmosomes at a new membrane surface can result from a sequential reorganization of the proteins that control the structure and polarity of epithelial cells.

Figure 9B:
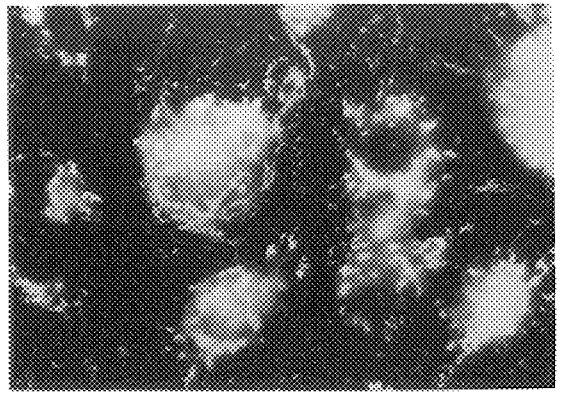

Trophinin is expressed on the surfaces of HT-H and SNG-M cells in a unique lace-like pattern (FIGS. 9A and 9B). This expression indicates that trophinin proteins cluster to form patches in the plasma membrane. Trophinin contains decapeptide repeats that form multiple β-turn structures (see FIGS. 5A and 5B). This unique structure can be responsible for self-aggregation of trophinin in the cell membrane and for mediating cell adhesion. The subcellular localization of tastin in HT-H and SNG-M cells (FIGS. 9C and 9D) indicates that tastin can associate with cytoskeletal elements such as cytokeratins present in these cells. Thus, trophinin-assisting protein's can function to segregate trophinin molecules into clusters on the apical plasma membrane membranes by interacting with trophinin in cells.

Evidence from recent studies on cell adhesion molecules indicates that their function is regulated by association with cytoplasmic proteins and cytoskeletal structures (Gumbiner, *Neuron* 11:551–564 (1993); Stappert and Kemler, *Curr. Olin. Neurol.* 3:60–66 (1993); Garrod, *Curr. Opin. Cell Biol.* 5:30–40 (1993; Hynes, *Cell* 69:11–25 (1992)). Such molecular organization is important for cell-to-cell adhesion and cell movement. Cytoplasmic proteins involved in regulating cell adhesion molecules are associated with kinases that play a role in signal transduction, which occurs upon binding of cell adhesion molecules at the cell surface. Both trophinin and tastin contain serine and threonine residues that can serve as potential phosphorylation sites for protein kinases. For example, the amino terminal region of trophinin contains three serine and threonine residues that are potential phosphorylation sites (FIG. 3). The presence of phosphorylation sites in trophinin and trophinin-assisting proteins indicates that the adhesion of trophinins expressed on one cell to those on another cell can be involved in triggering phosphorylation of trophinin and trophinin-assisting proteins as a signal to initiate the morphological changes occurring subsequent to trophinin-mediated cell adhesion.

The invention provides methods to modify the ability of cells to adhere to each other. Cell adhesion can allow the cells to undergo subsequent physiological changes associated with cell adhesion. Such physiological changes can result from an increase in the adherence between cells due to increasing the level of trophinin expressed on the cell surface. An increase in adherence can be achieved by introducing an exogenous nucleic acid molecule encoding trophinin into cells and allowing the cells to adhere under appropriate conditions (see Example VII). This method of increasing adherence between cells can be used with any cell that can express functional trophinin proteins. Such cells include, for example, cells obtained from human or non-human primates or other mammalian cells, such as bovine, ovine, porcine or murine cells.

A nucleic acid molecule encoding trophinin can be introduced into a population of first cell types, which can be allowed to adhere to each other. In addition, a cell from the population of first cell types, which contain a nucleic acid molecule encoding trophinin, can be combined with a second cell type, wherein a DNA molecule encoding a trophinin binding protein has been introduced into the second cell type. In this case, adhesion between the first cell type and the second cell type can occur due to binding of trophinin on one cell to the trophinin binding protein of the other cell. Similarly, a third or additional cell types expressing trophinin or a trophinin binding protein can be included so as to provide adhesion among three or more cell types. As used herein, the term "trophinin binding protein" means a molecule that can bind to trophinin with an affinity of about $1 \times 10^{-5}$ M or greater as measured, for example, by ELISA. A trophinin binding protein can include, for example, trophinin itself, an anti-trophinin antibody or a trophinin-assisting protein.

Cell types that naturally express trophinin can adhere to a cell type that has been modified to express trophinin (see Example VII). In some cases, the expression of trophinin alone in cells may not enable cell adhesion. In such cases, adhesion may require the expression of a trophinin-assisting protein in addition to trophinin. The present invention also provides nucleic acid molecules encoding members of the trophinin-assisting protein family of proteins as well as methods for introducing such exogenous nucleic acid molecules into cells to obtain expression of a trophinin-assisting protein. This method of increasing adherence between cells by introducing an exogenous nucleic acid molecule can be used with any cell that can express functional trophinin-assisting proteins. Such cells include, for example, human and non-human primates or other mammalian cells, as described above.

The level of expression of trophinin in a cell can be increased on the cell surface by contacting the cell with a trophinin agonist. As used herein, "trophinin agonist" means a chemical or biological molecule such as a simple or complex organic molecule, a peptide, peptido-mimetic, protein, carbohydrate or nucleotide sequence that can increase the expression level of functional trophinin in a cell and, thereby, increase the capacity of the cell for trophinin-mediated cell adhesion. A nucleic acid encoding trophinin is an example of a trophinin agonist. An expression vector that contains an exogenous nucleic acid molecule encoding trophinin can also be used as a trophinin agonist. For example, the introduction of an expression vector encoding trophinin into a cell can result in increased expression of trophinin and increased ability of the cell to undergo trophinin-mediated cell adhesion. Another example of a trophinin agonist can be a trophinin-assisting protein or an expression vector that contains an exogenous nucleic acid molecule encoding a trophinin-assisting protein. For example, a cell that can express trophinin but cannot efficiently mediate cell adhesion can be due to the inability of the cell to express a level of trophinin-assisting protein sufficient to interact with trophinin or a trophinin binding protein. In such cells, a trophinin agonist can, for example, be a trophinin-assisting protein or an expression vector encoding a trophinin-assisting protein.

Particular types of trophinin agonists also can include hormones, cytokines or other types of molecules that interact directly or indirectly, for example, with genetic regulatory elements that control the expression level of trophinin or a trophinin-assisting protein. Genetic regulatory elements include, for example, promoters, enhancers, or intronic sequences that can regulate protein expression at the transcriptional or translational level. For example, a trophinin agonist can increase the expression of trophinin in a cell by binding to the promoter region of a trophinin gene and increase the efficiency of transcription. A trophinin agonist also can increase the expression of trophinin indirectly by binding to a regulatory protein, which, in turn, can activate an enhancer sequence to increase transcription of the trophinin gene.

Trophinin mediated cell adhesion also can be increased by directly contacting a cell with purified trophinin. The ability of cells to adsorb a protein such as trophinin by an active or a passive process can result in a greater level of trophinin available on the cell surface for contact with another cell, thus, increasing the likelihood of trophinin-mediated cell adhesion.

Trophinin agonists, which are useful for increasing trophinin-mediated cell adherence, are useful, for example, for preventing or minimizing the likelihood of implantation failure. Humans or other mammals that exhibit implantation failure can be tested for the level of trophinin or a trophinin-assisting protein expressed by endometrial cells using the methods described herein. Subjects having cells that fail to express sufficient levels of trophinin or trophinin-assisting proteins to achieve trophinin-mediated adhesion or express an aberrant or non-functional form of trophinin or a trophinin-assisting protein can be identified and a trophinin agonist can be used to achieve cell adhesion.

The invention also provides methods to reduce or inhibit trophinin-mediated cell adhesion by contacting a cell with a trophinin antagonist, which can reduce or inhibit trophinin binding. Such methods can be used with human or other mammalian cells that express trophinin. For example, methods to reduce or inhibit trophinin-mediated cell adhesion can be used to block or terminate embryo implantation in humans or other mammals. As used herein, "trophinin antagonist" means a chemical or biological molecule such as a simple or complex organic molecule, a peptide, peptidomimetic, protein, carbohydrate, antibody or nucleotide sequence that can reduce or inhibit the ability of trophinin to mediate cell adhesion.

A trophinin antagonist can act by binding to a trophinin molecule of a first cell and, as a result of such binding, inhibit binding to a trophinin molecule on a second cell. Thus, the binding between two trophinin molecules is reduced or inhibited by the trophinin antagonist to a level below that required for a biological activity. An antibody molecule that binds to portion of trophinin exposed on the external side of the cell membrane is an example of a trophinin antagonist. The present invention provides methods to produce such antibodies (see Example V) and to evaluate such antibodies for their ability to act as trophinin antagonists in an in vitro cell binding assay (see FIG. 1D and Example VII).

An active fragment trophinin antagonist is another example of a trophinin antagonist that can bind to trophinin on a cell and prevent the cell from binding to a second cell that expresses a trophinin binding protein. As used herein, an "active fragment trophinin antagonist" means a portion of trophinin or a trophinin binding protein that cannot mediate cell adhesion but that can bind to a trophinin molecule. Such active fragment trophinin antagonists can be peptides as small as about five amino acids and can be identified, for example, by screening a peptide library (see for example, Ladner et. al., U.S. Pat. No. : 5,223,409, Jun. 29, 1993, which is incorporated herein by reference) to identify peptides that bind to trophinin but do not mediate cell adhesion.

A trophinin antagonist also can interfere with the interaction of a trophinin-assisting protein with trophinin. Thus, a chemical or biological molecule such as a simple or complex organic molecule, a peptide, peptido-mimetic, protein, carbohydrate or nucleotide can be a trophinin antagonist by binding to the site on a trophinin-assisting protein or on a trophinin molecule that is involved in the interaction between a trophinin-assisting protein and trophinin.

A trophinin antagonist need not bind directly to the site in trophinin that binds to another trophinin molecule or the site in trophinin that binds to a trophinin-assisting protein, in order to inhibit cell adhesion. Thus, for example, a trophinin antagonist of sufficient size, when bound to a region in trophinin that is near the trophinin binding site can physically block another trophinin molecule from binding to the site. Also, a trophinin antagonist can bind to trophinin and change the structure of the trophinin binding site rendering it unsuitable for adhesion to another trophinin molecule. Thus, a trophinin antagonist can act like an allosteric inhibitor of an enzyme. A trophinin antagonist can also function to inhibit trophinin-mediated cell adhesion by binding to a trophinin-assisting protein in a cell, thereby inhibiting the ability of the trophinin-assisting protein to assist trophinin in mediating cell adhesion.

A trophinin antagonist also can function by reducing the level of expression of trophinin or a trophinin-assisting protein, thereby reducing or inhibiting cell adhesion. For example, nucleic acid molecules encoding an antisense nucleotide sequence or encoding a ribozyme for a trophinin or a trophinin-assisting protein can be incorporated into vectors and introduced into cells by methods well known to those in the art as described above. The level of trophinin or trophinin-assisting protein expression also can be reduced by treating cells with hormones, cytokines or other type molecules that interact directly or indirectly with genetic regulatory elements controlling the expression level of trophinin or a trophinin-assisting protein in a cell. A trophinin antagonist can effect trophinin-mediated cell adhesion by reducing the level of expression of trophinin in the cell by blocking regulatory elements involved in maintaining expression of trophinin. A trophinin antagonist can also reduce the level of trophinin expression by acting directly or indirectly as a negative regulator.

Reducing or inhibiting adhesion of cells by trophinin-mediated cell adhesion can be useful in vitro or in vivo. In vitro, trophinin antagonists can be identified and compared to each other to determine potency, which can be derived from concentration versus activity curves and can be represented as the concentration of antagonist that achieves 50% inhibition of activity. In vitro potency can be one criterion for selecting trophinin antagonists that can be useful in vivo. The in vitro method for measuring potency is based on the adhesion assay used to discover trophinin and trophinin-assisting protein molecules (see FIG. 1C and Example I). In this method, a radiolabeled cell line expressing trophinin and a trophinin-assisting protein (e.g. HT-H cells) is contacted with the antagonist to be tested, then the mixture is added to a paraformaldehyde fixed-monolayer of trophinin and trophinin-assisting protein expressing cells (e.g. SNG-M cells). After a period of time, the unbound cells are removed by washing and the percentage of attached cells determined by counting the bound radioactivity. A potent trophinin antagonist can be identified by its ability to significantly reduce or to inhibit trophinin-mediated cell adhesion.

The ability of trophinin to mediate cell adhesion can have other in vitro uses besides that of a trophinin antagonist. For example, trophinin can be used to bind trophinin-expressing cells to a solid support, which is useful, for example, to purify a population of trophinin expressing cells from a mixed population containing trophinin expressing and non-trophinin expressing cells or to purify a trophinin expressing embryo. Also, trophinin attached to a prosthetic devise can be used to bind a layer of trophinin expressing cells to the devise to render the devise more suitable for introduction in vivo.

Trophinin can be bound to a solid support using methods known in the art (for example see Harlow and Lane, supra, (1988)). For example, purified trophinin in PBS (phosphate buffer saline, 10 mM phosphate buffer, pH 7.4) can be directly adsorbed to a plastic tissue culture surface, a polyvinyl chloride surface or a nitrocellulose surface. Trophinin also can be covalently coupled to beads such as, for example, agarose or polyacrylamide that had been previously activated by a coupling agent such as glutaraldehyde or cyanogen bromide. In addition, trophinin can be attached indirectly to a solid support, for example, by first coating or coupling an agent that can specifically bind to trophinin.

A population of trophinin-expressing cells can be enriched from a mixed population of trophinin-expressing and cells that do not express trophinin by applying the mixed cell population to a solid support or surface containing trophinin. After a period of time sufficient to allow the trophinin-expressing cells to adhere to the solid support, cells that do not express trophinin can be washed from the support. The enriched population of trophinin expressing cells can be used directly on the solid support or can be removed from the solid support by vigorous washing or by treating the cells with a trophinin antagonist.

A trophinin antagonist or agonist can be used to prepare a medicament for the treatment of a condition such as infertility, for treatment of a disease or for intervening in a potential pregnancy. For example, a trophinin antagonist can be administered to a subject to block embryo implantation following fertilization by inhibiting binding of the embryo trophoblast cell layer to the uterine epithelial cell layer. A trophinin antagonist also can be used to terminate implantation after it has already occurred by administering a trophinin antagonist to effect detachment of the embryo from the uterine cell lining. In contrast, a trophinin agonist can be administered to a subject to alleviate implantation failure by enhancing the binding between the trophoblast cell layer of the embryo and the endothelial cell layer of the uterus. Trophinin antagonists and agonists of the invention are particularly useful when administered as a pharmaceutical composition containing the trophinin antagonist or agonist and a pharmaceutically acceptable carrier. Pharmaceutically acceptable carriers are well known in the art and include, for example, aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of a trophinin antagonist or agonist. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition.

One skilled in the art would know that a pharmaceutical composition containing a trophinin antagonist or agonist can be administered to a subject by various routes including, for example, by intra-uterine instillation, orally or parenterally, such as intravenously, intramuscularly, subcutaneously or intraperitoneally. The composition can be administered by injection or by intubation. The pharmaceutical composition also can be incorporated, if desired, into liposomes or microspheres or can be microencapsulated in other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively easy to make and administer.

In order to inhibit embryo implantation, the trophinin antagonist is administered in an effective amount, which is about 0.01 to 100 mg/kg body weight. As used herein, the term "effective amount" means the amount of trophinin antagonist that can effectively block a cell adhesion event. For example in the case of implantation, an effective amount is that which blocks embryo implantation. In the case of a trophinin agonist, the "effective amount" means the amount of agonist that can effectively increase level of trophinin-mediated cell adhesion. For example, in implantation failure, an effective amount of a trophinin agonist is the amount that allows for successful implantation. An effective amount of a trophinin antagonist or agonist in a subject can be determined using methods known to those in the art.

The total effective amount can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of trophinin antagonist or agonist required to obtain an effective dose in a subject depends on many factors including the age and general health of the subject as well as the route of administration and the number of treatments to be administered and the chemical form of the antagonist or agonist. In view of these factors, the skilled artisan would adjust the particular amount so as to obtain an effective amount for the subject being treated.

The cadherin and integrin families of adhesion molecules, which are involved in cell-cell and cell-matrix adhesion, are implicated in epithelial differentiation, carcinogenesis and metastasis. A further understanding of how such adhesion receptors exert their biological effects on the cell was accomplished through the discovery of a cell adhesion regulator gene (Pullman and Bodmer, *Nature* 356:529–533 (1992)). The cell adhesion regulator gene codes for a protein that is located in the cytoplasm and functions as a signal transduction molecule for integrin adhesion receptors. The cell adhesion receptor gene has the characteristics of a tumor suppressor gene because inactivation of the gene can result in loss of differentiation induction of a cell and subsequent acquisition of invasive and metastatic character. The genes encoding the trophinin-assisting proteins of the present invention also can function as tumor suppressor genes. For example, the structural features of the trophinin-assisting proteins, as derived from the deduced amino acid sequences (see SEQ ID NO: 5, SEQ ID NO: 7 and SEQ ID NO: 9), are consistent with a cytoplasmic regulatory protein that can mediate intracellular signalling of trophinin or other cell adhesion molecules.

The present invention provides methods to increase the level of expression of trophinin-assisting proteins, thus increasing the tumor suppressor activity of a cell. Such methods can, for example, be useful for the treatment of cancer. As used herein, a trophinin-assisting protein agonist means a chemical or biological molecule such as a simple or complex organic molecule, a peptide, peptido-mimetic, protein, carbohydrate or nucleotide sequence that can increase the expression level of a trophinin-assisting protein in a cell. Particular types of trophinin-assisting protein agonists can include hormones, cytokines or other types of molecules that interact either directly or indirectly with genetic regulatory elements controlling the expression level of a trophinin-assisting protein.

The following examples are intended to illustrate but not limit the present invention.

EXAMPLE I

CELL CULTURE ADHESION METHOD

This example describes methods for performing cell adhesion assays and for evaluating their specificity and impact on cell morphology.

A. Cell Lines

The human teratocarcinoma cell line HT-H was used as a source of embryonic trophoblast cells for the adhesion assay. HT-H cells (Izhar et al., *Biol.* 116:510–518 (1986), which is incorporated herein by reference) were maintained in RPMI 1640 medium containing 10% fetal bovine serum, 2 mM glutamine, 100 units/ml penicillin and 100 μg/ml streptomycin. Trophoblastic HT-H cells were separated from undifferentiated HT-H cells as described (Izhar et al., supra, 1986) and subcloned for use in the experiments described. The endometrial adenocarcinoma cell line SNG-M (Ishiwata et al., *Cancer Res.* 37:1777–1785 (1977), which is incorporated herein by reference) was maintained in RPMI medium as described above. Endometrial adenocarcinoma cell lines Hec1A, RL95-2 AN3CA and KLE were obtained from American Type Culture Collection (Rockville Md.) and were cultured in Dulbecco's modified Eagle's (DME) medium containing 10% fetal bovine serum, 2 mM glutamine, 100 units/ml penicillin and 100 μg/ml streptomycin. Additional epithelial cells which were tested included COS-1 cells (monkey kidney), HeLa (uterine cervical carcinoma), HepG2 (hepatocellular carcinoma), SW480 (colonic adenocarcinoma), and A431 (epidermoid carcinoma). These cells were obtained from the American Type Culture Collection and were cultured as described above.

B. Cell Adhesion Assay

The adhesion of HT-H cells to several different human endometrial epithelial cells was examined. HT-H cells were metabolically labeled with $^{35}$S-methionine using Trans-label (DuPont/NEN, Boston Mass.) in methionine- and cysteine-free RPMI medium supplemented with 10% dialyzed fetal bovine serum, 2 mM glutamine, 100 μg/ml pyruvate, 100 units/ml penicillin and 100 μg/ml streptomycin. Cells were labeled at 37° C. in a humidified $CO_2$ incubator. After 20 minutes (min), the medium was replaced with complete medium and cells were incubated an additional 2 hr.

The $^{35}$S-labeled HT-H cells were detached from the tissue culture dish using cell dissociation solution (Specialty Media, Lavalette, N.J.) supplemented with 1 mM EDTA. The cells were pelleted by centrifugation and resuspended in Hank's balanced salt solution (HBS). Cell suspensions (0.2 ml, 5×10$^4$ cells) were added to a monolayer of endometrial epithelial cells grown in a 24 well tissue culture plate. HT-H cells that did not adhere to the monolayer were removed by washing 3× with HBS with or without 1 mM EDTA. The cells remaining in each well were solubilized with 0.5 ml of 0.5 N NaOH and 1% SDS. The lysate was transferred to a scintillation vial and radioactivity was counted. The data were expressed as % radioactivity remaining on the monolayer relative to the total radioactivity of $^{35}$S-labeled HT-H cells added. The results were obtained from triplicate cultures.

The results of the cell adhesion assays indicate that HT-H cells attached to the SNG-M, Hec1A, KLE and RL95-2 cells, but attached minimally to the AN3CA cells (Table 1). The addition of 1 mM EDTA did not change significantly the percentage of HT-H cells which bound to SNG-M, Hec1A and KLE cells (Table 1), whereas, the attachment of HT-H cells to RF95-2 cells was reduced significantly in the presence of EDTA. These results indicate that adhesion of HT-H cells with SNG-M, Hec1A or KLE cells is divalent cation independent. In contrast, HT-H adhesion to RL95-2 cells is largely divalent cation dependent since a relatively large number of cells failed to adhere after washing with EDTA (Table 1). Since a relatively high proportion of HT-H cells adhered to SNG-M cells and that adherence was not cation dependent, these cells were chosen for further study.

TABLE I

ADHESION OF HT-H CELL TO ENDOMETRIAL ADENOCARCINOMA CELLS

| –Cell Line[#] | Percentage HT-H cells attached | |
|---|---|---|
| | + EDTA | – EDTA |
| SNG-M | 56.9 ± 8.2 | 49.7 ± 7.3 |
| Hec1A | 29.6 ± 10.2 | 24.2 ± 8.3 |
| KLE | 32.5 ± 8.5 | 27.2 ± 4.8 |
| RL95 | 83.5 ± 9.7 | 20.4 ± 12.1 |
| AN3CA | 4.2 ± 0.8 | 2.1 ± 0.6 |

[#]Used as a monolayer without fixation.

Cell adhesion assays also were conducted using fixed cell monolayers. In this case, cells grown in 24 well tissue culture plates were treated with 1% paraformaldehyde in PBS for 15 min at RT. The fixed cells were washed in PBS and were used for cell adhesion assays as described above. The results showed that HT-H cells adhered efficiently to the surface of paraformaldehyde-fixed monolayer of SNG-M cells in a divalent cation independent manner (FIG. 1A). Furthermore, when SNG-M cells were added to a fixed monolayer of SNG-M cells, they adhered efficiently in a divalent cation independent manner (FIG. 1A).

COS-1 cells adhered minimally to SNG-M cells (FIG. 1A), whereas HeLa, HepG2, SW480 and A431 did not detectably adhere (not shown). Essentially the same results were obtained when fixed HT-H cell monolayers were used in place of SNG-M cell monolayers (FIG. 1B). In summary, adhesion between HT-H and SNG-M cells is cell type specific and divalent cation independent.

C. Morphological Evaluation of Adherent Cells

Electron microscopy was used to characterize the adherent interface formed during the co-culture of HT-H and SNG-M cells. SNG-M cells were grown in a Falcon 3001 (25×10 mm) tissue culture dish until reaching 50% confluency. HT-H cells were detached from the tissue culture dish by trypsin/EDTA treatment and were added to monolayers of SNG-M cells. The combined cells were cultured for up to 4 days. At various times, individual cultures were processed for transmission electron microscopy. Cells were fixed in freshly prepared fixative (10 mM NaIO4, 75 mM lysine, 37.5 mM sodium phosphate buffer, 2% paraformaldehyde, pH 6.2) for 15 min at RT. Cells then were washed with phosphate buffer, treated with glutaraldehyde and processed for electron microscopy as described previously (Klier et al., *Devel. Biol.* 57:440–449 (1977), which is incorporated herein by reference). Electron microscopy was performed using a Hitachi K-600 electron microscope.

Following 10 min co-culture, the apical surface of HT-H cells faced the apical surface of SNG-M cells (FIG. 2A) and many microvilli were present between the cells (FIG. 2B). After 6 hr, there were closer adhesive interactions between the cells (FIG. 2C), with the edges of the microvilli extending from one cell type and attaching to the cell surface of the other cell type (FIG. 2C). Occasional invagination in the plasma membrane of the SNG-M cells was observed (shown by an arrow in FIG. 2C). After 4 days, the microvilli had disappeared completely from the surfaces of both cell types and desmosome-like adherent junctions were present between the cell (FIG. 2D).

The results described using the in vitro cell adhesion assay are similar to the morphological studies of human implantation in vivo and in vitro (Lindenberg et al., *Hum. Reprod.* 1:533–538 (1986); Knoth and Larsen, *Acta Obstet.*

Gynecol. Scand. 51:385–393 (1972)). For example, during implantation, the trophoblast endometrial epithelial cells show characteristics which include: 1) reduction of microvilli in areas of attachment, 2) an invagination response of endometrial cells at the contact site, 3) formation of a junction complex or sign of focal adhesions between the trophoblast, and endometrial cells in a later stage of implantation and 4) intrusion of the trophoblast between the endometrial epithelia. Thus, the HT-H and SNG-M cells provided are a useful in vitro model of embryo implantation.

EXAMPLE II

EXPRESSION CLONING OF MOLECULES MEDIATING ADHESION OF HT-H CELLS TO SNG-M CELLS

This example describes a method to clone cDNA molecules that are involved in mediating cell adhesion.

A. Expression of a cDNA Library in COS-1 Cells

A functional cDNA expression cloning strategy was used to obtain the nucleic acid molecules encoding the proteins responsible for the initial, EDTA independent cell adhesion between HT-H and SNG-M cells (Aruffo and Seed, *Proc. Natl. Acad. Sci. (USA)* 84:8573–8577 (1987), which is incorporated herein by reference). COS-1 cells, which did not adhere efficiently to monolayers of SNG-M cells (see FIG. 1A), were chosen for transfection with a cDNA library derived from HT-H cells (obtained from Invitrogen Corp. Ltd; San Diego, Calif.). Poly-A mRNA prepared from freshly harvested HT-H cells was used to construct a unidirectional cDNA expression library in the mammalian expression vector pcDNAI. The cDNA library consisted of $2 \times 10^6$ independent clones with an insert size ranging from 0.5 to 3.0 kb.

COS-1 cells ($1 \times 10^8$ cells) were transfected with the HT-H cDNA library using electroporation. This method of transfection was used because the diethylaminoethyldextran and lipofection reagents used for other transfection methods increased the nonspecific adhesion of COS-1 cells to the SNG-M cells. COS-1 cells were grown in Falcon culture dishes until the cells reached about 75% confluency, were detached using 0.1% trypsin and 1 mM EDTA and suspended in DME medium containing 10% fetal bovine serum. The cells were pelleted by centrifugation, washed 2× with cold PBS and $1-0.5 \times 10^7$ cells/ml were suspended in PBS containing 100 μg/ml plasmid DNA. Electroporation was performed using a Gene Pulser (Biorad, Hercules, Calif.) at 0.4 kvolt with a capacitance of 125 μF. The transfected cells were cultured for 48 hr in DME medium containing 10% fetal bovine serum, 2 mM glutamine, 100 units/ml penicillin and 100 μg/ml streptomycin.

B. Screening the cDNA Expression Library by Cell Adhesion

The transfected COS-1 cells were selected for binding to an SNG-M cell monolayer. The SNG-M cells were cultured to confluency in a Falcon 3001 or 3005 tissue culture dish, then fixed with 1% paraformaldehyde in PBS at RT for 15 min. The fixed SNG-M cells were washed 3× with PBS and 1× with HBS.

Two days following electroporation, transfected COS-1 cells were detached from the tissue culture plate by incubating for 5–10 min with cell dissociation solution (Specialty Media, Lavalette, N.J.) supplemented with 1 mM EDTA. The cells were suspended in HBS containing 1 mM EDTA and were added to a fixed SNG-M cell monolayer and allowed to attach at RT for 20 min. The plate was washed 3× with HBS containing 1 mM EDTA and transfected COS-1 cells that remained on the SNG-M cell monolayer were mechanically detached by flushing EBS with a pasteur pipet. Approximately $1 \times 10^4$ COS-1 cells were recovered and added to a second SNG-M monolayer to adhere as described above. After 20 min, the nonadherent COS-1 cells were discarded by washing as above and the adherent cells (representing about $1 \times 10^3$ COS-1 cells) were solubilized with 1% SDS. Plasmid DNA was recovered from the SDS soluble extract and amplified in *E. coli* MC1061/P3 cells.

The plasmid DNA obtained from the transfected COS-1 cells was subjected to a second round of electroporation in COS-1 cells followed by selection by adhesion as described above, except that the number of cells used for transfection was reduced to $1 \times 10^6$ to $1 \times 10^7$ cells. After the first adhesion selection step, about $2 \times 10^3$ transfected COS-1 cells were attached to the SNG-M monolayer. After the second cell adhesion step, plasmid DNA was obtained by extraction with SDS as described above.

*E. coli* MC1061/P3 cells were transformed using plasmid DNA following the second transfection. Plasmid DNA from two hundred *E. coli* clones was divided into ten groups containing 20 plasmids each. Fresh COS-1 cells were transfected with each group containing the mixture of 20 clones and allowed to adhere to a monolayer of the SNG-M cells. The individual clones derived from a group that was positive for adhesion were each transfected into COS-1 cells and tested for adhesion. However, the transfected COS-1 cells derived from individual clones failed to adhere to the SNG-M cells. The 20 clones were screened again using a series of mixtures containing a decreasing number of clones. A mixture of two specific cDNA sequences were the minimum required to enable transfected COS-1 cells to adhere to SNG-M cells. The initial pair of cDNA clones identified were trophinin and tastin. The results in FIG. 1C demonstrate that COS-1 cells transfected with a mixture of trophinin and tastin cDNA adhered to a monolayer of SNG-M cells, while COS-1 cells transfected only with trophinin cDNA or tastin cDNA failed to adhere. Further screening of the remaining 200 clones for co-transfection with the trophinin clone identified two other clones which were required for adhesion. The additional two clones were named bystin and lastin.

The trophinin cDNA clone encodes an intrinsic membrane protein, while the tastin, bystin and lastin clones likely encode a cytoplasmic protein. The cDNA clones were sequenced by the dideoxy nucleotide chain termination method of Sanger et al. (*Proc. Natl. Acad. Sci. (USA)*, 74:5463–5467 (1977), which is incorporated herein by reference) using a modified T7 DNA polynuclease ("SEQUENASE", United States Biochemicals, Cleveland, Ohio). The nucleotide sequence of the trophinin cDNA was determined from restriction fragments subcloned into Bluescript from nested deletion mutants generated by exonuclease III (Boehringer Mannheim, Indianapolis, Ind.). The nucleotide sequence of the tastin, bystin and lastin cDNA were determined using oligonucleotide primers. Editing and analysis of the sequence was done using DNASIS (Hitachi, Tokyo, Japan) and PCgene software (Intelligenetics, Mountain View, Calif.). Sequence comparisons with the databases were performed using the "blast" network program (National Center for Biotechnology Information, NIH). The complete nucleotide sequence for trophinin cDNA is shown in FIG. 3 (SEQ ID NO: 1), while the complete nucleotide sequence of tastin and bystin and a partial nucleotide sequence of lastin are shown in FIG. 6 (SEQ ID NO: 4), FIG. 7 (SEQ ID NO: 6) and FIG. 8 (SEQ ID NO: 8), respectively.

The clone which contained the lastin sequence was missing the 5' end of the gene including the poly-A tail of the mRNA.

EXAMPLE III

CHARACTERIZATION OF TROPHININ

The complete cDNA sequence and the deduced amino acid sequence of trophinin are shown in FIG. 3. The trophinin cDNA clone covers 2524 nucleotides with an open reading frame encoding 749 amino acids. The 3' untranslated region consists of 250 nucleotides and contains a polyadenylation signal 12 bp upstream of the poly-A tail. An optimal translation initiation sequence (Kozak, supra, 1984) is associated with only one of the ATG codons in the near 5' region. Use of this ATG for translation initiation would result in a predicted molecular mass of 69.29 kDa for trophinin.

The plasmid cDNA clones were subjected to in vitro translation using T7 oligonucleotide primer, rabbit reticulocyte lysate (Promega, Madison, Wis.), RNA polymerase and $^{35}$S-methionine. The products were processed by SDS-PAGE and visualized by autoradiography. In vitro translation of trophinin cDNA showed a major product at 61 kDa (FIG. 4), which is in agreement with the predicted molecular mass of 69.29 kDa.

Hydropathy analysis (Kyte and Doolittle, supra, 1982) of trophinin defines this molecule as an intrinsic membrane protein having 8 separate transmembrane domains (FIG. 5A). No cleavable signal sequence was found in the cDNA clone coding for trophinin, however, the first putative membrane spanning domain (amino acids 66 to 120) follows an arginine residue at position 54 that can function as a stop transfer signal during translocation into the endoplasmic reticulum. Employment of the stop transfer sequence during translocation can result in the amino terminal segment of trophinin from the methionine at position 1 to the serine at position 65 being located in the cytoplasm. The location of the amino terminal portion of trophinin was examined using antibodies raised against a peptide within the predicted cytoplasmic tail of the trophinin (residues 23 to 31). In these experiments, the antibodies only reacted with HT-H cells that had their cell membranes removed by detergent treatment, indicating that the amino terminal portion of trophinin is located in the cytoplasm.

The amino terminal region of trophinin contains three serine and/or threonine residues that can function as potential phosphorylation sites (see FIG. 3). The threonine at position 7 is contained within a consensus site for phosphorylation by casein kinase II (Kemp and Pearson, supra, 1990). The serine residues at position 46 and 52 are located within consensus sequence sites for protein kinase C phosphorylation. The serine residue at position 46 also is contained within a consensus sequence site for cAMP/cGMP dependent phosphorylation. The presence of phosphorylation sites in a transmembrane protein such as trophinin indicates a likely mechanism for signalling the morphological changes in cells that are known to occur subsequent to trophinin-mediated adhesion (see FIGS. 2A, 2B, 2C and 2D).

Trophinin contains eight potential membrane spanning regions (FIG. 5A). The relative proportion of trophinin localized in the cytoplasm, in the membrane bilayer and on the cell surface is 10%, 56% and 34%, respectively. Four potential N-glycosylation sites, and thirteen potential O-glycosylation sites, are found within the predicted cell surface domains of trophinin (FIG. 3).

Greater than 90% of trophinin is contains a tandemly repeated decapeptide motif (FIG. 5B SEQ ID NO: 3). There are 69 such repeat sequences and they exhibit some variation in sequence and length. The predicted exposed cell surface domains of trophinin contain regions of decapeptide repeats that are hydrophilic in character. Three such exposed domains can be identified in trophinin, at amino acid positions 278 to 364 (SEQ ID NO: 20), 441 to 512 (SEQ ID NO: 21) and 634 to 719 (SEQ ID NO: 22) (see FIG. 3; bold lettering).

Protein secondary structure algorithms (Garnier et al., supra, 1978; Gascuel and Golmard, supra, 1988), predict that the decapeptide repeats conform to a repeated β-turn structure that can be a key structural element for efficient homophilic adhesion (not shown). Four potential N-glycosylation sites, N-X-S(T), and thirteen potential O-glycosylation sites, P-S(T) or S(T)-P, are found within the predicted cell surface domains of trophinin (FIG. 3). Trophinin has no significant homology to sequences in protein and nucleic acid databases.

EXAMPLE IV

CHARACTERIZATION OF TROPHININ-ASSISTING PROTEINS

The complete nucleotide sequence of the tastin cDNA clone (SEQ ID NO: 4) and the deduced amino acid sequence (SEQ ID NO: 5) are shown in FIG. 6. The tastin cDNA clone contains 2,577 nucleotides with an open reading frame encoding 778 amino acids. The 3' untranslated region contains 128 nucleotides and has a polyadenylation signal 11 bp upstream of the poly-A tail. The nucleotide sequence around the ATG at position 11 is contained within a consensus sequence for a translation initiation site (Kozak, supra, 1984). In vitro translation of the tastin cDNA produce a predominant product of 80 kDa (FIG. 4), consistent with the predicted molecular weight 83.75 kDa based on the cDNA open reading frame. Tastin is likely a cytoplasmic protein since it lacks an obvious secretory signal sequence and transmembrane helices as defined by hydropathy analysis (Kyte and Doolittle, supra, 1982), and shows a pattern of cell staining similar to other cytoplasmic proteins (see FIGS. 9C and 9D).

Tastin is rich in prolines, which account for 15.3% of the total amino acids of the protein. In addition, the region from residues 516 to 650 is cysteine rich (see italics in FIG. 6), with the majority of the cysteines located within four tandem repeat sequences of 33 amino acids each (not shown). Tastin also contains many serine and threonine residues and a tyrosine residue that, when considered with their adjacent amino acid residues, provide sequence motifs for protein kinase phosphorylation (FIG. 6). Specifically, tastin contains two cAMP/cGMP-dependent phosphorylation sites located at position 234 and 350 and sixteen protein kinase C phosphorylation sites, among which the threonine at position 179 most closely matches the consensus sequence (Kemp and Pearson, supra, 1990). Tastin also contains eleven serine and threonine residues that are potential casein kinase II phosphorylation sites and two threonines at positions 177 and 363 that are within a consensus MAP kinase phosphorylation site (Gonzalez et al., supra, 1991).

Tastin has no overall significant homology to previously reported protein sequences. Nucleotide sequence homology analysis of tastin identified the sequence HFBCL29 (Genbank accession number M85643), which was derived from a human fetal brain cDNA library. HFBCL29 shows homology to a portion of tastin cDNA (positions 2340 to 2057) provided the HFBCL29 sequence represents the non-coding stand of the DNA (ie. the homology is due to nucleotide base complementarity). Thus, HFBCL29 sequence would be homologous to a portion of the tastin if the former sequence had been recorded in the data base in the antisense direction. The protein sequence deduced from HFBCL29 is believed to be related to Y box binding protein-1 (Adams et al., sipra, 1992). However, the entire nucleotide sequence and deduced amino acid sequence of tastin overall are not homologous to the Y-box binding protein-1.

EXAMPLE V

PRODUCTION OF ANTIBODIES TO TROPHININ AND A TROPHININ ASSISTING PROTEIN (TASTIN)

Peptide sequence s of trophinin and tastin were analyzed to predict useful antigenic sites using the method of Hopp and Wood, *Mol. Immunol.* 20:483–489 (1983), which is incorporated herein by reference. A short sequence from the amino terminal end of trophinin and from tastin were selected as antigens. The sequences FEIEARAQE (SEQ ID NO: 10), representing residues 23 to 31 of trophinin, and DQENQDPRR (SEQ ID NO: 11), representing residues 41 to 49 of tastin, were chemically synthesized with a cysteine residue added to the amino terminus to facilitate protein conjugation. The peptides were conjugated to KLH using meta-maleimidobenzoyl N-hydroxysuccinimide ester (Sigma Chemical Co., St. Louis, Mo.) as described by Kitagawa and Aikawa (*J. Biochem.* 79:342–346 (1976)), which is incorporated herein by reference). New Zealand white rabbits were immunized the peptide-KLH conjugates according to the following procedure. On day 1, animals were injected subcutaneously with peptide conjugate emulsified in Freund's complete adjuvant. On day 14, the animals were boosted by subcutaneous injection of peptide conjugate emulsified in Freund's incomplete adjuvant. Animals were bled (30 ml) on days 24, 31 and 38 to obtain a source of antisera. Anti-peptide antibodies were purified from rabbit antisera by protein A affinity chromatography and peptide affinity chromatography as described by Richardson (*J. Virol.* 54:186–193 (1985), which is incorporated herein by reference). Rabbit antibodies to trophinin and tastin were used to detect these molecules in samples of cells and tissues (see Example VI).

To raise antibodies specific for portions of the trophinin molecule that are expressed on the external surface of the cell membrane, the three hydrophilic domains containing decapeptide repeats were separately expressed in bacteria as a fusion to glutathionine S-transferase (GST). The trophinin cDNA from the aspartic acid residue at position 278 to the serine residue at position 364 was amplified by PCR using the oligonucleotide primers GGAATTCATGGATG-GCTCTCCCAGCACTGGTG (SEQ ID NO: 14) and GCAGCTGAGTGCTGGTGCTTAGTGTACCACC (SEQ ID NO: 15) to produce the fusion protein GST551. The trophinin cDNA from the proline residue at position 441 to the serine residue at position 512 was amplified by PCR using the oligonucleotide primers GGAATTCATGCCCAG-CAACAGCATTGGC (SEQ ID NO: 16) and GCAGCT-GAGTACTGGTGCTGGGTCCATCACAAAAAC (SEQ ID NO: 17) to produce the fusion protein GST552. The trophinin cDNA from amino acid residues serine at position 634 to asparagine at position 719 was amplified by PCR using oligonucleotide primers GGAATTCATGAGCGATG-GCTTTGGCAGTAG (SEQ ID NO: 12) and CGTCGACT-CAGTTTGGTCCACCGCCGAAGCCAG (SEQ ID NO: 13) to produce the fusion protein GST553. The trophinin cDNA from the methionine residue at position 1 to the serine residue at position 66 was amplified by PCR using the oligonucleotide primers GGAATTCATGGATATCGACT-GCCTA (SEQ ID NO: 18) and GCAGCTGAGTCTG-GAGCTGGGTGCACCAT (SEQ ID NO: 19) to produce the fusion protein GST-N-terminal trophinin.

The amplified DNA fragments of the fusion proteins were ligated into pGEX-4T-1 vector (Pharmacia, Piscataway N.J.) at the EcoRI and XhoI sites. *E. coli* HB101 was transformed with the plasmid vectors and the GST fusion proteins were produced as described by the manufacturer. The fusion proteins were initially purified by affinity chromatography on Glutathionine-agarose beads (Pharmacia).

For immunization to produce antibodies to the external domains of trophinin, GST551, GST552 and GST553 fusion proteins were electrophoresed in SDS-PAGE, the gel was stained with Coomassie blue, and the band containing the fusion protein excised from the gel. The polyacrylamide gel containing the purified fusion proteins were injected into rabbits to produce antibodies acccording to the procedure described previously for the synthetic peptides except that antibodies were not purified from the antiserum.

EXAMPLE VI

DETECTION OF TROPHININ AND A TROPHININ ASSISTING PROTEIN (TASTIN) IN CELLS AND TISSUES

This example provides methods to identify and localize trophinin and tastin in various types of samples.

A. Localization of Trophinin and Tastin in Cultured Cells

HT-H and SNG-M cells were grown on glass coverslips in Falcon 3005 tissue culture dishes for 2–3 days. The cells were fixed at RT for 15 min with 1% paraformaldehyde in PBS, then washed 4× with PBS. Fixed cells were incubated in PBS containing 5% bovine serum albumin (IIF buffer) plus 0.1% saponin at RT for 30 min, then incubated 45 min at RT with anti-trophinin or anti-tastin antibody diluted in IIF buffer plus 0.1% saponin to permeabilize the cells. After further washing with IIF buffer plus 0.1% saphonin, cells were incubated for 30 min at RT with fluorescein isothio-cyanate (FITC)-conjugated goat anti rabbit IgG F(ab')$_2$ (Cappel, Durham, N.C.) diluted in IIF buffer. Coverslips containing the cells were washed 3× with IIF buffer and 1× with PBS, then placed upside down on a slide glass in an aliquot of 95% glycerol and 5% PBS. Micrographs were obtained with a Zeiss Axioplan fluorescence microscope or a Zeiss LSM410 confocal laser scanning microscope.

Antibodies to an N-terminal peptide of trophinin (residue 23–31) showed staining of permeabilized HT-H and SNG-M cells that appears as a lace-like pattern due to clustering of the fluorescence over the cell surface (FIGS. 9A and 9B). A tangential view by confocal microscopy (not shown) showed that the majority of trophinin is detected in the upper plasma membranes of these cells. A small amount of trophinin staining is detected inside the cells and in their basal plasma membranes.

Figure 9C:
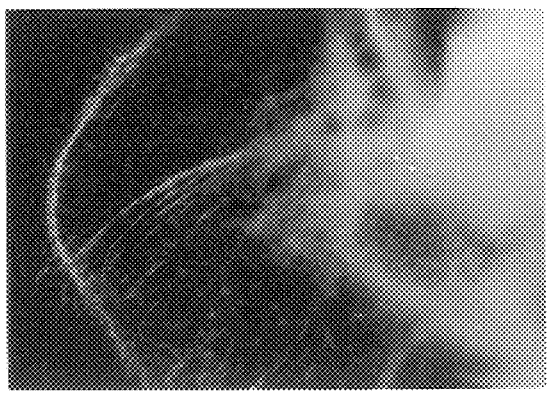
Figure 9D:
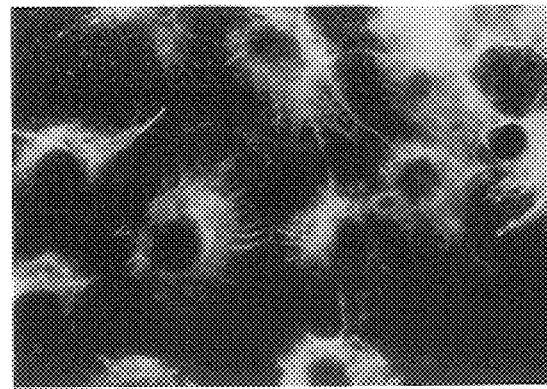

Antibody to an N-terminal peptide of tastin exhibited a diffuse staining consistent with detection of fibers in the cytoplasm of permeabilized HT-H and SNG-M (FIGS. 9C and 9D). The fibers spread from the perinuclear region toward the edge of the cells indicating that tastin likely associates with the cytoskeleton in HT-H and SNG-M cells. Thus, tastin containing fibers that associate with the cytoskeleton can be involved in organizing trophinin as patches in the plasma membranes to effect efficient cell adhesion.

Antisera to GST551, GST552 and GST553, reactive with the hydrophilic domains of trophinin, were tested for staining the cell surfaces of unpermeabilized HT-H cells. For these experiments, cells were processed as for permeabilized cells except that saphonin was not used. The staining pattern observed for all three antibodies was similar to that obtained when permeabilized cells were stained by antibodies to the N-terminal domain of trophinin (residue 23–31, see FIG. 9A). Similar results were obtained using SNG-M cells as the cell targets (see FIG. 9B). These results demonstrate that all three hydrophilic domains of trophinin are exposed on the cell surface of HT-H and SNG-M cells.

COS-1 cells transfected with trophinin cDNA were also tested for staining with the antisera to the trophinin hydrophilic external domains. The cells showed a weak and diffuse staining on the surface with all three antisera. In contrast, COS-1 cells transfected with a mixture of trophinin and tastin cDNA showed stronger and more clustered staining with the antisera. These data indicate that tastin functions to create multivalent patches of trophinin on the cell surface. Such clustering of trophinin provides a basis for the observed requirement of COS-1 cells to be transfected with cDNA encoding for trophinin and a trophinin-assisted protein in order to undergo trophinin-mediated cell adhesion.

The detection of trophinin exposed on the cell surface of cultured cells was also determined using cell surface labelling and immunoprecipitation techniques. Proteins exposed on the external side of the plasma cell membrane were labelled at their cysteine residues with biotin-maleimide (Sigma). HT-H and SNG-M cells were removed from culture flasks by scraping with a rubber policeman and washed with ice-cold PBS. $1 \times 10^6$ cells were suspended in 1 ml PBS and mixed with 20 µl of dimethylformamide containing 10 µg biotin-maleimide. After 1 hr on ice, the cells were washed and resuspended in 1% NP-40 nonionic detergent to produce a soluble lysate and an insoluble material. After centrifugation to remove the NP-40 soluble lysate, the insoluble material was solubilized in 0.1% SDS essentially as described previously (Oshima et al. *Dev. Biol.* 99:447–455 (1983), which is incorporated herein by reference). The NP-40 soluble lysate was mixed with avidin-agarose beads (Sigma) for two hr at RT and the beads were centrifuged to yield an avidin-unbound fraction of the NP-40 soluble lysate. The beads were then washed and bound proteins eluted by boiling the beads for 2 minutes in SDS sample buffer (see Harlow and Lane, supra, 1988). Both bound and non-bound avidin fractions and the SDS soluble fraction were evaluated for their content of trophinin by immunoblotting with the antiserum to GST553 and with the antibodies to the N-terminal domain of trophinin (residue 23–31). Immunoblotting was performed by SDS-PAGE and nitrocellulose transfer essentially as described by Towbin et al. (*Proc. Natl. Acad. Sci.* (*USA*), 76:4350–4354 (1976)) except that enhanced chemiluminescence was used for detection of immunoreactive bands (ECL kit, Amersham, Buckinghamshire, UK).

Immunoblotting of surface labelled cells showed three bands with apparent molecular masses of 90 kDa, 120 kDa and 140 kDa in HT-H cells and SNG-M cells. The majority of trophinin was detected in the avidin-bound fraction as compared to the non-bound fraction, indicating that trophinin is exposed on the external side of the cell surface. A significant amount of trophinin was insoluble in NP-40 detergent, indicating that some trophinin molecules are associated with the cytoskeleton and, therefore, that trophinin is an intrinsic plasma membrane protein.

Trophinin was evaluated by IIF to determine if the hydrophilic extracellular domains of trophinin could be used to detect trophinin expressing cells. The trophinin extracellular domain fusion proteins GST551, GST552 and GST553, the GST-N-terminal domain (residue 1–66) and GST were labelled with biotin succinamide (Sigma). SNG-M, HT-H and COS-1 cells transfected with a mixture of trophinin and tastin cDNA were grown on coverslips and processed for cell staining with the biotinylated proteins essentially as was described for the antibodies to the external domains of trophinin, except that avidin-FITC (Cappel) was used in place of a FITC-secondary antibody.

All three biotinylated trophinin extracellular domain fusion proteins stained unpermeabilized HT-H, SNG-M and the COS-1 cells transfected with trophinin and tastin cDNA. In contrast, no staining was seen when the cells were reacted with biotinylated GST or the biotinylated GST-N-terminal domain of trophinin. These results indicate that the soluble trophinin domains can bind trophinin exposed on the surface of the cells and, therefore, that the trophinin cell surface hydrophilic domains can be used to detect trophinin expressing cells.

B. Detection of Trophinin and Tastin by Northern Blotting

Total RNA was isolated from HT-H cells, SNG-M cells and COS-1 cells by the acid-guanidine:phenol:chloroform method (Chirgwin et al., *Biochem.* 18:5294–5299 (1979), which is incorporated herein by reference). Poly-A mRNA was prepared using oligo dT cellulose affinity chromatography (poly A Quick, Strategene). Five µg of poly-A RNA was electrophoresed in a 1% agarose formaldehyde gel and the RNA was transferred by blotting to nitrocellulose filter paper. The filter paper was heated at 80° C. for 2 hr to fix the RNA and was prehybridized and hybridized as described by Thomas (Thomas, *Proc. Natl. Acad. Sci.* (*USA*) 77:5201–5205, (1980), which is incorporated herein by reference). cDNA clones were labeled with $^{32}$P-α-dCTP (DuPont/NEN, Boston Mass.) using a random oligo labeling kit (Boehringer-Mannheim, Indianapolis Ind.). Northern blotting was also performed using MTN-1 filters containing human tissue RNA (Clontech, Palo Alto, Calif.) prepared as described above.

A $^{32}$P-cDNA probe for trophinin detected a 3,5, 7.5 and 10 kb mRNA species from both HT-H and SNG-M cells which were not detectable from COS-1 cells (not shown). A $^{32}$P-cDNA probe for tastin detected a 3.2 and 3.3 kb mRNA species from both HT-H and SNG-M cells (not shown). The probes also detected the appropriate sized mRNA species in the poly-A mRNA from placenta, lung and liver, but at lower levels than that seen in the cell lines. Poly-A mRNA from heart, brain, muscle, kidney and pancreas failed to react with either the trophinin or tastin probes.

C. Expression and Localization of Trophinin and Tastin in Human Placental and Endometrial Tissues.

Tissues embedded in paraffin were obtained from the University of California at San Diego Tissue Bank. These tissues included placenta, endometrial, liver, lung, kidney, ovary, spleen, colon, testes, brain, and spinal cord. Paraffin embedded tissue sections (0.5 or 3 µM thick) were deparaffinized and microwaved in 10 mM citrate buffer, pH 6.0, in order to recover antigenic activities (Shi et al., *J. Histochem. Cytochem.* 39:741–748 (1991), which is incorporated herein by reference). The sections were stained with anti-trophinin or anti-trophinin-assisting protein antibodies and FITC goat anti-rabbit antibodies according to methods described above (see Example VI, subsection A). Mouse anti-lamp-1 antibodies were used to detect endosomes and lysosomes (Fukuda, supra, 1991). Double immunostaining for lamp-1 and trophinin was performed in de-paraffinized and microwaved sections using the following sequence of reagents (Williams and Fukuda, *J. Cell Biol.* 111:955–966 (1990) which is incorporated herein by reference): 1) anti-lamp-1 antibody, 2) rhodamine conjugated goat anti-mouse IgG antibody (Sigma, St Louis, Mo.), 3) anti-trophinin antibody and 4) FITC goat anti-rabbit IgG antibody (Cappel, Durham, N.C.).

Anti-trophinin and anti-tastin antibodies failed to stain cells in placenta, liver, lung, kidney, ovary, spleen, colon, testes, brain, and spinal cord, except for macrophages present in the tissues (not shown). Trophinin was not detected in term placental tissues or in placental tissues from early (7–10 week) pregnancy (except for macrophages), whereas trophinin was readily detected in focal regions in the apical plasma membranes of syncytiotrophoblasts of chorionic villi at 7 weeks pregnancy (FIG. 10A). Trophinin also was present in cytoplasmic vesicles of syncytiotrophoblasts in the chorionic villi from 7–10 week pregnancy (FIG. 10B). Double immunostaining with the lamp-1 lysosome marker showed co-localization of trophinin and lamp-1 in these vesicles, indicating that trophinins are present in lysosomes and/or endosomes (not shown). These observations indicate that trophinin expression is strictly regulated and appears on the surface membranes of syncytiotrophoblasts at early stages of pregnancy but not at later stages of pregnancy. Trophinins seen in lysosomes of syncytiotrophoblasts at later stages of pregnancy can be undergoing degradation after being removed from the cell surface. Tastin was not detected in most of the chorionic villi from 7–10 week pregnancy, except for a weak signal in the lysosomes in syncytiotrophoblasts (not shown).

In addition to expression by the embryo, trophinin also is expressed in the uterus at the apical plasma membrane of the surface epithelium on day 16/17 endometrium (FIG. 10C), but not in endometrium during the proliferation stage (day 6–13) or ovulation stage (day 14). Endometrial biopsy samples taken from late secretory phases (day 20–28) showed staining for trophinin in the mucin. Tastin could not be detected in any of the above endometrial tissue samples except for mucin. These results, like those for the embryo, demonstrate that trophinin expression is strictly regulated in endometrial tissue, with trophinin appearing for only a short time on the cell surface. Thus, trophinin is involved in embryo implantation as its pattern of expression is consistent with the concept of an implantation window.

Further evidence that trophinin is involved in implantation comes for immunofluorescence analysis of a blastocyst taken from a Rhesus monkey. After removal of the exterior *Zona pellucida,* the expanded blastocyst showed strong staining at the apical plasma membranes of the trophectoderm cells. More intense staining for trophinin was observed on trophoblast cells located at the embryonic pole as opposed to the mural pole (see FIGS. 11A and 11B). Such polarized staining is consistent with the observation that the embryonic pole of both primate and human blastocysts is the site of attachment to the endometrial epithelium (Enders et al, supra (1981); Knoth and Larson, supra (1972) and Lindenberg et al, supra (1986)).

Trophinin was also detected both in trophoblasts and endometrial epithelial cells at the implantation site of a Macaque monkey (see FIGS. 11C and 11D). Trophinin positive cells were seen among those anchoring villi and cytotrophoblasts of the blastocyst and in plaque cells or hypertrophic endometrial epithelium (not shown). As shown in FIG. 11D, the most intense staining for trophinin was observed among trophoblast and endometrial epithelial cells located at the site of adhesion between these two tissues.

These results with non-human primate embryos together with the studies on human endometrial and implantation site tissues provide strong support for the conservation of trophinin as a mediator of implantation among all primates.

EXAMPLE VII

USE OF TROPHININ TO MEDIATE ADHESION BETWEEN CELLS

This example provides methods to adhere cells together using trophinin.

COS-1 cells were transfected with a mixture of trophinin and tastin cDNA and evaluated for cell adhesion capability. Transfected cells that were suspended in HBS with 1 mM EDTA and maintained at RT formed distinct cell aggregates after about 10–20 min, while untransfected COS-1 cells formed little if any aggregates under the same conditions. Thus, the expression of both trophinin and tastin in COS-1 cells provided these cells with the ability to aggregate together in suspension.

The ability of various cells to adhere to a monolayer of COS-1 cells transfected with trophinin and tastin cDNA was evaluated in the adhesion cell assay in the presence of 1 mM EDTA. COS-1 cells transfected with trophinin and tastin cDNA bound the monolayer while COS-1 cells transfected with the control pcDNA1 vector failed to show significant binding. When the monolayer was pretreated for 1 hr at RT with antisera to GST551, GST552 or GST553 trophinin external domain fusion proteins, the ability of the monolayer to adhere to COS-1 cells transfected with trophinin and tastin cDNA was greatly diminished. These results indicate that transfection with both trophinin and tastin, a trophinin-assisted protein, can confer the property of undergoing adhesion mediated by trophinin. The inhibition of cell adhesion by antibodies to the hydrophilic external domains of trophinin confirms the role of such domains in trophinin-mediated cell adhesion.

Trophinin-mediated cell adhesion between HT-H suspension cells and a monolayer of SNG-M cells and between SNG-M cells and a monolayer of SNG-M cells was also tested for inhibition by antibodies to trophinin. In both cases, pretreatment of the monolayer with antiserum to GST553 (FIG. 1D) or with Fab' fragments of antibodies to GST553 significantly inhibited the amount of cell adhesion. Similar results were obtained when SNG-M cells were added to an SNG-M cell monolayer. In contrast to these results, pretreatment of the SNG-M cell monolayer with preimmune rabbit sera or with antibodies to a synthetic peptide of the amino terminal region of trophinin (residues 23–31) failed to inhibit adhesion of SNG-M or HT-H cells. These experiments provide further evidence for the role of the external hydrophilic domains of trophinin in trophinin-mediated cell adhesion.

Although the invention has been described with reference to the examples provided above, it should be understood that various modifications can be made without departing from the spirit of the invention. Accordingly, the invention is limited only by the claims.

5,910,451

I claim:

1. A substantially purified trophinin, wherein the trophinin comprises the amino acid sequence shown as SEQ ID NO:2 in FIG. 3.

2. An active fragment of trophinin comprising the amino acid sequence Phe-Glu-Ile-Glu-Ala-Arg-Ala-Gln-Glu (SEQ ID NO:10).

3. An active fragment of trophinin comprising an amino acid sequence selected from the group consisting of: residues 278 to 364 (SEQ ID NO:20; FIG. 3); residues 441 to 512 (SEQ ID NO:21; FIG. 3); and residues 634 to 719 (SEQ ID NO:22; FIG. 3).

4. A substantially purified trophinin-assisting protein tastin, wherein the tastin comprises the amino acid sequence shown as SEQ ID NO:5 in FIG. 6.

5. An active fragment of tastin comprising the amino acid sequence Asp-Gln-Glu-Asn-Gln-Asp-Pro-Arg-Arg (SEQ ID NO:11).

6. A substantially purified trophinin-assisting protein bystin, wherein the bystin comprises the amino acid sequence shown as SEQ ID NO:7 in FIG. 7.

7. A substantially purified trophinin-assisting protein lastin, wherein the lastin comprises the amino acid sequence shown as SEQ ID NO:9 in FIG. 8.

8. A method to detect the presence of trophinin in a sample, wherein the trophinin comprises the amino acid sequence shown as SEQ ID NO:2 in FIG. 3, comprising the steps of:

a. obtaining the sample;

b. contacting said sample with an agent that can specifically bind to trophinin under suitable conditions, which allow specific binding of said agent to trophinin; and c. detecting specific binding of said agent, which indicates the presence of trophinin.

9. A method to detect the presence of a trophinin-assisting protein in a sample wherein said trophinin-assisting protein comprises an amino acid sequence selected from the group consisting of tastin (SEQ ID NO:5), bystin (SEQ ID NO:7) and lastin (SEQ ID NO:9), comprising the steps of:

a. obtaining the sample;

b. contacting said sample with an agent that can specifically bind to said trophinin-assisting protein, wherein said contacting is under suitable conditions, which allow specific binding of said agent to said trophinin-assisting protein; and c. detecting specific binding of said agent, which indicates the presence of said trophinin-assisting protein.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 2524 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 28..2275

(xi) SEQUENCE DESCRIPTION: SEQ ID NO:1:

```
GTGGCTGGGC CCTGGAATTG GGATGAC ATG GAT ATC GAC TGC CTA ACA AGG         51
                                Met Asp Ile Asp Cys Leu Thr Arg
                                  1               5

GAA GAG TTA GGC GAT GAT TCT CAG GCC TGG AGC AGA TTT TCA TTT GAA       99
Glu Glu Leu Gly Asp Asp Ser Gln Ala Trp Ser Arg Phe Ser Phe Glu
         10                  15                  20

ATT GAG GCC AGA GCC CAA GAA AAT GCA GAT GCC AGC ACC AAC GTC AAC      147
Ile Glu Ala Arg Ala Gln Glu Asn Ala Asp Ala Ser Thr Asn Val Asn
 25                  30                  35                  40

TTC AGC AGA GGA GCT AGT ACC AGG GCT GGC TTC AGC GAT CGT GCT AGT      195
Phe Ser Arg Gly Ala Ser Thr Arg Ala Gly Phe Ser Asp Arg Ala Ser
                 45                  50                  55

ATT AGC TTC AAT GGT GCA CCC AGC TCC AGT GGT GGC TTC AGT GGT GGA      243
Ile Ser Phe Asn Gly Ala Pro Ser Ser Ser Gly Gly Phe Ser Gly Gly
             60                  65                  70

CCT GGC ATT ACC TTT GGT GTT GCA CCC AGC ACC AGT GCC AGC TTC AGC      291
Pro Gly Ile Thr Phe Gly Val Ala Pro Ser Thr Ser Ala Ser Phe Ser
         75                  80                  85

AAT ACA GCC AGC ATT AGC TTT GGT GGT ACA CTG AGC ACT AGC TCC AGC      339
Asn Thr Ala Ser Ile Ser Phe Gly Gly Thr Leu Ser Thr Ser Ser Ser
 90                  95                 100

TTC AGC AGC GCA GCC AGC ATT AGC TTT GGT TGT GCA CAC AGC ACC AGC      387
Phe Ser Ser Ala Ala Ser Ile Ser Phe Gly Cys Ala His Ser Thr Ser
105                 110                 115                 120

ACT AGT TTC AGC AGT GAA GCC AGC ATT AGC TTT GGT GGC ATG CCT TGT      435
Thr Ser Phe Ser Ser Glu Ala Ser Ile Ser Phe Gly Gly Met Pro Cys
                125                 130                 135

ACC AGT GCC AGC TTT AGT GGT GGA GTC AGC TCT AGT TTT AGT GGC CCA      483
Thr Ser Ala Ser Phe Ser Gly Gly Val Ser Ser Ser Phe Ser Gly Pro
            140                 145                 150

CTC AGC ACC AGT GCC ACT TTC AGT GGT GGA GCC AGC TCT GGC TTT GGA      531
Leu Ser Thr Ser Ala Thr Phe Ser Gly Gly Ala Ser Ser Gly Phe Gly
        155                 160                 165

GGC ACA CTC AGC ACC ACG GCT GGC TTT AGT GGT GTA CTC AGC ACT AGC      579
Gly Thr Leu Ser Thr Thr Ala Gly Phe Ser Gly Val Leu Ser Thr Ser
    170                 175                 180

ACC AGC TTT GGC AGT GCA CCC ACA ACG AGC ACA GTC TTC AGT AGT GCG      627
Thr Ser Phe Gly Ser Ala Pro Thr Thr Ser Thr Val Phe Ser Ser Ala
185                 190                 195                 200

CTT AGC ACC AGC ACT GGC TTT GGA GGC ATA CTC AGC ACC AGT GTC TGT      675
Leu Ser Thr Ser Thr Gly Phe Gly Gly Ile Leu Ser Thr Ser Val Cys
                205                 210                 215

TTT GGT GGC TCT CCC AGC TCC AGT GGT AGC TTT GGT GGT ACA CTC AGT      723
Phe Gly Gly Ser Pro Ser Ser Ser Gly Ser Phe Gly Gly Thr Leu Ser
```

```
                220                 225                 230
ACC AGT ATC TGC TTC GGT GGT TCT CCC TGC ACC AGC ACT GGC TTT GGA      771
Thr Ser Ile Cys Phe Gly Gly Ser Pro Cys Thr Ser Thr Gly Phe Gly
            235                 240                 245

GGC ACA CTT AGC ACC AGT GTC TCC TTT GGT GGC TCT TCC AGC ACC AGT      819
Gly Thr Leu Ser Thr Ser Val Ser Phe Gly Gly Ser Ser Ser Thr Ser
        250                 255                 260

GCC AAT TTT GGT GGT ACA CTA AGT ACC AGC ATC TGC TTT GAT GGC TCT      867
Ala Asn Phe Gly Gly Thr Leu Ser Thr Ser Ile Cys Phe Asp Gly Ser
265                 270                 275                 280

CCC AGC ACT GGT GCT GGG TTT GGT GGT GCT CTC AAC ACC AGT GCC AGC      915
Pro Ser Thr Gly Ala Gly Phe Gly Gly Ala Leu Asn Thr Ser Ala Ser
                285                 290                 295

TTT GGC AGT GTG CTC AAC ACC AGT ACT GGT TTT GGT GGT GCT ATG AGC      963
Phe Gly Ser Val Leu Asn Thr Ser Thr Gly Phe Gly Gly Ala Met Ser
            300                 305                 310

ACC AGT GCT GAC TTT GGC GGT ACA CTA AGC ACC AGT GTC TGC TTT GGT     1011
Thr Ser Ala Asp Phe Gly Gly Thr Leu Ser Thr Ser Val Cys Phe Gly
        315                 320                 325

GGC TCT CCT GGC ACC AGT GTC AGC TTT GGC AGT GCA CTC AAC ACC AAT     1059
Gly Ser Pro Gly Thr Ser Val Ser Phe Gly Ser Ala Leu Asn Thr Asn
330                 335                 340

GCT GGT TAT GGT GGT GCT GTC AGC ACC AAC ACT GAC TTT GGT GGT ACA     1107
Ala Gly Tyr Gly Gly Ala Val Ser Thr Asn Thr Asp Phe Gly Gly Thr
345                 350                 355                 360

CTA AGC ACC AGC GTC TGT TTT GGT GGC TCT CCC AGC ACC AGT GCT GGC     1155
Leu Ser Thr Ser Val Cys Phe Gly Gly Ser Pro Ser Thr Ser Ala Gly
                365                 370                 375

TTT GGT GGT GCA CTC AAC ACC AAT GCC AGC TTT GGC TGT GCC GTC AGC     1203
Phe Gly Gly Ala Leu Asn Thr Asn Ala Ser Phe Gly Cys Ala Val Ser
            380                 385                 390

ACC AGT GCC AGC TTC AGT GGT GCT GTC AGC ACC AGT GCT TGC TTC AGT     1251
Thr Ser Ala Ser Phe Ser Gly Ala Val Ser Thr Ser Ala Cys Phe Ser
        395                 400                 405

GGT GCA CCA ATC ACC AAC CCT GGC TTT GGC GGT GCA TTT AGC ACC AGT     1299
Gly Ala Pro Ile Thr Asn Pro Gly Phe Gly Gly Ala Phe Ser Thr Ser
        410                 415                 420

GCT GGC TTC GGT GGT GCA CTT AGT ACC GCT GCT GAC TTC GGT GGT ACT     1347
Ala Gly Phe Gly Gly Ala Leu Ser Thr Ala Ala Asp Phe Gly Gly Thr
425                 430                 435                 440

CCC AGC AAC AGC ATT GGC TTT GGT GCT GCT CCC AGC ACC AGT GTC AGC     1395
Pro Ser Asn Ser Ile Gly Phe Gly Ala Ala Pro Ser Thr Ser Val Ser
                445                 450                 455

TTT GGT GGT GCT CAT GGC ACC AGC CTC TGT TTT GGT GGA GCT CCC AGC     1443
Phe Gly Gly Ala His Gly Thr Ser Leu Cys Phe Gly Gly Ala Pro Ser
            460                 465                 470

ACC AGC CTC TGC TTT GGC AGT GCA TCT AAT ACT AAC CTA TGC TTT GGT     1491
Thr Ser Leu Cys Phe Gly Ser Ala Ser Asn Thr Asn Leu Cys Phe Gly
        475                 480                 485

GGC CCT CCT AGC ACC AGT GCC TGC TTT AGT GGT GCT ACC AGC CCT AGT     1539
Gly Pro Pro Ser Thr Ser Ala Cys Phe Ser Gly Ala Thr Ser Pro Ser
        490                 495                 500

TTT TGT GAT GGA CCC AGC ACC AGT ACC GGT TTC AGC TTT GGC AAT GGG     1587
Phe Cys Asp Gly Pro Ser Thr Ser Thr Gly Phe Ser Phe Gly Asn Gly
505                 510                 515                 520

TTA AGC ACC AAT GCT GGA TTT GGT GGT GGA CTG AAC ACC AGT GCT GGC     1635
Leu Ser Thr Asn Ala Gly Phe Gly Gly Gly Leu Asn Thr Ser Ala Gly
                525                 530                 535

TTT GGT GGT GGC CTA GGC ACC AGT GCT GGC TTC AGT GGT GGC CTA AGC     1683
Phe Gly Gly Gly Leu Gly Thr Ser Ala Gly Phe Ser Gly Gly Leu Ser
```

```
                540             545             550
ACA AGT TCT GGC TTT GAT GGT GGG CTA GGT ACC AGC GCT GGC TTC GGT    1731
Thr Ser Ser Gly Phe Asp Gly Gly Leu Gly Thr Ser Ala Gly Phe Gly
            555             560             565

GGA GGA CCA GGC ACC AGC ACT GGT TTT GGT GGT GGA CTG GGC ACC AGT    1779
Gly Gly Pro Gly Thr Ser Thr Gly Phe Gly Gly Gly Leu Gly Thr Ser
        570             575             580

GCT GGC TTC AGT GGC GGA CTG GGC ACC AGT GCT GGC TTT GGT GGT GGA    1827
Ala Gly Phe Ser Gly Gly Leu Gly Thr Ser Ala Gly Phe Gly Gly Gly
585             590             595             600

CTG GTC ACT AGT GAT GGC TTT GGT GGT GGA CTG GGC ACC AAT GCT AGT    1875
Leu Val Thr Ser Asp Gly Phe Gly Gly Gly Leu Gly Thr Asn Ala Ser
            605             610             615

TTC GGC AGC ACA CTT GGC ACC AGT GCT GGC TTT AGT GGT GGC CTC AGC    1923
Phe Gly Ser Thr Leu Gly Thr Ser Ala Gly Phe Ser Gly Gly Leu Ser
        620             625             630

ACC AGC GAT GGC TTT GGC AGT AGG CCT AAT GCC AGC TTC GAC AGA GGA    1971
Thr Ser Asp Gly Phe Gly Ser Arg Pro Asn Ala Ser Phe Asp Arg Gly
            635             640             645

CTG AGT ACC ATC ATT GGC TTT GGC AGT GGT TCC AAC ACC AGC ACT GGC    2019
Leu Ser Thr Ile Ile Gly Phe Gly Ser Gly Ser Asn Thr Ser Thr Gly
        650             655             660

TTT ACT GGC GAA CCC AGC ACC AGC ACG GGC TTC AGT AGT GGA CCC AGT    2067
Phe Thr Gly Glu Pro Ser Thr Ser Thr Gly Phe Ser Ser Gly Pro Ser
665             670             675             680

TCT ATT GTT GGC TTC AGC GGT GGA CCA AGC ACT GGT GTT GGC TTC TGC    2115
Ser Ile Val Gly Phe Ser Gly Gly Pro Ser Thr Gly Val Gly Phe Cys
            685             690             695

AGT GGA CCA AGC ACC AGT GGC TTC AGC GGT GGA CCC AGC ACA GGA GCT    2163
Ser Gly Pro Ser Thr Ser Gly Phe Ser Gly Gly Pro Ser Thr Gly Ala
        700             705             710

GGC TTC GGC GGT GGA CCA AAC ACT GGT GCT GGC TTT GGT GGT GGA CCG    2211
Gly Phe Gly Gly Gly Pro Asn Thr Gly Ala Gly Phe Gly Gly Gly Pro
            715             720             725

AGC ACC AGT GCT GGC TTT GGC AGT GGA GCC GCC AGT CTT GGT GCC TGT    2259
Ser Thr Ser Ala Gly Phe Gly Ser Gly Ala Ala Ser Leu Gly Ala Cys
        730             735             740

GGC TTC TCG TAT GGC T AGTGAGGTTT CAGATACCGC TAATAAATTG CAGTAGTCCT   2315
Gly Phe Ser Tyr Gly
745

TCCCATGGAG CCAAAGTACC TTGGATCTTT GTCCACACAG CAGTCAAGGC AGTTATGGCC   2375

CATCAGCTGA GGGTGTCATG TGATGGAAAA ATCTGTTTGC TGTTCCTGCT TTATTGTTTG   2435

CTTTCTGTGT GCTGTCATAT TTTGGTATCA GAGTTACATT AAATTTGCAA AATGAAAAAA   2495

AAAAAAAAAA AAAAAAAAA AAAAAAAA                                       2524
```

(2) INFORMATION FOR SEQ ID NO:2:

(i) SEQUENCE CHARACTERISTICS:
        (A) LENGTH: 749 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Ile Asp Cys Leu Thr Arg Glu Glu Leu Gly Asp Asp Ser Gln
 1               5                  10                  15

Ala Trp Ser Arg Phe Ser Phe Glu Ile Glu Ala Arg Ala Gln Glu Asn
                20                  25                  30
```

-continued

```
Ala Asp Ala Ser Thr Asn Val Asn Phe Ser Arg Gly Ala Ser Thr Arg
        35                  40                  45

Ala Gly Phe Ser Asp Arg Ala Ser Ile Ser Phe Asn Gly Ala Pro Ser
    50                  55                  60

Ser Ser Gly Gly Phe Ser Gly Gly Pro Gly Ile Thr Phe Gly Val Ala
65                  70                  75                  80

Pro Ser Thr Ser Ala Ser Phe Ser Asn Thr Ala Ser Ile Ser Phe Gly
                85                  90                  95

Gly Thr Leu Ser Thr Ser Ser Phe Ser Ser Ala Ala Ser Ile Ser
            100                 105                 110

Phe Gly Cys Ala His Ser Thr Ser Thr Ser Phe Ser Ser Glu Ala Ser
            115                 120                 125

Ile Ser Phe Gly Gly Met Pro Cys Thr Ser Ala Ser Phe Ser Gly Gly
130                 135                 140

Val Ser Ser Ser Phe Ser Gly Pro Leu Ser Thr Ser Ala Thr Phe Ser
145                 150                 155                 160

Gly Gly Ala Ser Ser Gly Phe Gly Gly Thr Leu Ser Thr Thr Ala Gly
                165                 170                 175

Phe Ser Gly Val Leu Ser Thr Ser Ser Phe Gly Ser Ala Pro Thr
            180                 185                 190

Thr Ser Thr Val Phe Ser Ser Ala Leu Ser Thr Ser Thr Gly Phe Gly
            195                 200                 205

Gly Ile Leu Ser Thr Ser Val Cys Phe Gly Gly Ser Pro Ser Ser Ser
210                 215                 220

Gly Ser Phe Gly Gly Thr Leu Ser Thr Ser Ile Cys Phe Gly Gly Ser
225                 230                 235                 240

Pro Cys Thr Ser Thr Gly Phe Gly Gly Thr Leu Ser Thr Ser Val Ser
                245                 250                 255

Phe Gly Gly Ser Ser Ser Thr Ser Ala Asn Phe Gly Gly Thr Leu Ser
            260                 265                 270

Thr Ser Ile Cys Phe Asp Gly Ser Pro Ser Thr Gly Ala Gly Phe Gly
            275                 280                 285

Gly Ala Leu Asn Thr Ser Ala Ser Phe Gly Ser Val Leu Asn Thr Ser
290                 295                 300

Thr Gly Phe Gly Gly Ala Met Ser Thr Ser Ala Asp Phe Gly Gly Thr
305                 310                 315                 320

Leu Ser Thr Ser Val Cys Phe Gly Gly Ser Pro Gly Thr Ser Val Ser
                325                 330                 335

Phe Gly Ser Ala Leu Asn Thr Asn Ala Gly Tyr Gly Gly Ala Val Ser
            340                 345                 350

Thr Asn Thr Asp Phe Gly Gly Thr Leu Ser Thr Ser Val Cys Phe Gly
            355                 360                 365

Gly Ser Pro Ser Thr Ser Ala Gly Phe Gly Gly Ala Leu Asn Thr Asn
370                 375                 380

Ala Ser Phe Gly Cys Ala Val Ser Thr Ser Ala Ser Phe Ser Gly Ala
385                 390                 395                 400

Val Ser Thr Ser Ala Cys Phe Ser Gly Ala Pro Ile Thr Asn Pro Gly
                405                 410                 415

Phe Gly Gly Ala Phe Ser Thr Ser Ala Gly Phe Gly Gly Ala Leu Ser
            420                 425                 430

Thr Ala Ala Asp Phe Gly Gly Thr Pro Ser Asn Ser Ile Gly Phe Gly
            435                 440                 445

Ala Ala Pro Ser Thr Ser Val Ser Phe Gly Gly Ala His Gly Thr Ser
450                 455                 460
```

-continued

```
Leu Cys Phe Gly Gly Ala Pro Ser Thr Ser Leu Cys Phe Gly Ser Ala
465                 470                475                 480

Ser Asn Thr Asn Leu Cys Phe Gly Gly Pro Pro Ser Thr Ser Ala Cys
                485                 490                495

Phe Ser Gly Ala Thr Ser Pro Ser Phe Cys Asp Gly Pro Ser Thr Ser
                500                 505                 510

Thr Gly Phe Ser Phe Gly Asn Gly Leu Ser Thr Asn Ala Gly Phe Gly
                515                 520                 525

Gly Gly Leu Asn Thr Ser Ala Gly Phe Gly Gly Leu Gly Thr Ser
530                 535                 540

Ala Gly Phe Ser Gly Gly Leu Ser Thr Ser Ser Gly Phe Asp Gly Gly
545                 550                 555                 560

Leu Gly Thr Ser Ala Gly Phe Gly Gly Pro Gly Thr Ser Thr Gly
                565                 570                 575

Phe Gly Gly Gly Leu Gly Thr Ser Ala Gly Phe Ser Gly Gly Leu Gly
                580                 585                 590

Thr Ser Ala Gly Phe Gly Gly Leu Val Thr Ser Asp Gly Phe Gly
                595                 600                 605

Gly Gly Leu Gly Thr Asn Ala Ser Phe Gly Ser Thr Leu Gly Thr Ser
610                 615                 620

Ala Gly Phe Ser Gly Gly Leu Ser Thr Ser Asp Gly Phe Gly Ser Arg
625                 630                 635                 640

Pro Asn Ala Ser Phe Asp Arg Gly Leu Ser Thr Ile Ile Gly Phe Gly
                645                 650                 655

Ser Gly Ser Asn Thr Ser Thr Gly Phe Thr Gly Glu Pro Ser Thr Ser
                660                 665                 670

Thr Gly Phe Ser Ser Gly Pro Ser Ser Ile Val Gly Phe Ser Gly Gly
                675                 680                 685

Pro Ser Thr Gly Val Gly Phe Cys Ser Gly Pro Ser Thr Ser Gly Phe
                690                 695                 700

Ser Gly Gly Pro Ser Thr Gly Ala Gly Phe Gly Gly Pro Asn Thr
705                 710                 715                 720

Gly Ala Gly Phe Gly Gly Gly Pro Ser Thr Ser Ala Gly Phe Gly Ser
                725                 730                 735

Gly Ala Ala Ser Leu Gly Ala Cys Gly Phe Ser Tyr Gly
                740                 745
```

(2) INFORMATION FOR SEQ ID NO:3:

(i) SEQUENCE CHARACTERISTICS:
        (A) LENGTH: 674 amino acids
        (B) TYPE: amino acid
        (D) TOPOLOGY: linear (xi) SEQUENCE DESCRIPTION: SEQ ID NO:3:

```
Phe Ser Gly Gly Pro Gly Ile Thr Phe Gly Val Ala Pro Ser Thr Ser
1               5                   10                  15

Ala Ser Phe Ser Asn Thr Ala Ser Ile Ser Phe Gly Gly Thr Leu Ser
                20                  25                  30

Thr Ser Ser Ser Phe Ser Ala Ala Ser Ile Ser Phe Gly Cys Ala
                35                  40                  45

His Ser Thr Ser Thr Ser Phe Ser Ser Glu Ala Ser Ile Ser Phe Gly
                50                  55                  60

Gly Met Pro Cys Thr Ser Ala Ser Phe Gly Gly Val Ser Ser Ser
65                  70                  75                  80
```

```
Phe Ser Gly Pro Leu Ser Thr Ser Ala Thr Phe Ser Gly Gly Ala Ser
                 85                  90                  95

Ser Gly Phe Gly Gly Thr Leu Ser Thr Ala Gly Phe Ser Gly Val
            100                 105                 110

Leu Ser Thr Ser Thr Ser Phe Gly Ser Ala Pro Thr Thr Ser Thr Val
        115                 120                 125

Phe Ser Ser Ala Leu Ser Thr Ser Thr Gly Phe Gly Gly Ile Leu Ser
130                 135                 140

Thr Ser Val Cys Phe Gly Gly Ser Pro Ser Ser Gly Ser Phe Gly
145                 150                 155                 160

Gly Thr Leu Ser Thr Ser Ile Cys Phe Gly Gly Ser Pro Cys Thr Ser
                165                 170                 175

Thr Gly Phe Gly Gly Thr Leu Ser Thr Ser Val Ser Phe Gly Gly Ser
            180                 185                 190

Ser Ser Thr Ser Ala Asn Phe Gly Gly Thr Leu Ser Thr Ser Ile Cys
            195                 200                 205

Phe Asp Gly Ser Pro Ser Thr Gly Ala Gly Phe Gly Gly Ala Leu Asn
210                 215                 220

Thr Ser Ala Ser Phe Gly Ser Val Leu Asn Thr Ser Thr Gly Phe Gly
225                 230                 235                 240

Gly Ala Met Ser Thr Ser Ala Asp Phe Gly Gly Thr Leu Ser Thr Ser
                245                 250                 255

Val Cys Phe Gly Gly Ser Pro Gly Thr Ser Val Ser Phe Gly Ser Ala
            260                 265                 270

Leu Asn Thr Asn Ala Gly Tyr Gly Gly Ala Val Ser Thr Asn Thr Asp
            275                 280                 285

Phe Gly Gly Thr Leu Ser Thr Ser Val Cys Phe Gly Gly Ser Pro Ser
290                 295                 300

Thr Ser Ala Gly Phe Gly Gly Ala Leu Asn Thr Asn Ala Ser Phe Gly
305                 310                 315                 320

Cys Ala Val Ser Thr Ser Ala Ser Phe Ser Gly Ala Val Ser Thr Ser
                325                 330                 335

Ala Cys Phe Ser Gly Ala Pro Ile Thr Asn Pro Gly Phe Gly Gly Ala
                340                 345                 350

Phe Ser Thr Ser Ala Gly Phe Gly Gly Ala Leu Ser Thr Ala Ala Asp
            355                 360                 365

Phe Gly Gly Thr Pro Ser Asn Ser Ile Gly Phe Gly Ala Ala Pro Ser
370                 375                 380

Thr Ser Val Ser Phe Gly Gly Ala His Gly Thr Ser Leu Cys Phe Gly
385                 390                 395                 400

Gly Ala Pro Ser Thr Ser Leu Cys Phe Gly Ser Ala Ser Asn Thr Asn
                405                 410                 415

Leu Cys Phe Gly Gly Pro Pro Ser Thr Ser Ala Cys Phe Ser Gly Ala
            420                 425                 430

Thr Ser Pro Ser Phe Cys Asp Gly Pro Ser Thr Ser Thr Gly Phe Ser
            435                 440                 445

Phe Gly Asn Gly Leu Ser Thr Gly Phe Gly Gly Leu Asn Thr Ser
        450                 455                 460

Ala Gly Phe Gly Gly Gly Leu Gly Thr Ser Ala Gly Phe Ser Gly Gly
465                 470                 475                 480

Leu Ser Thr Ser Ser Gly Phe Asp Gly Gly Leu Gly Thr Ser Ala Gly
                485                 490                 495

Phe Gly Gly Gly Pro Gly Thr Ser Thr Gly Phe Gly Gly Gly Leu Gly
            500                 505                 510
```

-continued

```
Thr Ser Ala Gly Phe Ser Gly Gly Leu Gly Thr Ser Ala Gly Phe Gly
        515                 520                 525

Gly Gly Leu Val Thr Ser Asp Gly Phe Gly Gly Leu Gly Thr Asn
    530                 535                 540

Ala Ser Phe Gly Ser Thr Leu Gly Thr Ser Ala Gly Phe Ser Gly Gly
545                 550                 555                 560

Leu Ser Thr Ser Asp Gly Phe Gly Ser Arg Pro Asn Ala Ser Phe Asp
                565                 570                 575

Arg Gly Leu Ser Thr Ile Ile Gly Phe Gly Ser Gly Ser Asn Thr Ser
                580                 585                 590

Thr Gly Phe Thr Gly Glu Pro Ser Thr Ser Gly Phe Ser Ser Gly
        595                 600                 605

Pro Ser Ser Ile Val Gly Phe Ser Gly Gly Pro Ser Thr Gly Gly Phe
        610                 615                 620

Cys Ser Gly Pro Ser Thr Ser Gly Phe Ser Gly Gly Pro Ser Thr Gly
625                 630                 635                 640

Ala Gly Phe Gly Gly Pro Asn Thr Gly Ala Gly Phe Gly Gly Gly
                645                 650                 655

Pro Ser Thr Ser Ala Gly Phe Gly Ser Gly Ala Ala Ser Leu Gly Ala
                660                 665                 670

Cys Gly
```

(2) INFORMATION FOR SEQ ID NO:4:

(i) SEQUENCE CHARACTERISTICS:
        (A) LENGTH: 2577 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 111..2445

(xi) SEQUENCE DESCRIPTION: SEQ ID NO:4:

```
CGCCAGGAAC AGCTTGAGGT ACCTGAGCCC TGCCCTCCAG CAGCACCCGA GAGGGTCAGG        60

AGAAAAGCGG AGGAAGCTGG GTAGGCCCTG AGGGGCCTCG GTAAGCCATC ATG ACC          116
                                                        Met Thr
                                                          1

ACC CGG CAA GCC ACG AAG GAT CCC CTC CTC CGG GGT GTA TCT CCT ACC         164
Thr Arg Gln Ala Thr Lys Asp Pro Leu Leu Arg Gly Val Ser Pro Thr
        5                  10                  15

CCT AGC AAG ATT CCG GTA CGC TCT CAG AAA CGC ACG CCT TTC CCC ACT         212
Pro Ser Lys Ile Pro Val Arg Ser Gln Lys Arg Thr Pro Phe Pro Thr
 20                  25                  30

GTT ACA TCG TGC GCC GTG GAC CAG GAG AAC CAA GAT CCA AGG AGA TGG         260
Val Thr Ser Cys Ala Val Asp Gln Glu Asn Gln Asp Pro Arg Arg Trp
 35                  40                  45                  50

GTG CAG AAA CCA CCG CTC AAT ATT CAA CGC CCC CTC GTT GAT TCA GCA         308
Val Gln Lys Pro Pro Leu Asn Ile Gln Arg Pro Leu Val Asp Ser Ala
             55                  60                  65

GGC CCC AGG CCG AAA GCC AGG CAC CAG GCA GAG ACA TCA CAA AGA TTG         356
Gly Pro Arg Pro Lys Ala Arg His Gln Ala Glu Thr Ser Gln Arg Leu
         70                  75                  80

GTG GGG ATC AGT CAG CCT CGG AAC CCC TTG GAA GAG CTC AGG CCT AGC         404
Val Gly Ile Ser Gln Pro Arg Asn Pro Leu Glu Glu Leu Arg Pro Ser
     85                  90                  95

CCT AGG GGT CAA AAT GTG GGG CCT GGG CCC CCT GCC CAG ACA GAG GCT         452
Pro Arg Gly Gln Asn Val Gly Pro Gly Pro Pro Ala Gln Thr Glu Ala
```

-continued

```
         100                 105                  110
CCA GGG ACC ATA GAG TTT GTG GCT GAC CCT GCA GCC CTG GCC ACC ATC    500
Pro Gly Thr Ile Glu Phe Val Ala Asp Pro Ala Ala Leu Ala Thr Ile
115              120                 125                 130

CTG TCA GGT GAG GGT GTG AAG AGC TGT CAC CTG GGG CGC CAG CCT AGT    548
Leu Ser Gly Glu Gly Val Lys Ser Cys His Leu Gly Arg Gln Pro Ser
                 135                 140                 145

CTG GCT AAA AGA GTA CTG GTT CGA GGA AGT CAG GGA GGC ACC ACC CAG    596
Leu Ala Lys Arg Val Leu Val Arg Gly Ser Gln Gly Gly Thr Thr Gln
                 150                 155                 160

AGG GTC CAG GGT GTT CGG GCC TCT GCA TAT TTG GCC CCC AGA ACC CCC    644
Arg Val Gln Gly Val Arg Ala Ser Ala Tyr Leu Ala Pro Arg Thr Pro
                 165                 170                 175

ACC CAC CGA CTG GAC CCT GCC AGG GCT TCC TGC TTC TCT AGG CTG GAG    692
Thr His Arg Leu Asp Pro Ala Arg Ala Ser Cys Phe Ser Arg Leu Glu
                 180                 185                 190

GGA CCA GGA CCT CGA GGC CGG ACA TTG TGC CCC CAG AGG CTA CAG GCT    740
Gly Pro Gly Pro Arg Gly Arg Thr Leu Cys Pro Gln Arg Leu Gln Ala
195                  200                 205                 210

CTG ATT TCA CCT TCA GGA CCT TCC TTT CAC CCT TCC ACT CAC CCC AGT    788
Leu Ile Ser Pro Ser Gly Pro Ser Phe His Pro Ser Thr His Pro Ser
                 215                 220                 225

TTC CAG GAG CTA AGA AGG GAG ACA GCT GGC AGC AGC CGG ACT TCA GTG    836
Phe Gln Glu Leu Arg Arg Glu Thr Ala Gly Ser Ser Arg Thr Ser Val
                 230                 235                 240

AGC CAG GCC TCA GGA TTG CTC CTG GAG ACC CCA GTC CAG CCT GCT TTC    884
Ser Gln Ala Ser Gly Leu Leu Leu Glu Thr Pro Val Gln Pro Ala Phe
                 245                 250                 255

TCT CTT CCT AAA GGA GAA CGC GAG GTT GTC ACT CAC TCA GAT GAA GGA    932
Ser Leu Pro Lys Gly Glu Arg Glu Val Val Thr His Ser Asp Glu Gly
                 260                 265                 270

GGT GTG GCC TCT CTT GGT CTG GCC CAG CGA GTA CCA TTA AGA GAA AAC    980
Gly Val Ala Ser Leu Gly Leu Ala Gln Arg Val Pro Leu Arg Glu Asn
275                  280                 285                 290

CGA GAA ATG TCA CAT ACC AGG GAC AGC CAT GAC TCC CAC CTG ATG CCC    1028
Arg Glu Met Ser His Thr Arg Asp Ser His Asp Ser His Leu Met Pro
                 295                 300                 305

TCC CCT GCC CCT GTG GCC CAG CCC TTG CCT GGC CAT GTG GTG CCA TGT    1076
Ser Pro Ala Pro Val Ala Gln Pro Leu Pro Gly His Val Val Pro Cys
                 310                 315                 320

CCA TCA CCC TTT GGA CGG GCT CAG CGT GTA CCC TCC CCA GGC CCT CCA    1124
Pro Ser Pro Phe Gly Arg Ala Gln Arg Val Pro Ser Pro Gly Pro Pro
                 325                 330                 335

ACT CTG ACC TCA TAT TCA GTG TTG CGG CGT CTC ACC GTT CAA CCT AAA    1172
Thr Leu Thr Ser Tyr Ser Val Leu Arg Arg Leu Thr Val Gln Pro Lys
                 340                 345                 350

ACC CGG TTC ACA CCC ATG CCA TCA ACC CCC AGA GTT CAG CAG GCC CAG    1220
Thr Arg Phe Thr Pro Met Pro Ser Thr Pro Arg Val Gln Gln Ala Gln
355                  360                 365                 370

TGG CTG CGT GGT GTC TCC CCT CAG TCC TGC TCT GAA GAT CCT GCC CTG    1268
Trp Leu Arg Gly Val Ser Pro Gln Ser Cys Ser Glu Asp Pro Ala Leu
                 375                 380                 385

CCC TGG GAG CAG GTT GCC GTC CGG TTG TTT GAC CAG GAG AGT TGT ATA    1316
Pro Trp Glu Gln Val Ala Val Arg Leu Phe Asp Gln Glu Ser Cys Ile
                 390                 395                 400

AGG TCA CTG GAG GGT TCT GGG AAA CCA CCG GTG GCC ACT CCT TCT GGA    1364
Arg Ser Leu Glu Gly Ser Gly Lys Pro Pro Val Ala Thr Pro Ser Gly
                 405                 410                 415

CCC CAC TCT AAC AGA ACC CCC AGC CTC CAG GAG GTG AAG ATT CAA CGC    1412
Pro His Ser Asn Arg Thr Pro Ser Leu Gln Glu Val Lys Ile Gln Arg
```

-continued

```
        420                 425                 430
ATC GGT ATC CTG CAA CAG CTG TTG AGA CAG GAA GTA GAG GGG CTG GTA      1460
Ile Gly Ile Leu Gln Gln Leu Leu Arg Gln Glu Val Glu Gly Leu Val
435                 440                 445                 450

GGG GGC CAG TGT GTC CCT CTT AAT GGA GGC TCT TCT CTG GAT ATG GTT      1508
Gly Gly Gln Cys Val Pro Leu Asn Gly Gly Ser Ser Leu Asp Met Val
                    455                 460                 465

GAA CTT CAG CCC CTG CTG ACT GAG ATT TCT AGA ACT CTG AAT GCC ACA      1556
Glu Leu Gln Pro Leu Leu Thr Glu Ile Ser Arg Thr Leu Asn Ala Thr
                470                 475                 480

GAG CAT AAC TCT GGG ACT TCC CAC CTT CCT GGA CTG TTA AAA CAC TCA      1604
Glu His Asn Ser Gly Thr Ser His Leu Pro Gly Leu Leu Lys His Ser
            485                 490                 495

GGG CTG CCA AAG CCC TGT CTT CCA GAG GAG TGC GGG GAA CCA CAG CCC      1652
Gly Leu Pro Lys Pro Cys Leu Pro Glu Glu Cys Gly Glu Pro Gln Pro
        500                 505                 510

TGC CCT CCG GCA GAG CCT GGG CCC CCA GAG GCC TTC TGT AGG AGT GAG      1700
Cys Pro Pro Ala Glu Pro Gly Pro Pro Glu Ala Phe Cys Arg Ser Glu
515                 520                 525                 530

CCT GAG ATA CCA GAG CCC TCC CTC CAG GAA CAG CTT GAA GTA CCA GAG      1748
Pro Glu Ile Pro Glu Pro Ser Leu Gln Glu Gln Leu Glu Val Pro Glu
                535                 540                 545

CCC TAC CCT CCA GCA GAA CCC AGG CCC CTA GAG TCC TGC TGT AGG AGT      1796
Pro Tyr Pro Pro Ala Glu Pro Arg Pro Leu Glu Ser Cys Cys Arg Ser
            550                 555                 560

GAG CCT GAG ATA CCG GAG TCC TCT CGC CAG GAA CAG CTT GAG GTA CCT      1844
Glu Pro Glu Ile Pro Glu Ser Ser Arg Gln Glu Gln Leu Glu Val Pro
        565                 570                 575

GAG CCC TGC CCT CCA GCA GAA CCC AGG CCC CTA GAG TCC TAC TGT AGG      1892
Glu Pro Cys Pro Pro Ala Glu Pro Arg Pro Leu Glu Ser Tyr Cys Arg
580                 585                 590

ATT GAG CCT GAG ATA CCG GAG TCC TCT CGC CAG GAA CAG CTT GAG GTA      1940
Ile Glu Pro Glu Ile Pro Glu Ser Ser Arg Gln Glu Gln Leu Glu Val
595                 600                 605                 610

CCT GAG CCC TGC CCT CCA GCA GAA CCC GGG CCC CTT CAG CCC AGC ACC      1988
Pro Glu Pro Cys Pro Pro Ala Glu Pro Gly Pro Leu Gln Pro Ser Thr
                615                 620                 625

CAG GGG CAG TCT GGA CCC CCA GGG CCC TGC CCT AGG GTA GAG CTG GGG      2036
Gln Gly Gln Ser Gly Pro Pro Gly Pro Cys Pro Arg Val Glu Leu Gly
            630                 635                 640

GCA TCA GAG CCC TGC ACC CTG GAA CAT AGA AGT CTA GAG TCC AGT CTA      2084
Ala Ser Glu Pro Cys Thr Leu Glu His Arg Ser Leu Glu Ser Ser Leu
        645                 650                 655

CCA CCC TGC TGC AGT CAG TGG GCT CCA GCA ACC ACC AGC CTG ATC TTC      2132
Pro Pro Cys Cys Ser Gln Trp Ala Pro Ala Thr Thr Ser Leu Ile Phe
660                 665                 670

TCT TCC CAA CAC CCG CTT TGT GCC AGC CCC CCT ATC TGC TCA CTC CAG      2180
Ser Ser Gln His Pro Leu Cys Ala Ser Pro Pro Ile Cys Ser Leu Gln
675                 680                 685                 690

TCT TTG AGA CCC CCA GCA GGC CAG GCA GGC CTC AGC AAT CTG GCC CCT      2228
Ser Leu Arg Pro Pro Ala Gly Gln Ala Gly Leu Ser Asn Leu Ala Pro
                695                 700                 705

CGA ACC CTA GCC CTG AGG GAG AGC CTC AAA TCG TGT TTA ACC GCC ATC      2276
Arg Thr Leu Ala Leu Arg Glu Ser Leu Lys Ser Cys Leu Thr Ala Ile
            710                 715                 720

CAC TGC TTC CAC GAG GCT CGT CTG GAC GAT GAG TGT GCC TTT TAC ACC      2324
His Cys Phe His Glu Ala Arg Leu Asp Asp Glu Cys Ala Phe Tyr Thr
        725                 730                 735

AGC CGA GCC TCT CCC TCA GGC CCC ACC CGG GTC TGC ACC AAC CCT GTG      2372
Ser Arg Ala Ser Pro Ser Gly Pro Thr Arg Val Cys Thr Asn Pro Val
```

-continued

```
                 740                 745                 750
GCT ACA TTA CTC GAA TGG CAG GAT GCC CTG TGT TTC ATT CCA GTT GGT       2420
Ala Thr Leu Leu Glu Trp Gln Asp Ala Leu Cys Phe Ile Pro Val Gly
755                 760                 765                 770

TCT GCT GCC CCC CAG GGC TCT CCA T GATGAGACAA CCACTCCTGC                2465
Ser Ala Ala Pro Gln Gly Ser Pro
                775

CCTGCCGTAC TTCTTCCTTT TAGCCCTTAT TTATTGTCGG TCTGCCCATG GGACTGGGAG      2525

CCGCCCACTT TTGTCCTCAA TAAAGTTTCT AAAGTAAAAA AAAAAAAAAA AA              2577
```

(2) INFORMATION FOR SEQ ID NO:5:

(i) SEQUENCE CHARACTERISTICS:
        (A) LENGTH: 778 amino acids
        (B) TYPE: amino acid
        (D) TOPOLOGY: linear (ii) MOLECULE TYPE: protein (xi) SEQUENCE DESCRIPTION: SEQ ID NO:5:

```
Met Thr Thr Arg Gln Ala Thr Lys Asp Pro Leu Leu Arg Gly Val Ser
 1               5                  10                  15

Pro Thr Pro Ser Lys Ile Pro Val Arg Ser Gln Lys Arg Thr Pro Phe
                20                  25                  30

Pro Thr Val Thr Ser Cys Ala Val Asp Gln Glu Asn Gln Asp Pro Arg
            35                  40                  45

Arg Trp Val Gln Lys Pro Leu Asn Ile Gln Arg Pro Leu Val Asp
        50                  55                  60

Ser Ala Gly Pro Arg Pro Lys Ala Arg His Gln Ala Glu Thr Ser Gln
65                  70                  75                  80

Arg Leu Val Gly Ile Ser Gln Pro Arg Asn Pro Leu Glu Glu Leu Arg
                85                  90                  95

Pro Ser Pro Arg Gly Gln Asn Val Gly Pro Gly Pro Pro Ala Gln Thr
               100                 105                 110

Glu Ala Pro Gly Thr Ile Glu Phe Val Ala Asp Pro Ala Ala Leu Ala
           115                 120                 125

Thr Ile Leu Ser Gly Glu Gly Val Lys Ser Cys His Leu Gly Arg Gln
130                 135                 140

Pro Ser Leu Ala Lys Arg Val Leu Val Arg Gly Ser Gln Gly Gly Thr
145                 150                 155                 160

Thr Gln Arg Val Gln Gly Val Arg Ala Ser Ala Tyr Leu Ala Pro Arg
                165                 170                 175

Thr Pro Thr His Arg Leu Asp Pro Ala Arg Ala Ser Cys Phe Ser Arg
            180                 185                 190

Leu Glu Gly Pro Gly Pro Arg Gly Arg Thr Leu Cys Pro Gln Arg Leu
        195                 200                 205

Gln Ala Leu Ile Ser Pro Ser Gly Pro Ser Phe His Pro Ser Thr His
    210                 215                 220

Pro Ser Phe Gln Glu Leu Arg Arg Glu Thr Ala Gly Ser Ser Arg Thr
225                 230                 235                 240

Ser Val Ser Gln Ala Ser Gly Leu Leu Leu Glu Thr Pro Val Gln Pro
                245                 250                 255

Ala Phe Ser Leu Pro Lys Gly Glu Arg Glu Val Val Thr His Ser Asp
            260                 265                 270

Glu Gly Gly Val Ala Ser Leu Gly Leu Ala Gln Arg Val Pro Leu Arg
        275                 280                 285
```

-continued

```
Glu Asn Arg Glu Met Ser His Thr Arg Asp Ser His Asp Ser His Leu
    290                 295                 300

Met Pro Ser Pro Ala Pro Val Ala Gln Pro Leu Pro Gly His Val Val
305                 310                 315                 320

Pro Cys Pro Ser Pro Phe Gly Arg Ala Gln Arg Val Pro Ser Pro Gly
                325                 330                 335

Pro Pro Thr Leu Thr Ser Tyr Ser Val Leu Arg Leu Thr Val Gln
            340                 345                 350

Pro Lys Thr Arg Phe Thr Pro Met Pro Ser Thr Pro Arg Val Gln Gln
        355                 360                 365

Ala Gln Trp Leu Arg Gly Val Ser Pro Gln Ser Cys Ser Glu Asp Pro
370                 375                 380

Ala Leu Pro Trp Glu Gln Val Ala Val Arg Leu Phe Asp Gln Glu Ser
385                 390                 395                 400

Cys Ile Arg Ser Leu Glu Gly Ser Gly Lys Pro Pro Val Ala Thr Pro
                405                 410                 415

Ser Gly Pro His Ser Asn Arg Thr Pro Ser Leu Gln Glu Val Lys Ile
                420                 425                 430

Gln Arg Ile Gly Ile Leu Gln Leu Leu Arg Gln Glu Val Glu Gly
        435                 440                 445

Leu Val Gly Gly Gln Cys Val Pro Leu Asn Gly Ser Ser Leu Asp
450                 455                 460

Met Val Glu Leu Gln Pro Leu Leu Thr Glu Ile Ser Arg Thr Leu Asn
465                 470                 475                 480

Ala Thr Glu His Asn Ser Gly Thr Ser His Leu Pro Gly Leu Leu Lys
                485                 490                 495

His Ser Gly Leu Pro Lys Pro Cys Leu Pro Glu Cys Gly Glu Pro
                500                 505                 510

Gln Pro Cys Pro Pro Ala Glu Pro Gly Pro Glu Ala Phe Cys Arg
        515                 520                 525

Ser Glu Pro Glu Ile Pro Glu Pro Ser Leu Gln Glu Leu Glu Val
        530                 535                 540

Pro Glu Pro Tyr Pro Pro Ala Glu Pro Arg Pro Leu Glu Ser Cys Cys
545                 550                 555                 560

Arg Ser Glu Pro Glu Ile Pro Glu Ser Ser Arg Gln Glu Gln Leu Glu
                565                 570                 575

Val Pro Glu Pro Cys Pro Pro Ala Glu Pro Arg Pro Leu Glu Ser Tyr
            580                 585                 590

Cys Arg Ile Glu Pro Glu Ile Pro Glu Ser Ser Arg Gln Glu Gln Leu
        595                 600                 605

Glu Val Pro Glu Pro Cys Pro Pro Ala Glu Pro Gly Pro Leu Gln Pro
    610                 615                 620

Ser Thr Gln Gly Gln Ser Gly Pro Pro Gly Pro Cys Pro Arg Val Glu
625                 630                 635                 640

Leu Gly Ala Ser Glu Pro Cys Thr Leu Glu His Arg Ser Leu Glu Ser
                645                 650                 655

Ser Leu Pro Pro Cys Cys Ser Gln Trp Ala Pro Ala Thr Thr Ser Leu
            660                 665                 670

Ile Phe Ser Ser Gln His Pro Leu Cys Ala Ser Pro Ile Cys Ser
        675                 680                 685

Leu Gln Ser Leu Arg Pro Pro Ala Gly Gln Ala Gly Leu Ser Asn Leu
    690                 695                 700

Ala Pro Arg Thr Leu Ala Leu Arg Glu Ser Leu Lys Ser Cys Leu Thr
705                 710                 715                 720
```

5,910,451

-continued

```
Ala Ile His Cys Phe His Glu Ala Arg Leu Asp Asp Glu Cys Ala Phe
            725                 730                 735

Tyr Thr Ser Arg Ala Ser Pro Ser Gly Pro Thr Arg Val Cys Thr Asn
        740                 745                 750

Pro Val Ala Thr Leu Leu Glu Trp Gln Asp Ala Leu Cys Phe Ile Pro
    755                 760                 765

Val Gly Ser Ala Ala Pro Gln Gly Ser Pro
    770                 775
```

(2) INFORMATION FOR SEQ ID NO:6:

(i) SEQUENCE CHARACTERISTICS:
        (A) LENGTH: 1293 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 70..988

(xi) SEQUENCE DESCRIPTION: SEQ ID NO:6:

```
AATTCGCGTG CCATAGAGAT GTTCATGAAC AAGAACCCTC CTGCCAGGCG CACCCTGGCT          60

GACATCATC ATG GAG AAG CTG ACT GAG AAG CAG ACA GAG GTT GAG ACA            108
          Met Glu Lys Leu Thr Glu Lys Gln Thr Glu Val Glu Thr
            1               5                  10

GTC ATG TCA GAG GTG TCG GGC TTC CCT ATG CCC CAG CTG GAC CCC CGG          156
Val Met Ser Glu Val Ser Gly Phe Pro Met Pro Gln Leu Asp Pro Arg
 15                  20                  25

GTC CTA GAA GTG TAC AGG GGG GTC CGG GAG GTA TTA TCT AAG TAC CGC          204
Val Leu Glu Val Tyr Arg Gly Val Arg Glu Val Leu Ser Lys Tyr Arg
 30                  35                  40                  45

AGT GGA AAA CTG CCC AAG GCA TTT AAG ATC ATC CCT GCA CTC TCC AAC          252
Ser Gly Lys Leu Pro Lys Ala Phe Lys Ile Ile Pro Ala Leu Ser Asn
             50                  55                  60

TGG GAG CAA ATC CTC TAC GTC ACA GAG CCG GAG GCC TGG ACT GCA GCT          300
Trp Glu Gln Ile Leu Tyr Val Thr Glu Pro Glu Ala Trp Thr Ala Ala
         65                  70                  75

GCC ATG TAC CAG GCC ACC AGG ATT TTT GCC TCT AAC CTG AAG GAA CGC          348
Ala Met Tyr Gln Ala Thr Arg Ile Phe Ala Ser Asn Leu Lys Glu Arg
     80                  85                  90

ATG GCC CAG CGC TTC TAC AAC CTT GTC CTG CTC CCT CGA GTA CGA GAT          396
Met Ala Gln Arg Phe Tyr Asn Leu Val Leu Leu Pro Arg Val Arg Asp
 95                 100                 105

GAC GTT GGT GAA TAC AAA CGA CTC AAC TTC CAT CTC TAC ATG GCT CTC          444
Asp Val Gly Glu Tyr Lys Arg Leu Asn Phe His Leu Tyr Met Ala Leu
110                 115                 120                 125

AAG AAG GCC CTT TTC AAA CCT GGA GCC TGG TTC AAA GGG ATC CTG ATT          492
Lys Lys Ala Leu Phe Lys Pro Gly Ala Trp Phe Lys Gly Ile Leu Ile
             130                 135                 140

CCA CTG TGC GAG TCT GGC ACT TGT ACC CTC CGG GAA GCC ATC ATT GTG          540
Pro Leu Cys Glu Ser Gly Thr Cys Thr Leu Arg Glu Ala Ile Ile Val
         145                 150                 155

GGT AGC ATC ATC ACC AAG TGC TCC ATC CCT GTG TTG CAC TCC AGT GCG          588
Gly Ser Ile Ile Thr Lys Cys Ser Ile Pro Val Leu His Ser Ser Ala
     160                 165                 170

GCC ATG CTG AAA ATT GCT GAG ATG GAA TAC AGC GGT GCC AAC AGC ATC          636
Ala Met Leu Lys Ile Ala Glu Met Glu Tyr Ser Gly Ala Asn Ser Ile
175                 180                 185

TTC CTG CGA CTG CTG CTG GAT AAG AAG TAT GCA CTG CCT TAC CGG GTG          684
Phe Leu Arg Leu Leu Leu Asp Lys Lys Tyr Ala Leu Pro Tyr Arg Val
```

```
                190                 195                 200                 205
CTG GAT GCC CTA GTC TTC CAC TTC CTG GGG TTC CGG ACA GAG AAG CGT        732
Leu Asp Ala Leu Val Phe His Phe Leu Gly Phe Arg Thr Glu Lys Arg
            210                 215                 220

GAA CTG CCT GTG CTG TGG CAC CAG TGC CTC CTG ACT TTG GTC CAG CGC        780
Glu Leu Pro Val Leu Trp His Gln Cys Leu Leu Thr Leu Val Gln Arg
            225                 230                 235

TAC AAG GCC GAC TTG GCC ACA GAC CAG AAA GAG GCC CTC TTA GAA CTG        828
Tyr Lys Ala Asp Leu Ala Thr Asp Gln Lys Glu Ala Leu Leu Glu Leu
            240                 245                 250

CTC CGG CTG CAG CCC CAT CCA CAG CTA TCG CCC GAA ATC AGG CGT GAG        876
Leu Arg Leu Gln Pro His Pro Gln Leu Ser Pro Glu Ile Arg Arg Glu
            255                 260                 265

CTT CAG AGT GCA GCC CCC GCA TGT GGA AGA TGT TCC CAT CAC CGT GGA        924
Leu Gln Ser Ala Ala Pro Ala Cys Gly Arg Cys Ser His His Arg Gly
270                 275                 280                 285

GTG AGG AAA ACA GTC AGC TTG TCC TGG CCA AAG GGG TTT GGA AGG ACA        972
Val Arg Lys Thr Val Ser Leu Ser Trp Pro Lys Gly Phe Gly Arg Thr
            290                 295                 300

CCA AGA CCC CGT TGG T GACTGAAGAT GACACTGAGC TTTAATGGCT GAAGACCCAG     1028
Pro Arg Pro Arg Trp
            305

ATCAGGGCAG TGACCAGATC ACAGGGACAT CTGTGGCTCC CAGTCCAGGA CAGGAAGGAC     1088

TGAGGGTCTG GCTGGTTCCC TCTTCCATTC TAGGCCCTTA TCCCTGTTTA GTTCTGAGAG     1148

CCAACTTGAG ATACCATATG CTAGCATTCC CAGTCCCCAG CTGGGGCTTG GTGTGAGTAC     1208

TTTTTCTATG CTATTGTGT CAGGTCACTG TGGATAAAGG CAAAGACAGA TATTTATTGA      1268

AAAAAAAAAA AAAAAAAAA AAAAA                                            1293

(2) INFORMATION FOR SEQ ID NO:7:

(i) SEQUENCE CHARACTERISTICS:
        (A) LENGTH: 306 amino acids
        (B) TYPE: amino acid
        (D) TOPOLOGY: linear (ii) MOLECULE TYPE: protein (xi) SEQUENCE DESCRIPTION: SEQ ID NO:7:

Met Glu Lys Leu Thr Glu Lys Gln Thr Glu Val Glu Thr Val Met Ser
 1               5                  10                  15

Glu Val Ser Gly Phe Pro Met Pro Gln Leu Asp Pro Arg Val Leu Glu
                20                  25                  30

Val Tyr Arg Gly Val Arg Glu Val Leu Ser Lys Tyr Arg Ser Gly Lys
            35                  40                  45

Leu Pro Lys Ala Phe Lys Ile Ile Pro Ala Leu Ser Asn Trp Glu Gln
        50                  55                  60

Ile Leu Tyr Val Thr Glu Pro Glu Ala Trp Thr Ala Ala Ala Met Tyr
65                  70                  75                  80

Gln Ala Thr Arg Ile Phe Ala Ser Asn Leu Lys Glu Arg Met Ala Gln
                85                  90                  95

Arg Phe Tyr Asn Leu Val Leu Pro Arg Val Arg Asp Asp Val Gly
            100                 105                 110

Glu Tyr Lys Arg Leu Asn Phe His Leu Tyr Met Ala Leu Lys Lys Ala
        115                 120                 125

Leu Phe Lys Pro Gly Ala Trp Phe Lys Gly Ile Leu Ile Pro Leu Cys
    130                 135                 140

Glu Ser Gly Thr Cys Thr Leu Arg Glu Ala Ile Ile Val Gly Ser Ile
```

```
145                 150                 155                 160
Ile Thr Lys Cys Ser Ile Pro Val Leu His Ser Ala Ala Met Leu
            165                 170                 175

Lys Ile Ala Glu Met Glu Tyr Ser Gly Ala Asn Ser Ile Phe Leu Arg
        180                 185                 190

Leu Leu Leu Asp Lys Lys Tyr Ala Leu Pro Tyr Arg Val Leu Asp Ala
            195                 200                 205

Leu Val Phe His Phe Leu Gly Phe Arg Thr Glu Lys Arg Glu Leu Pro
        210                 215                 220

Val Leu Trp His Gln Cys Leu Leu Thr Leu Val Gln Arg Tyr Lys Ala
225                 230                 235                 240

Asp Leu Ala Thr Asp Gln Lys Glu Ala Leu Leu Glu Leu Leu Arg Leu
            245                 250                 255

Gln Pro His Pro Gln Leu Ser Pro Glu Ile Arg Arg Glu Leu Gln Ser
            260                 265                 270

Ala Ala Pro Ala Cys Gly Arg Cys Ser His His Arg Gly Val Arg Lys
            275                 280                 285

Thr Val Ser Leu Ser Trp Pro Lys Gly Phe Gly Arg Thr Pro Arg Pro
            290                 295                 300

Arg Trp
305

(2) INFORMATION FOR SEQ ID NO:8:

(i) SEQUENCE CHARACTERISTICS:
        (A) LENGTH: 2223 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 199..2223

(xi) SEQUENCE DESCRIPTION: SEQ ID NO:8:

CACCTCTGTC GTTCCCCAGT GTTCCACAAG AAGAAACCTT ACGTCAGGCC CCTGCTGGAC      60

TCCCCCGAGA AACTCTGTTC CAATCCCGCG TTCTTCCTCC CAAAGAAATT CCTTCTTTGT     120

CTCCCACCAT TCCCCGTCAA GGCTCCCTGC CCCAAACTTC CAGTGCTCCC AAGCAAGAGA     180

CTTCTGGCTG GATGCCAC ATG TGC TCC AGA AGG GAC CCT CAC TCC TGT GTT      231
                    Met Cys Ser Arg Arg Asp Pro His Ser Cys Val
                     1               5                  10

CTG CCG CTT CTG AGC AAG AGA CTT CTC TCC AGG GCC CCC TGG CTT CCC      279
Leu Pro Leu Leu Ser Lys Arg Leu Leu Ser Arg Ala Pro Trp Leu Pro
            15                  20                  25

AGG AAG GGA CCC AGT ATC CAC CCC CAG CTG GTG GTG AAC AAG AAG CCT      327
Arg Lys Gly Pro Ser Ile His Pro Gln Leu Val Val Asn Lys Lys Pro
        30                  35                  40

CCC TTC TCT CCC ACT CCC CCC ACC ACC AGG AAG CCC CCG CTC ACT CCC      375
Pro Phe Ser Pro Thr Pro Pro Thr Thr Arg Lys Pro Pro Leu Thr Pro
    45                  50                  55

CTG AAG CTC CTG AGA AAG ACC CCT GAC CCT TCC CCA ACA GTT CCC GAG      423
Leu Lys Leu Leu Arg Lys Thr Pro Asp Pro Ser Pro Thr Val Pro Glu
 60                  65                  70                  75

ACT GAC ATG GAC CCG CTG CTC CAG AGC CCG GTT TCC CAA AAG GAC ACC      471
Thr Asp Met Asp Pro Leu Leu Gln Ser Pro Val Ser Gln Lys Asp Thr
            80                  85                  90

CCT TTC CAG ATC TCT TCT GGA GTC CAG AAG GAA CAG CCG CTC CCC ACG      519
Pro Phe Gln Ile Ser Ser Gly Val Gln Lys Glu Gln Pro Leu Pro Thr
        95                  100                 105
```

```
GGA GAG ATC ACC CGC TTG GGT GTG TGG GCT GCC GTC CAA GCA GTG GAG      567
Gly Glu Ile Thr Arg Leu Gly Val Trp Ala Ala Val Gln Ala Val Glu
            110                 115                 120

AGG AAG CTG GAG GCC CAG GCC ATG AGG CTA CTG ACC CTG GAA GGC AGG      615
Arg Lys Leu Glu Ala Gln Ala Met Arg Leu Leu Thr Leu Glu Gly Arg
        125                 130                 135

ACG GGG ACA AAT GAA AAG AAG ATA GCC GAC TGC GAG AAG ACA GCC GTG      663
Thr Gly Thr Asn Glu Lys Lys Ile Ala Asp Cys Glu Lys Thr Ala Val
140                 145                 150                 155

GAG TTC GCG AAC CAT CTG GAG AGC AAG TGG GTC GTG TTG GGG ACC CTG      711
Glu Phe Ala Asn His Leu Glu Ser Lys Trp Val Val Leu Gly Thr Leu
                160                 165                 170

CTG CAG GAG TAT GGG CTG CAG CAG AGG CGG CTG GAG AAC ATG GAG AAC      759
Leu Gln Glu Tyr Gly Leu Gln Gln Arg Arg Leu Glu Asn Met Glu Asn
            175                 180                 185

CTG CTG AAA AAC AGA AAT TTC TGG ATC CTG CGG CTG CCC CCC GGC AGC      807
Leu Leu Lys Asn Arg Asn Phe Trp Ile Leu Arg Leu Pro Pro Gly Ser
        190                 195                 200

AAT GGA GAA GTT CCC AAG GTC CCT GTC ACA TTT GAT GAT GTT GCT GTG      855
Asn Gly Glu Val Pro Lys Val Pro Val Thr Phe Asp Asp Val Ala Val
205                 210                 215

CAC TTC TCG GAG CAG GAG TGG GGA AAC CTG TCT GAG TGG CAG AAG GAG      903
His Phe Ser Glu Gln Glu Trp Gly Asn Leu Ser Glu Trp Gln Lys Glu
220                 225                 230                 235

CTC TAC AAG AAC GTG ATG AGG GGC AAC TAC GAG TCC CTG GTT TCC ATG      951
Leu Tyr Lys Asn Val Met Arg Gly Asn Tyr Glu Ser Leu Val Ser Met
            240                 245                 250

GAC TAT GCA ATT TCC AAA CCA GAC CTC ATG TCA CAG ATG GAG CGC GGG      999
Asp Tyr Ala Ile Ser Lys Pro Asp Leu Met Ser Gln Met Glu Arg Gly
        255                 260                 265

GAG CGG CCC ACC ATG CAG GAG CAG GAA GAC TCT GAG GAG GGC GAA ACG     1047
Glu Arg Pro Thr Met Gln Glu Gln Glu Asp Ser Glu Glu Gly Glu Thr
    270                 275                 280

CCG ACA GAT CCC AGT GCT GCG CAC GAT GGG ATC GTG ATT AAG ATC GAG     1095
Pro Thr Asp Pro Ser Ala Ala His Asp Gly Ile Val Ile Lys Ile Glu
285                 290                 295

GTA CAG ACC AAC GAC GAG GGC TCA GAA AGT TTG GAG ACA CCT GAG CCC     1143
Val Gln Thr Asn Asp Glu Gly Ser Glu Ser Leu Glu Thr Pro Glu Pro
300                 305                 310                 315

CTG ATG GGA CAG GTG GAA GAG CAC GGC TTC CAG GAC TCA GAG CTG GGT     1191
Leu Met Gly Gln Val Glu Glu His Gly Phe Gln Asp Ser Glu Leu Gly
            320                 325                 330

GAN CCC TGT GGG GAA CAG CCA GAC CTG GAC ATG CAG GAG CCA GAG AAC     1239
Xaa Pro Cys Gly Glu Gln Pro Asp Leu Asp Met Gln Glu Pro Glu Asn
        335                 340                 345

ACG CTG GAG GAG TCC ACG GAA GGC TCC AGC GAG TTC AGC GAA CTG AAG     1287
Thr Leu Glu Glu Ser Thr Glu Gly Ser Ser Glu Phe Ser Glu Leu Lys
    350                 355                 360

CAG ATG CTG GTG CAG CAG AGG AAC TGC ACG GAG GGG ATC GTG ATC AAG     1335
Gln Met Leu Val Gln Gln Arg Asn Cys Thr Glu Gly Ile Val Ile Lys
365                 370                 375

ACA GAG GAA CAA GAC GAG GAG GAA GAA GAG GAG GAG GAG GAT GAG CTG     1383
Thr Glu Glu Gln Asp Glu Glu Glu Glu Glu Glu Glu Glu Asp Glu Leu
380                 385                 390                 395

CCG CAG CAC TTG CAA TCC CTT GGG CAG CTG TCC GGG AGA TAT GAG GCC     1431
Pro Gln His Leu Gln Ser Leu Gly Gln Leu Ser Gly Arg Tyr Glu Ala
            400                 405                 410

AGT ATG TAC CAG ACC CCG CTG CCC GGG GAG ATG TCC CCG GAG GGC GAG     1479
Ser Met Tyr Gln Thr Pro Leu Pro Gly Glu Met Ser Pro Glu Gly Glu
        415                 420                 425
```

```
GAG AGC CCC CCG CCC CTG CAG GTT GGA AAC CCC GCA GTG AAA AGG CTG      1527
Glu Ser Pro Pro Pro Leu Gln Val Gly Asn Pro Ala Val Lys Arg Leu
            430                 435                 440

GCG CCC TCC GTG CAC GGT GAG CGG GAC CTG AGC GAG AAC CGC GGG GGC      1575
Ala Pro Ser Val His Gly Glu Arg Asp Leu Ser Glu Asn Arg Gly Gly
445                 450                 455

TCG AGC CAG CAG AGT GGG AAC CGG CGC GGC GAG CGG CCC TTC ACA TGC      1623
Ser Ser Gln Gln Ser Gly Asn Arg Arg Gly Glu Arg Pro Phe Thr Cys
460                 465                 470                 475

ATG GAG TGC GGC AAG AGC TTC CGC CTG AAG ATC AAC CTC ATC ATC CAC      1671
Met Glu Cys Gly Lys Ser Phe Arg Leu Lys Ile Asn Leu Ile Ile His
                480                 485                 490

CAC CAG CGC AAC CAA CAT CAA GGA GGG GGC CCT ACG AGT GCG CCG AAT      1719
His Gln Arg Asn Gln His Gln Gly Gly Gly Pro Thr Ser Ala Pro Asn
            495                 500                 505

GTG AGA TCA GCT TTC CGG CAC AAG CAA CAG CTC ACG CTG CAC CAG CGC      1767
Val Arg Ser Ala Phe Arg His Lys Gln Gln Leu Thr Leu His Gln Arg
510                 515                 520

ATC CAC CGC GTG CGC GGA GGC TGC GTC TCA CCC GAA CGC GGG CCC ACG      1815
Ile His Arg Val Arg Gly Gly Cys Val Ser Pro Glu Arg Gly Pro Thr
525                 530                 535

TTC AAC CCC AAG NAC GCG CTC AAG CCG CGT CCC AAG TCA CCC AGC TCT      1863
Phe Asn Pro Lys Xaa Ala Leu Lys Pro Arg Pro Lys Ser Pro Ser Ser
540                 545                 550                 555

GGT AGC GGC GGC GGT GGC CCT AAG CCC TAC AAG TGC CCC GAG TGC GAC      1911
Gly Ser Gly Gly Gly Gly Pro Lys Pro Tyr Lys Cys Pro Glu Cys Asp
                560                 565                 570

AGC AGC TTC AGC CAC AAG TCC AGC CTG ACT AAA CAC CAG ATC ACG CAC      1959
Ser Ser Phe Ser His Lys Ser Ser Leu Thr Lys His Gln Ile Thr His
            575                 580                 585

ACG GGT GAG CGG CCC TAC ACG TGC CCC GAG TGC AAG AAG AGC TTC CGC      2007
Thr Gly Glu Arg Pro Tyr Thr Cys Pro Glu Cys Lys Lys Ser Phe Arg
            590                 595                 600

CTG CAC ATC AGC TTG GTG ATC CAT CAG CGC GTG CAC GCG GGC AAG CAT      2055
Leu His Ile Ser Leu Val Ile His Gln Arg Val His Ala Gly Lys His
605                 610                 615

GAG GTC TCC TTC ATC TGC AGC CTG TGC GGC AAG AGC TTC AGC CGC CCC      2103
Glu Val Ser Phe Ile Cys Ser Leu Cys Gly Lys Ser Phe Ser Arg Pro
620                 625                 630                 635

TCG CAC CTG CTG CGC CAC CAG CGG ACT CAC ACA GGC GAG CGG CCC TTC      2151
Ser His Leu Leu Arg His Gln Arg Thr His Thr Gly Glu Arg Pro Phe
                640                 645                 650

AAG TGC CCC GAG TGC GAG AAG AGC TTC AGC GAG AAG TCC AAG CTC ACC      2199
Lys Cys Pro Glu Cys Glu Lys Ser Phe Ser Glu Lys Ser Lys Leu Thr
            655                 660                 665

AAC CAC TGC CGC GTG CAC TCG CGC                                      2223
Asn His Cys Arg Val His Ser Arg
            670                 675

(2) INFORMATION FOR SEQ ID NO:9:

(i) SEQUENCE CHARACTERISTICS:
        (A) LENGTH: 675 amino acids
        (B) TYPE: amino acid
        (D) TOPOLOGY: linear (ii) MOLECULE TYPE: protein (xi) SEQUENCE DESCRIPTION: SEQ ID NO:9:

Met Cys Ser Arg Arg Asp Pro His Ser Cys Val Leu Pro Leu Leu Ser
1               5                   10                  15
```

-continued

```
Lys Arg Leu Leu Ser Arg Ala Pro Trp Leu Pro Arg Lys Gly Pro Ser
         20                  25                  30

Ile His Pro Gln Leu Val Val Asn Lys Lys Pro Pro Phe Ser Pro Thr
         35                  40                  45

Pro Pro Thr Thr Arg Lys Pro Leu Thr Pro Leu Lys Leu Leu Arg
 50                  55                  60

Lys Thr Pro Asp Pro Ser Pro Thr Val Pro Glu Thr Asp Met Asp Pro
 65                  70                  75                  80

Leu Leu Gln Ser Pro Val Ser Gln Lys Asp Thr Pro Phe Gln Ile Ser
                 85                  90                  95

Ser Gly Val Gln Lys Glu Gln Pro Leu Pro Thr Gly Glu Ile Thr Arg
                100                 105                 110

Leu Gly Val Trp Ala Ala Val Gln Ala Val Glu Arg Lys Leu Glu Ala
                115                 120                 125

Gln Ala Met Arg Leu Leu Thr Leu Glu Gly Arg Thr Gly Thr Asn Glu
130                 135                 140

Lys Lys Ile Ala Asp Cys Glu Lys Thr Ala Val Glu Phe Ala Asn His
145                 150                 155                 160

Leu Glu Ser Lys Trp Val Val Leu Gly Thr Leu Leu Gln Glu Tyr Gly
                165                 170                 175

Leu Gln Gln Arg Arg Leu Glu Asn Met Glu Asn Leu Leu Lys Asn Arg
                180                 185                 190

Asn Phe Trp Ile Leu Arg Leu Pro Pro Gly Ser Asn Gly Glu Val Pro
                195                 200                 205

Lys Val Pro Val Thr Phe Asp Asp Val Ala Val His Phe Ser Glu Gln
    210                 215                 220

Glu Trp Gly Asn Leu Ser Glu Trp Gln Lys Glu Leu Tyr Lys Asn Val
225                 230                 235                 240

Met Arg Gly Asn Tyr Glu Ser Leu Val Ser Met Asp Tyr Ala Ile Ser
                245                 250                 255

Lys Pro Asp Leu Met Ser Gln Met Glu Arg Gly Glu Arg Pro Thr Met
                260                 265                 270

Gln Glu Gln Glu Asp Ser Glu Glu Gly Glu Thr Pro Thr Asp Pro Ser
                275                 280                 285

Ala Ala His Asp Gly Ile Val Ile Lys Ile Glu Val Gln Thr Asn Asp
290                 295                 300

Glu Gly Ser Glu Ser Leu Glu Thr Pro Glu Pro Leu Met Gly Gln Val
305                 310                 315                 320

Glu Glu His Gly Phe Gln Asp Ser Glu Leu Gly Xaa Pro Cys Gly Glu
                325                 330                 335

Gln Pro Asp Leu Asp Met Gln Glu Pro Glu Asn Thr Leu Glu Glu Ser
                340                 345                 350

Thr Glu Gly Ser Ser Glu Phe Ser Glu Leu Lys Gln Met Leu Val Gln
                355                 360                 365

Gln Arg Asn Cys Thr Glu Gly Ile Val Ile Lys Thr Glu Glu Gln Asp
                370                 375                 380

Glu Glu Glu Glu Glu Glu Glu Asp Glu Leu Pro Gln His Leu Gln
385                 390                 395                 400

Ser Leu Gly Gln Leu Ser Gly Arg Tyr Glu Ala Ser Met Tyr Gln Thr
                405                 410                 415

Pro Leu Pro Gly Glu Met Ser Pro Glu Gly Glu Glu Ser Pro Pro Pro
                420                 425                 430

Leu Gln Val Gly Asn Pro Ala Val Lys Arg Leu Ala Pro Ser Val His
                435                 440                 445
```

-continued

```
Gly Glu Arg Asp Leu Ser Glu Asn Arg Gly Ser Ser Gln Gln Ser
450                     455                     460

Gly Asn Arg Arg Gly Glu Arg Pro Phe Thr Cys Met Glu Cys Gly Lys
465                     470                     475                 480

Ser Phe Arg Leu Lys Ile Asn Leu Ile Ile His His Gln Arg Asn Gln
                485                     490                     495

His Gln Gly Gly Gly Pro Thr Ser Ala Pro Asn Val Arg Ser Ala Phe
                500                     505                     510

Arg His Lys Gln Gln Leu Thr Leu His Gln Arg Ile His Arg Val Arg
                515                     520                     525

Gly Gly Cys Val Ser Pro Glu Arg Gly Pro Thr Phe Asn Pro Lys Xaa
            530                     535                     540

Ala Leu Lys Pro Arg Pro Lys Ser Pro Ser Ser Gly Ser Gly Gly Gly
545                     550                     555                     560

Gly Pro Lys Pro Tyr Lys Cys Pro Glu Cys Asp Ser Ser Phe Ser His
                565                     570                     575

Lys Ser Ser Leu Thr Lys His Gln Ile Thr His Thr Gly Glu Arg Pro
                580                     585                     590

Tyr Thr Cys Pro Glu Cys Lys Lys Ser Phe Arg Leu His Ile Ser Leu
                595                     600                     605

Val Ile His Gln Arg Val His Ala Gly Lys His Glu Val Ser Phe Ile
            610                     615                     620

Cys Ser Leu Cys Gly Lys Ser Phe Ser Arg Pro Ser His Leu Leu Arg
625                     630                     635                     640

His Gln Arg Thr His Thr Gly Glu Arg Pro Phe Lys Cys Pro Glu Cys
                645                     650                     655

Glu Lys Ser Phe Ser Glu Lys Ser Lys Leu Thr Asn His Cys Arg Val
                660                     665                     670

His Ser Arg
        675

(2) INFORMATION FOR SEQ ID NO:10:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:10:

Phe Glu Ile Glu Ala Arg Ala Gln Glu
1               5

(2) INFORMATION FOR SEQ ID NO:11:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:11:

Asp Gln Glu Asn Gln Asp Pro Arg Arg
1               5

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear
```

(xi) SEQUENCE DESCRIPTION: SEQ ID NO:12:

GGAATTCATG AGCGATGGCT TTGGCAGTAG                30

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:13:

CGTCGACTCA GTTTGGTCCA CCGCCGAAGC CAG             33

(2) INFORMATION FOR SEQ ID NO:14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:14:

GGAATTCATG GATGGCTCTC CCAGCACTGG TG              32

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:15:

GCAGCTGAGT GCTGGTGCTT AGTGTACCAC C               31

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:16:

GGAATTCATG CCCAGCAACA GCATTGGC                   28

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:17:

GCAGCTGAGT ACTGGTGCTG GGTCCATCAC AAAAAC          36

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:18:

```
GGAATTCATG GATATCGACT GCCTA                                                    25
```

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:19:

```
GCAGCTGAGT CTGGAGCTGG GTGCACCAT                                                29
```

(2) INFORMATION FOR SEQ ID NO:20:

(i) SEQUENCE CHARACTERISTICS:
        (A) LENGTH: 87 amino acids
        (B) TYPE: amino acid
        (D) TOPOLOGY: linear (xi) SEQUENCE DESCRIPTION: SEQ ID NO:20:

```
Asp Gly Ser Pro Ser Thr Gly Ala Gly Phe Gly Gly Ala Leu Asn Thr
1               5                   10                  15

Ser Ala Ser Phe Gly Ser Val Leu Asn Thr Ser Thr Gly Phe Gly Gly
                20                  25                  30

Ala Met Ser Thr Ser Ala Asp Phe Gly Gly Thr Leu Ser Thr Ser Val
            35                  40                  45

Cys Phe Gly Gly Ser Pro Gly Thr Ser Val Ser Phe Gly Ser Ala Leu
        50                  55                  60

Asn Thr Asn Ala Gly Tyr Gly Gly Ala Val Ser Thr Asn Thr Asp Phe
65                  70                  75                  80

Gly Gly Thr Leu Ser Thr Ser
                85
```

(2) INFORMATION FOR SEQ ID NO:21:

(i) SEQUENCE CHARACTERISTICS:
        (A) LENGTH: 72 amino acids
        (B) TYPE: amino acid
        (D) TOPOLOGY: linear (xi) SEQUENCE DESCRIPTION: SEQ ID NO:21:

```
Pro Ser Asn Ser Ile Gly Phe Gly Ala Ala Pro Ser Thr Ser Val Ser
1               5                   10                  15

Phe Gly Gly Ala His Gly Thr Ser Leu Cys Phe Gly Gly Ala Pro Ser
                20                  25                  30

Thr Ser Leu Cys Phe Gly Ser Ala Ser Asn Thr Asn Leu Cys Phe Gly
            35                  40                  45

Gly Pro Pro Ser Thr Ser Ala Cys Phe Ser Gly Ala Thr Ser Pro Ser
        50                  55                  60

Phe Cys Asp Gly Pro Ser Thr Ser
65                  70
```

(2) INFORMATION FOR SEQ ID NO:22:

(i) SEQUENCE CHARACTERISTICS:
        (A) LENGTH: 86 amino acids
        (B) TYPE: amino acid
        (D) TOPOLOGY: linear (xi) SEQUENCE DESCRIPTION: SEQ ID NO:22:

```
Ser Asp Gly Phe Gly Ser Arg Pro Asn Ala Ser Phe Asp Arg Gly Leu
```

-continued

```
1               5              10             15

Ser Thr Ile Ile Gly Phe Gly Ser Gly Ser Asn Thr Ser Thr Gly Phe
            20                  25                  30

Thr Gly Glu Pro Ser Thr Ser Thr Gly Phe Ser Ser Gly Pro Ser Ser
        35                  40                  45

Ile Val Gly Phe Ser Gly Gly Pro Ser Thr Gly Val Gly Phe Cys Ser
        50                  55                  60

Gly Pro Ser Thr Ser Gly Phe Ser Gly Gly Pro Ser Thr Gly Ala Gly
65                  70                  75                  80

Phe Gly Gly Gly Pro Asn
                85
```